United States Patent
Zhang

(10) Patent No.: US 11,890,382 B2
(45) Date of Patent: *Feb. 6, 2024

(54) EDIBLE PLANT-DERIVED MICROVESICLE COMPOSITIONS FOR DIAGNOSIS AND TREATMENT OF DISEASE

(71) Applicant: University of Louisville Research Foundation, Inc., Louisville, KY (US)

(72) Inventor: Huang-Ge Zhang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,085

(22) Filed: Apr. 12, 2019

(65) Prior Publication Data

US 2020/0188311 A1  Jun. 18, 2020

Related U.S. Application Data

(63) Continuation of application No. 14/356,853, filed as application No. PCT/US2012/056298 on Sep. 20, 2012, now abandoned.

(60) Provisional application No. 61/556,565, filed on Nov. 7, 2011.

(51) Int. Cl.
| | |
|---|---|
| A61K 9/127 | (2006.01) |
| A61K 9/48 | (2006.01) |
| A61K 36/87 | (2006.01) |
| A61K 36/81 | (2006.01) |
| A61K 36/752 | (2006.01) |
| A61K 31/12 | (2006.01) |
| A61K 31/337 | (2006.01) |
| A61K 31/519 | (2006.01) |
| A61K 31/713 | (2006.01) |
| A61K 45/06 | (2006.01) |
| A61K 47/46 | (2006.01) |
| A61K 49/00 | (2006.01) |

(52) U.S. Cl.
CPC ............ *A61K 9/4816* (2013.01); *A61K 31/12* (2013.01); *A61K 31/337* (2013.01); *A61K 31/519* (2013.01); *A61K 31/713* (2013.01); *A61K 36/752* (2013.01); *A61K 36/81* (2013.01); *A61K 36/87* (2013.01); *A61K 45/06* (2013.01); *A61K 47/46* (2013.01); *A61K 49/0004* (2013.01); *A61K 49/005* (2013.01)

(58) Field of Classification Search
None
See application file for complete search history.

(56) References Cited

U.S. PATENT DOCUMENTS

| | | |
|---|---|---|
| 5,015,483 A | 5/1991 | Haynes et al. |
| 5,672,301 A | 9/1997 | Orly et al. |
| 7,897,356 B2 | 3/2011 | Klass et al. |
| 9,717,733 B2 | 8/2017 | Zhang |
| 9,752,148 B2 | 9/2017 | Zhang |
| 10,590,171 B2 | 3/2020 | Silvas et al. |
| 2010/0048888 A1 | 2/2010 | Chen et al. |
| 2010/0209415 A1 | 8/2010 | Smith et al. |
| 2010/0298151 A1 | 11/2010 | Taylor et al. |
| 2011/0010817 A1 | 1/2011 | Théberge et al. |
| 2012/0183575 A1 | 7/2012 | Gabrielsson |
| 2012/0315324 A1 | 12/2012 | Zhang |
| 2013/0115241 A1 | 5/2013 | Gho |
| 2013/0129790 A1 | 5/2013 | Alexis et al. |
| 2014/0093557 A1 | 4/2014 | Zhang |
| 2016/0354313 A1 | 12/2016 | De Beer et al. |
| 2019/0382539 A1 | 12/2019 | Zhang |
| 2020/0046788 A1 | 2/2020 | Zhang |
| 2020/0063208 A1 | 2/2020 | Zhang |
| 2020/0206297 A1 | 7/2020 | Zhang |
| 2021/0085744 A1 | 3/2021 | Zhang |
| 2021/0236612 A1 | 8/2021 | Zhang |
| 2022/0142937 A1 | 5/2022 | Zhang |

FOREIGN PATENT DOCUMENTS

| | | |
|---|---|---|
| AU | 2008207735 | 7/2008 |
| CN | 106924730 | 7/2017 |
| EP | 3 129 010 | 12/2019 |
| WO | WO 2004/019916 | 3/2004 |
| WO | WO 2008/092153 | 7/2008 |

(Continued)

OTHER PUBLICATIONS

Sun et al., A novel Nanoparticle Drug Delivery System: The Anti-inflammatory Activity of Curcumin Is Enhanced When Encapsulated in Exosomes, The American Society of Gene & Cell Therapy, vol. 18 No. 9, 1606-1614 Sep. 2010 (Year: 2010).*
Qianli An et al., Do Plant Cells Secrete Exosomes Derived from Multivesicular Bodies?; Plant Signaling & Behavior 2:1, 4-7; Jan./Feb. 2007 (Year: 2007).*
Blasovich et al., Discovery of JSI-124 (Cucurbitacin I), a Selective Janus Kinase/Signal Transducer and Activator of Transcriptiopn 3 Signaling Pathway Inhibitor with Potent Antitumor Activity against Human and Murine Cancer Cells in Mice, Cancer Research 63, 1270-Ir9, Mar. 15, 2003 (Year: 2003).*
Zoller, Tetraspanins: push and pull in suppressing and promoting metastasis, Nature Reviews: vol. 9, Jan. 2009; p. 40-55 (hereinafter Zoller). (Year: 2009).*
Gerald W. Dryden, Jr. "Phase I Clinical Trial Investigating the Ability of Plant Exosomes to Deliver Curcumin to Normal and Malignant Colon Tissue". (Year: 2011).*

(Continued)

*Primary Examiner* — Susan T Tran

(74) *Attorney, Agent, or Firm* — Jenkins, Taylor & Hunt, P.A.

(57) ABSTRACT

Compositions comprising a therapeutic agent encapsulated by an edible plant-derived microvesicle are provided. Methods of treating an inflammatory disorder and methods of treating a cancer are further provided and include administering an effective amount of a composition comprising a therapeutic agent encapsulated by an edible plant-derived microvesicle to a subject. Further provided are methods of diagnosing a colon cancer that include the steps of administering an edible plant-derived microvesicle incorporating a detectable label to a subject and then determining an amount of the detectable label in an intestine of the subject.

9 Claims, 64 Drawing Sheets

(56) References Cited

FOREIGN PATENT DOCUMENTS

| WO | WO 2009/065561 | 5/2009 |
|----|----|----|
| WO | WO 2009/147519 | 12/2009 |
| WO | WO 2010/096597 | 8/2010 |
| WO | WO 2011/097480 | 8/2011 |
| WO | WO 2013/048734 | 4/2013 |
| WO | WO 2013/070324 | 5/2013 |
| WO | WO 2014/028487 | 2/2014 |
| WO | WO 2015/058148 | 4/2015 |
| WO | WO 2015/157652 A1 | 10/2015 |
| WO | WO 2017/004526 | 1/2017 |
| WO | WO 2017/083068 | 5/2017 |
| WO | WO 2017/176792 | 10/2017 |
| WO | WO 2018/039119 | 3/2018 |
| WO | WO 2018/071806 | 4/2018 |
| WO | WO 2018/098247 | 5/2018 |
| WO | WO 2019/104242 | 5/2019 |
| WO | WO 2019/173487 | 9/2019 |
| WO | WO 2019/210189 | 10/2019 |

OTHER PUBLICATIONS

Decision to Grant corresponding to European Patent No. 15 776 590.0-1112 dated Nov. 7, 2019.
European Patent Office, Extended European Search Report, EP Application No. 17875026.1, 20 pgs., dated Jul. 2, 2020.
Examination Report for AU Patent Application No. 2016288643, 5 pages, dated Aug. 18, 2020.
Greaney et al. (2016) "Sulforaphane Inhibits Multiple Inflammasomes through an Nrf2-Independent Mechanism," Journal of Leukocyte Biology, vol. 99, pp. 189-199.
He et al. (2014) "MiR-23a Functions as a Tumor Suppressor in Osteosarcoma," Cell Physiol Biochem, vol. 34, pp. 1485-1496.
International Preliminary Report on Patentability corresponding to International Application No. PCT/US12/056298, dated May 22, 2014.
International Search Report and Written Opinion issued in corresponding International Application No. PCT/US19/29377, dated Sep. 9, 2019, 12 pages.
International Search Report and Written Opinion issued in corresponding Application No. PCT/US19/020971, dated May 23, 2019.
International Search Report and Written Opinion issued in corresponding Application No. PCT/US18/062349, dated Apr. 29, 2019.
International Preliminary Report on Patentability corresponding to International Application No. PCT/US18/062349, dated May 26, 2020.
International Preliminary Report on Patentability corresponding to International Application No. PCT/US17/056570, dated Apr. 25, 2019.
International Preliminary Report on Patentability corresponding to International Application No. PCT/US17/062970, dated Jun. 6, 2019.
Long et al. (2009) "Let-7a MicroRNA Functions as a Potential Tumor Suppressor in Human Laryngeal Cancer," Oncology Reports, vol. 22, pp. 1189-1195.
Min-Ji Bak et al., "6-Shogaol-Rich Extract from Ginger Up-Regulates the Antioxidant Defense Systems in Cells and Mice," Molecules, vol. 17, No. 7, Jul. 4, 2012, pp. 8037-8055.
Mueller et al., "Examination of the Anti-Inflammatory, Antioxidant, and Xenobiotic-Inducing Potential of Broccoli Extract and Various Essential Oils during a Mild DSS-Induced Colitis in Rats," ISRN Gastroenterology, vol. 2013, Jan. 20, 2013, pp. 1-14.
Notice of Allowance corresponding to U.S. Appl. No. 16/523,761 dated Jun. 11, 2020.
Notice of Allowance corresponding to U.S. Appl. No. 15/948,218 dated Apr. 27, 2020.
Office Action corresponding with European Patent Application No. 16818891.0 dated Feb. 1, 2021.
Office Action corresponding with European Patent Application No. 17875026.1 dated Apr. 9, 2021.
Office Action corresponding to U.S. Appl. No. 15/821,408 dated Nov. 12, 2019.
Office Action corresponding to U.S. Appl. No. 15/740,591 dated Mar. 9, 2020.
Office Action corresponding to U.S. Appl. No. 15/740,591 dated May 26, 2021.
Office Action corresponding to U.S. Appl. No. 16/340,457 dated Mar. 22, 2021.
Office Action corresponding to U.S. Appl. No. 16/359,618 dated Aug. 10, 2020.
Office Action corresponding to U.S. Appl. No. 16/359,618 dated Apr. 26, 2021.
Office Action corresponding to U.S. Appl. No. 16/377,800 dated Apr. 20, 2020.
Office Action corresponding to U.S. Appl. No. 16/377,800 dated Dec. 21, 2020.
Office Action (Restriction Requirement) corresponding to U.S. Appl. No. 16/462,715 dated Apr. 9, 2021.
Office Action (Restriction Requirement) corresponding to U.S. Appl. No. 16/523,761 dated Nov. 5, 2019.
Office Action corresponding to U.S. Appl. No. 16/523,761 dated Jan. 31, 2020.
Ogata-Kawata et al. (2014) "Circulating Exosomal MicroRNAs as Biomarkers of Colon Cancer," PLOS One, vol. 9, No. 4, pp. 1-9.
Tristan-Ramos (2020) "The Tumor Suppressor MicroRNA let-7 Inhibits Human LINE-1 Retrotransposition," Nature Communications, vol. 11, No. 5712, pp. 1-14.
Wagner et al. (2013) "DSS-Induced Acute Colitis in C57BL/6 Mice is Mitigated by Sulforaphane Pre-Treatment," Journal of Nutritional Biochemistry, vol. 24, pp. 2085-2091.
Wang, et al., "Blood Exosomes Regulate the Tissue Distribution of Grapefruit-Derived Nanovector via CD36 and IGFR1 Pathways", Theranostics, 8(18):4912-4924 (Sep. 9, 2018).
Zhang et al. (2016) "Plant derived edible nanoparticles as a new therapeutic approach against diseases," Tissue Barriers, vol. 4, No. 2, pp. 1-9, specif. p. 1.
Alvarez-Erviti et al. Delivery of siRNA to the mouse brain by systemic injection of targeted exosomes. Nat Biotechnol 29, 341-345 (2011).
Antonyak & Cerione. Microvesicles as mediators of intercellular communication in cancer. Methods in molecular biology. 2014; 1165:147-173.
Arora et al. Synthesis, characterization and evaluation of poly (D,L-lactide-co-glycolide)-based nanoformulation of miRNA-150: potential implications for pancreatic cancer therapy. Int J Nanomedicine, Jun. 18, 2014, vol. 9, pp. 2933-2942.
Badens et al. Microparticles of soy lecithin formed by supercritical processes. Biotechnol Bioeng 2001 ;72:194-204.
Blaskovich. Discovery of JSI-124, a selective janus kinase signal transducer and activator of transcription 3 signaling pathway inhibitor with potent antitumor activity against human and murine cancer cells in mice, Can Res, 2003, 63, 1270-1279.
Bove et al. The Blossoming of RNA biology: Novel Insights from Plant System, RNA (2006), 12:2035-2046.
Chen et al. Enhanced cellular uptake of folic acid-conjugated PLGA-PEG nanoparticles loaded with vincristine sulfate in human breast cancer. Drug Dev Ind Pharm 37, 1339-1346, doi:10.3109/03639045.2011.575162 (2011).
Moorthi et al. Nanotherapeutics to overcome conventional cancer chemotherapy limitations. J Pharm Pharm Sci 14, 67-77 (2011).
Cho et al. "Therapeutic nanoparticles for drug delivery in cancer," Clin. Cancer Res., 2008, vol. 14:(5), pp. 1310-1316.
Cho. MicroRNAs as therapeutic targets and their potential applications in cancer therapy. Expert opinion on therapeutic targets. 2012; 16(8):747-759.
Friedman et al. "Curcumin analogues exhibit enhanced growth suppressive activity in human pancreatic cancer cells," Anticancer Drugs, 2009, vol. 20(6), pp. 444-449.
Fullbeck M, Huang X, Dumdey R, Frommel C, Dubiel W, Preissner R. Novel curcumin- and emodin-related compounds identified by in silico 2D/3D conformer screening induce apoptosis in tumor cells. BMC Cancer. 2005; 5:97. Prepublished on Aug. 9, 2005 as DOI 1471-2407-5-97 [pii]10.1186/1471-2407-5-97.

(56) References Cited

OTHER PUBLICATIONS

Geng et al., MicroRNA-192 suppresses liver metastasis of colon cancer, Oncogene, vol. 33, pp. 5332-5340. (Year: 2014).
Hirsjarvi, S., Passirani, C. & Benoit, J. P. Passive and active tumour targeting with nanocarriers. Curr Drug Discov Technol 8, 188-196 (2011).
International Preliminary Report on Patentability corresponding to International Patent Application No. PCT/US2011/023747 dated Aug. 7, 2012.
Li et al. "Liposomal curcumin with and without oxaliplatin: effects on cell growth, apoptosis, and angiogenesis in colorectal cancer," Mal Cancer Ther, 2007, vol. 6, pp. 1276-1282.
Liu et al. "CII-DC-AdTRAIL cell gene therapy inhibits infiltration of CII-reactive T cells and Gii-induced arthritis," J Clin Invest, 2003, vol. 112, pp. 1332-1341.
Liu et al. "Contribution of MyD88 to the tumor exosome-mediated induction of myeloid derived suppressor cells," Am JPathol, 2010, vol. 176, pp. 2490-2499.
Liu W H, Yeh S H, Lu C C, Yu S L, Chen H Y, Lin C Y, Chen D S and Chen P J. MicroRNA-18a prevents estrogen receptor-alpha expression, promoting proliferation of hepatocellular carcinoma cells. Gastroenterology. 2009; 136(2):683-693.
Liu, J., Kolar, C., Lawson, T. A. & Gmeiner, W. H. Targeted drug delivery to chemoresistant cells: folic acid derivatization of FdUMP[10] enhances cytotoxicity toward 5-FU-resistant human colorectal tumor cells. J Org Chem 66, 5655-5663 (2001).
Lukacs R U, Memarzadeh S, Wu H, Witte O N. Bmi-1 is a crucial regulator of prostate stem cell self-renewal and malignant transformation. Cell Stem Cell. 2010; 7(6):682-693. Prepublished on Nov. 30, 2010 as DOI 10.1016/j.stem.2010.11.013.
Maiti et al. "Curcumin-phospholipid complex: Preparation, therapeutic evaluation and pharmacokinetic study in rats," Int J _ Pharm., 2007, vol. 330, pp. 155-163.
Markman, M., "Pegylated liposomal doxorubicin in the treatment of cancer of the breast and ovary," Expert Opin. Pharmacother, 2006, vol. 7, pp. 1469-1474.
Mayhew, E.G. et al. 1987. Effects of liposome-entrapped doxorubicin on liver metastases of mouse colon carcinomas 26 and 38. Journal of the National Cancer Institute 78(4): 707-713. specif. p. 707, 708.
Mok, H. et al. pH-Sensitive siRNA nanovector for targeted gene silencing and cytotoxic effect in cancer cells. Molecular Pharmaceutics 7, 1930-1939 (2010).
Office Action corresponding with European Patent Application No. 15 776 590.0-1112 dated Nov. 6, 2018.
European Search Report corresponding with European Patent Application No. 16818891.0 dated Jan. 9, 2019.
Office Action corresponding to U.S. Appl. No. 13/576,907 dated Jun. 18, 2013.
Office action (Restriction Requirement) corresponding to U.S. Appl. No. 14/107,691 dated Feb. 13, 2014.
Office Action corresponding to U.S. Appl. No. 14/107,691 dated Jun. 19, 2014.
Office Action corresponding to U.S. Appl. No. 14/107,691 dated Feb. 6, 2015.
Office Action corresponding to U.S. Appl. No. 14/107,691 dated Oct. 6, 2015.
Office Action corresponding to U.S. Appl. No. 14/107,691 dated Jun. 28, 2016.
Office Action corresponding to U.S. Appl. No. 14/107,691 dated Mar. 14, 2017.
Office Action corresponding to U.S. Appl. No. 14/107,691 dated Sep. 13, 2017.
Office Action corresponding to U.S. Appl. No. 15/917,151 dated Sep. 21, 2018.
Office Action corresponding to U.S. Appl. No. 15/740,591 dated Apr. 29, 2019.
Office Action corresponding to U.S. Appl. No. 15/740,591 dated Aug. 13, 2019.
Office Action corresponding to U.S. Appl. No. 16/377,800 dated Oct. 16, 2019.
Pollock, S., Antrobus, R., Newton, L. et al. Uptake and trafficking of liposomes to the endoplasmic reticulum. The FASEB Journal 2010;24:1866-1878.
Powell, J.J., Faria, N., Thomas-McKay, E. et al. Origin and fate of dietary nanoparticles and microparticles in the gastrointestinal tract. J Autoimmun 2010;34:J226-33.
Powell, J.J., Thoree, V., Pele, L.C. Dietary microparticles and their impact on tolerance and immune responsiveness of the gastrointestinal tract. Br J Nutr 2007;98 Suppl 1:S59-63.
Qian B Z, Li J, Zhang H, Kitamura T, Zhang J, Campion L R, Kaiser E A, Snyder L A and Pollard J W. CCL2 recruits inflammatory monocytes to facilitate breast-tumour metastasis. Nature. 2011; 475(7355):222-225.
Qianli et al. Do Plant Cells Secrete Exosomes Derived from Multivesicular Bodies?; Plant Signaling & Behavior 2:1, 4-7; Jan./Feb. 2007.
Regente et al. Vesicular fractions of sunflower apoplastic fluids are associated with potential exosome marker proteins, Available online Sep. 29, 2009.
Roger E, Lagarce F, Garcion E, Benoit JP. Lipid nanocarriers improve paclitaxel transport throughout human intestinal epithelial cells by using vesicle-mediated transcytosis. J Control Release. 2009;140(2):174-181. Prepublished on Aug. 25, 2009 as DOI 80168-3659(09)00548-3 [pii]10.1016/j.jconrel.2009.08.010.
Setser, C.S., Racetie, W.L. Macromolecule replacers in food products. Crit Rev Food Sci Nutr 1992;32:275-97.
Sheikh, S.Z., Hegazi, R.A., Kobayashi, T. et al. An Anti-Inflammatory Role for Carbon Monoxide and Heme Oxygenase-1 in Chronic Th2-Mediated Murine Colitis. The Journal of Immunology 2011 ;186:5506-5513.
Song Z, Feng R, Sun M, Guo C, Gao Y, Li L et al. Curcumin-loaded PLGA-PEG-PLGA triblock copolymeric micelles: Preparation, pharmacokinetics and distribution in vivo. Journal of colloid and interface science 2011;354 1):116-23.
Spilman, M. S., Welbon, C., Nelson, E. & Dokland, T. Cryo-electron tomography of porcine reproductive and respiratory syndrome virus: organization of the nucleocapsid. J Gen Virol 90, 527-535, doi:10.1099/vir.0.007674-0 (2009).
Sun et al. "A novel nanoparticle drug delivery system: the anti-inflammatory activity of curcumin is enhanced when encapsulated in exosomes," Mol Ther, 2010, vol. 18, pp. 1606-1614.
Taheri, A , Atyabi, F., Salman Nouri, F. et al. Nanoparticles of Conjugated Methotrexate-Human Serum Albumin: Preparation and Cytotoxicity Evaluations. Journal of Nanomaterials 2011 ;2011.
Thery C, Ostrowski M, Segura E. Membrane vesicles as conveyors of immune responses. Nature reviews Immunology. 2009;9(8):581-593. Prepublished on Jun. 6, 2009 as DOI 10.1038/nri2567.
United States Patent and Trademark Office, International Search Report and Written Opinion issued in corresponding Application No. PCT/US15/25337, dated Jul. 1, 2015.
United States Patent and Trademark Office, International Search Report and Written Opinion issued in corresponding Application No. PCT/US16/040710, dated Sep. 23, 2016.
USPTO/ISA, International Search Report and Written Opinion in corresponding international application PCT/ US2011/023747, completed Mar. 22, 2011.
Valadi H, Ekstrom K, Bossios A, Sjostrand M, Lee J J and Lotvall J O. Exosome-mediated transfer of mRNAs and microRNAs is a novel mechanism of genetic exchange between cells. Nature cell biology. 2007; 9(6):654-659.
Valenti et al. "Human tumor-released microvesicles promote the differentiation of myeloid cells with transforming growth factor-beta-mediated suppressive activity on T lymphocytes," Cancer Res, 2006, vol. 66(18), pp. 9290-9298.
Vickers K C, Palmisano B T, Shoucri B M, Shamburek R D and Remaley A T. MicroRNAs are transported in plasma and delivered to recipient cells by high-density lipoproteins. Nature cell biology. 2011; 13(4):423-433.
Wang et al. "Thymus exosomes-like particles induce regulatory T cells," J_ Immunol., 2008, vol. 181(8), pp. 5242-5248.
Wang, S. & Low, P. S. Folate-mediated targeting of antineoplastic drugs, imaging agents, and nucleic acids to cancer cells. J Control Release 53, 39-48 (1998).

(56) References Cited

OTHER PUBLICATIONS

Xiang et al. "Induction of myeloid-derived suppressor cells by tumor exosomes," Int J_ Cancer, 2009, vol. 124(11),pp. 2621-2633.
Xiang X, Zhuang X, Ju S, Zhang S, Jiang H, Mu J, Zhang L, Miller D, Grizzle W and Zhang H G. miR-155 promotes macroscopic tumor formation yet inhibits tumor dissemination from mammary fat pads to the lung by preventing EMT. Oncogene. 2011; 30(31):3440-3453.
Xiao, S. et al. Overexpression of *Arabidopsis* acyl-CoA binding protein ACBP3 promotes starvation-induced and age-dependent leaf senescence. Plant Cell 22, 1463-1482, doi:10.1105/tpc.110. 075333 (2010).
Xue et al., Solid lipid-PEI hybrid nanocarrier: An integrated approach to provide extended, targeted, and safer siRNA therapy of prostate cancer in an all-in-one manner, ACS Nano, vol. 5, pp. 7034-7047. (Year: 2011).
Yagi et al. "A nanoparticle system specifically designed to deliver short interfering RNA inhibits tumor growth in vivo," Cancer Res, 2009, vol. 69(16), pp. 6531-6538.
Yin L, Ding J, He C, Cui L, Tang C, Yin C. Drug permeability and mucoadhesion properties of thiolated trimethyl chitosan nanoparticles in oral insulin delivery. Biomaterials. 2009;30(29):5691-5700. Prepublished on Jul. 21, 2009 as DOI 80142-9612(09)00680-2 [pii]10.1016/j.biomaterials.2009.06.055.
Yu S, Liu C, Su K et al. Tumor exosomes inhibit differentiation of bone marrow dendritic cells_ J Immunol. 2007;178 (11):6867-6875.
Zhang XC, Chen J, Su CH, Yang HY, Lee MH. Roles for CSN5 in control of p53/MDM2 activities. J Cell Biochem. 2008;103(4):1219-1230. Prepublished on Sep. 21, 2007 as DOI 10.1002/jcb.21504.
Zhang, H. G. et al. Antigen presenting cells expressing Fas ligand down-modulate chronic inflammatory disease in Fas ligand-deficient mice. J Clin Invest 105, 813-821, doi:10.1172/JCI8236 {2000).
Zhuang, X. et al. Treatment of Brain Inflammatory Diseases by Delivering Exosome Enscapsulated Anti-inflammatory Drugs From the Nasal Region to the Brain. Mol Ther 19, 1769-1779, doi:10. 1038/mt.2011.164 (2011).
Zoller, Tetraspanins: push and pull in suppressing and promoting metastasis, Nature Reviews: vol. 9, Jan. 2009; p. 40-55.
Examination Report for AU Patent Application No. 2016288643 dated Jul. 1, 2021.
Examination Report for IN Patent Application No. 201817004051 dated Nov. 25, 2021.
Liu et al. (2016) "The Host Shapes the Gut Microbiota via Fecal MicroRNA," Cell Host & Microbe, vol. 19, pp. 32-43.
Office Action corresponding with Chinese Patent Application No. 201680049762.8 dated Jul. 1, 2021.
Office Action corresponding with European Patent Application No. 16818891.0 dated Oct. 4, 2021.
Office Action (Restriction Requirement) corresponding to U.S. Appl. No. 16/816,214 dated Sep. 28, 2021.
Office Action corresponding to U.S. Appl. No. 17/050,200 dated Feb. 17, 2022.
Office Action corresponding to U.S. Appl. No. 16/359,618 dated Feb. 10, 2022.
Office Action corresponding to U.S. Appl. No. 16/377,800 dated Aug. 18, 2021.
Office Action (Restriction Requirement) corresponding to U.S. Appl. No. 16/462,715 dated Nov. 20, 2020.
Office Action corresponding to U.S. Appl. No. 16/462,715 dated Dec. 27, 2021.
Teng et al. 2018 "Plant-Derived Exosomal MicroRNAs Shape the Gut Microbiota," Cell Host & Microbe, vol. 24, pp. 637-652 plus Methods Addendum, pp. e1-e8; specifically p. 637, 639, and e3.
Deng et al. "Exosomes miR-126a Released 1-1 from MDSC Induced by DOX Treatment Promotes Lung Metastasis," Oncogene, 2017, vol. 36, No. 5, pp. 639-651.
Extended European Search Report corresponding to EP Patent Application No. 19793847.5 dated Apr. 8, 2022 (8 pgs.).

Office Action corresponding to U.S. Appl. No. 16/816,214 dated May 13, 2022.
Office Action (Restriction Requirement) corresponding to U.S. Appl. No. 16/766,055 dated Jun. 30, 2022.
Aftab et al. (2020) "Analysis of SARS-CoV-2 RNA-dependent RNA polymerase as a potential therapeutic drug target using a computational approach.," J Transl Med 18:275.
Arienti et al. (2019) "Regulation of Apoptotic Cell Clearance During Resolution of Inflammation,". Front Pharmacol 10:891; 12 Pages.
Baier et al. "MicroRNAs Are Absorbed in Biologically Meaningful Amounts from Nutritionally Relevant Doses of Cow Milk and Affect Gene Expression in Peripheral Blood Mononuclear Cells, HEK-293 Kidney Cell Cultures, and Mouse Livers," The Journal of Nutrition, 2014, vol. 144, No. 10, pp. 1495-1500.
Examination Report for CA Patent Application No. 3,029,602 dated Aug. 26, 2022.
Godoy et al. (2018) "Large Differences in Small RNA Composition Between Human Biofluids," Cell Rep 25:pp. 1346-1358.
International Preliminary Report corresponding to International Patent Application Serial No. PCT/US 2021/033913 dated Nov. 17, 2022.
International Search Report and Written Opinion corresponding to International Patent Application Serial No. PCT/US2021/033913 dated Oct. 6, 2021.
Ionescu et al. "The Interplay Between Gut Microbiota and miRNAs in Cardiovascular Diseases," Frontiers in Cardiovascular Medicine, 2022, vol. 9, Art. 856901, pp. 1-14.
Lee et al. (2018) "Extracellular Vesicle: An Emerging Mediator of Intercellular Crosstalk in Lung Inflammation and Injury.," Front Immunol vol. 9: article 92; 8 Pages.
Masvekar et al. (2019) "Quantifications of CSF Apoptotic Bodies Do Not Provide Clinical Value in Multiple Sclerosis," Front Neurol 10, 1241, doi:10.3389/fneur.2019.01241. 11 Pages.
Miura (2019) "Respiratory epithelial cells as master communicators during viral infections,". Curr Clin Mi crobi ol Rep 6: pp. 10-17.
Miyamoto et al. (2010) "Inhibitor ofIkappaB kinase activity, BAY 11-7082, interferes with interferon regulatory factor 7 nuclear translocation and type I interferon production by plasmacytoid dendritic cells.," Arthritis Res Ther 12:R87.13 Pages.
Mukhamedova et al. (2019) "Exosomes containing HIV protein Nef reorganize lipid rafts potentiating inflammatory response in bystander cells.," PLoS Pathogens 15:el007907.30 Pages.
Murphy et al. (2008) Suppression of immediate-early viral gene expression by herpesviruscoded microRNAs: implications for latency. Proceedings of the National Academy of Sciences USA 105: pp. 5453-5458.
Nahand et al. (2020) "Exosomal miRNAs: novel players in viral infection.," Epigenomics 12: pp. 353-370.
Office Action corresponding to European Patent Application No. 16818891.0 dated Mar. 23, 2023.
Office Action corresponding to U.S. Appl. No. 16/377,800 dated Apr. 24, 2023.
Office Action corresponding to U.S. Appl. No. 16/462,715 dated Aug. 2, 2022.
Office Action corresponding to U.S. Appl. No. 16/462,715 dated Apr. 4, 2023.
Office Action corresponding to U.S. Appl. No. 16/766,055 dated Dec. 2, 2022.
Pastuzyn et al. (2018) "The Neuronal Gene Arc Encodes a Repurposed Retrotransposon Gag Protein that Mediates Intercellular RNA Transfer.," Cell 172: pp. 275-288.
Raab-Traub & Dittmer (2017) "Viral effects on the content and function of extracellular vesicles.," Nature Reviews Microbiology 15:pp. 559-572.
Robinson & Oshlack (2010) "A scaling normalization method for differential expression analysis of RNA-seq data," Genome Biology 11: 9 pages.
Sampey et al. (2016) "Exosomes from HIV-I-infected Cells Stimulate Production of Pro-inflammatory Cytokines through Trans-activating Response (TAR) RNA," The Journal of Biological Chemistry 291:pp. 1251-1266.

(56) References Cited

OTHER PUBLICATIONS

Santiana et al. (2018) "Vesicle-Cloaked Virus Clusters Are Optimal Units for Interorganismal Viral Transmission.," Cell Host & Microbe 24:pp. 208-220.
Sundaram et al. (2019) "Plant-Derived Exosomal Nanoparticles Inhibit Pathogenicity of Porphyromonas gingivalis,". iScience 21 :pp. 308-327.
Teng et al. (2016) "Grapefruit-derived nanovectors deliver miR-18a for treatment of liver metastasis of colon cancer by induction of MI macrophages,". Oncotarget 7: pp. 25683-25697.
Teng et al. (2017) "MVP-mediated exosomal sorting of miR-193a promotes colon cancer progression,". Nat Commun 8:14448; 16 Pages.
Velandia-Romero et al. (2020) "Extracellular vesicles ofU937 macrophage cell line infected with DENV-2 induce activation in endothelial cells," EA.hy926. PloS One 15:e0227030.25 pages.
Xiao et al. (2018) "Identification of exosome-like nanoparticle-derived microRNAs from 11 edible fruits and vegetables.," PeerJ 6:e5186. 19 Pages.
Zhang et al. (2008) "Inhibition of the tumor necrosis factor-alpha pathway is radioprotective for the lung.," Clin Cancer Res 14: pp. 1868-1876.

\* cited by examiner

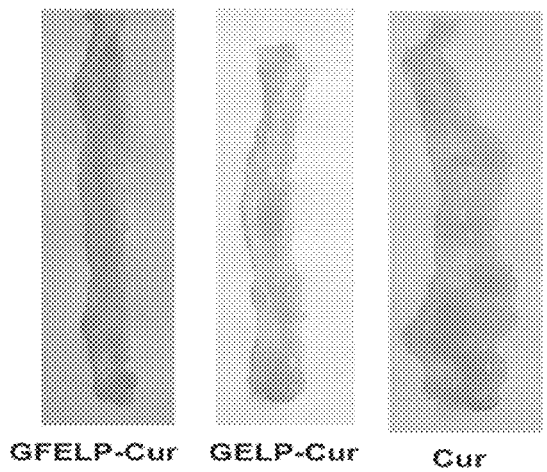
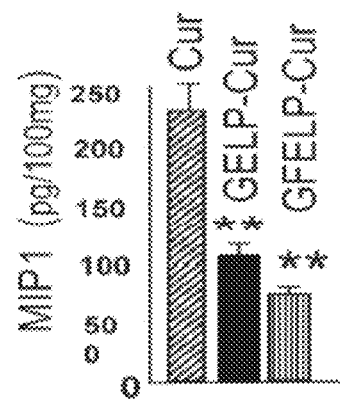
FIG. 5A  FIG. 5B
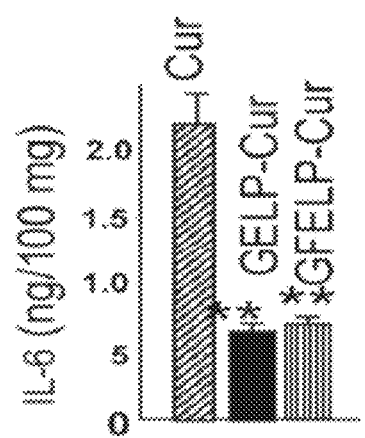
FIG. 5C

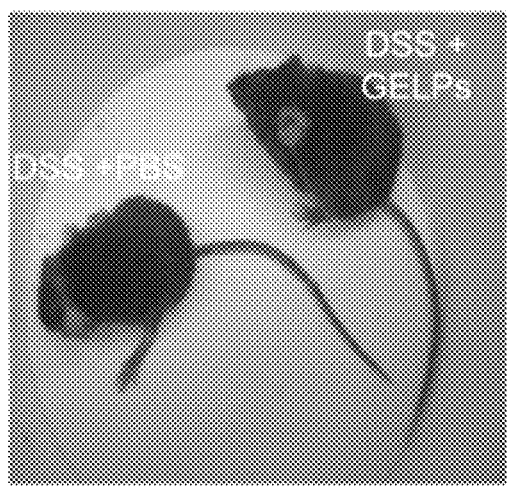 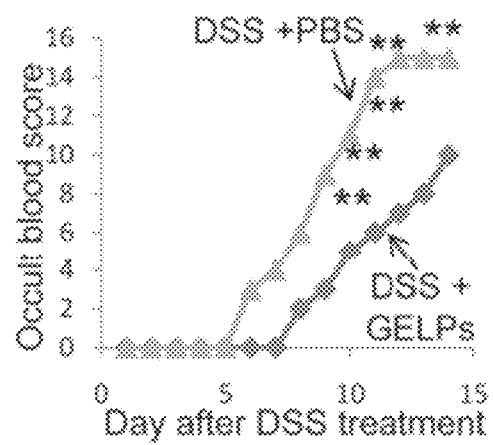
FIG. 6A                    FIG. 6B

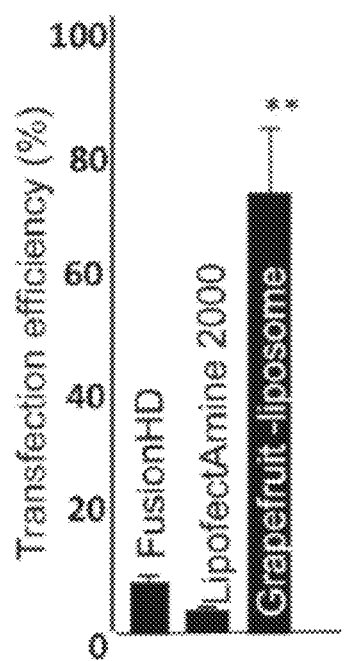 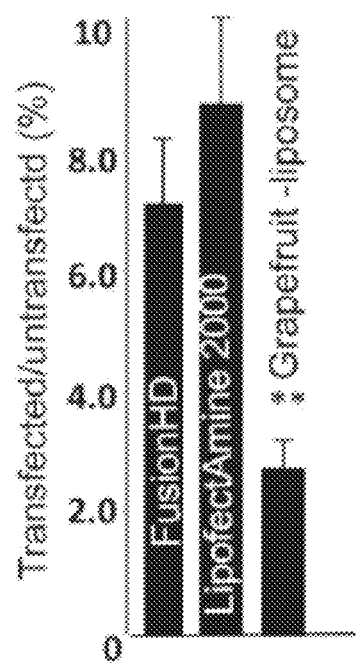
FIG. 12C           FIG. 12D

EDIBLE PLANT-DERIVED MICROVESICLE COMPOSITIONS FOR DIAGNOSIS AND TREATMENT OF DISEASE

RELATED APPLICATIONS

This application is a continuation of U.S. patent application Ser. No. 14/356,853 (pending), filed May 7, 2014, which itself is a U.S. National Stage application of PCT International Patent Application Serial No. PCT/US2012/056298 filed Sep. 20, 2012, which itself claims priority from U.S. Provisional Application Ser. No. 61/556,565, filed Nov. 7, 2011. The entire disclosure of each of these applications is incorporated herein by this reference.

TECHNICAL FIELD

The presently-disclosed subject matter relates to edible plant-derived microvesicle compositions and methods of using the same for the diagnosis and treatment of disease. In particular, the presently-disclosed subject matter relates to compositions that include therapeutic agents encapsulated by edible plant-derived microvesicles and that are useful in the diagnosis and treatment of disease.

BACKGROUND

Microvesicles are small assemblies of lipid molecules (50-1000 nm in size), which include, but are not limited to, exosomes, epididimosomes, argosomes, exosome-like vesicles, microparticles, promininosomes, prostasomes, dexosomes, texosomes, dex, tex, archeosomes, and oncosomes. Microvesicles can be formed by a variety of processes, including the release of apoptotic bodies, the budding of microvesicles directly from the cytoplasmic membrane of a cell, and exocytosis from multivesicular bodies. For example, exosomes are commonly formed by their secretion from the endosomal membrane compartments of cells as a consequence of fusion of multivesicular bodies with the plasma membrane. The MVBs are formed by inward budding from the endosomal membrane and subsequent pinching off of small vesicles into the luminal space. The internal vesicles present in the MVBs are then released into the extracellular fluid as so-called exosomes.

In addition to being formed by a variety of processes, microvesicles are produced by a variety of eukaryotic cells, including plant cells, and the release and uptake of these secreted membrane vesicles has been shown to allow for the transfer of small packages of information (bioactive molecules) to numerous target cells. Indeed, the contents of these packages are enriched in proteins, lipids, and microRNAs, and recent biological and proteomic studies of microvesicles have further revealed the biological functions of microvesicles. From these studies, it appears that one of the major roles of microvesicles is the exchange of information through their secretion, with the functional consequences of such membrane transfers including the induction, amplification and/or modulation of recipient cell function. In this regard, a number of studies have led to the idea that microvesicles are a common mode of intercellular communication.

Despite the number of studies linking microvesicles to intracellular communication, however, to date, the use of microvesicles as an efficient and effective delivery vehicle has yet to be fully realized due, at least in part, to the inability to produce the large quantities of microvesicles that are needed for therapeutic applications and to the inability to effectively and efficiently utilize the microvesicles to deliver a therapeutic agent to target cells and tissues, while also retaining the biological activity of the therapeutic agents.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes microvesicle compositions and methods of using the microvesicle compositions for the diagnosis and treatment of disease. More specifically, the presently-disclosed subject matter relates to microvesicle compositions that include one or more therapeutic agents encapsulated by an edible plant-derived microvesicle and that are useful in the diagnosis and treatment of disease.

In some embodiments of the presently-disclosed subject matter, a composition is provided that includes a therapeutic agent encapsulated by an edible-plant derived microvesicle. In some embodiments, the edible plant is a fruit, such as, in some embodiments, a grape, a grapefruit, or a tomato.

In some embodiments, a microvesicle composition is provided where the therapeutic agent is selected from a phytochemical agent, a stat3 inhibitor, and a chemotherapeutic agent. In some embodiments, the therapeutic agent is a phytochemical agent, such as, in some embodiments, curcumin. In some embodiments, the therapeutic agent is a phytochemical agent selected from curcumin, resveratrol, baicalein, equol, fisetin, and quercetin. In other embodiments, the therapeutic agent is a Stat3 inhibitor, such as JSI-124. In further embodiments, the therapeutic agent is a chemotherapeutic agent that, in certain embodiments, is selected from the group consisting of retinoic acid, 5-fluorouracil, vincristine, actinomycin D, adriamycin, cisplatin, docetaxel, doxorubicin, and taxol.

In yet further embodiments of the compositions of the presently-disclosed subject matter, the therapeutic agent comprises a nucleic acid molecule selected from a siRNA, a microRNA, and a mammalian expression vector. In some embodiments, the microvesicle composition is in the form of a pharmaceutical composition where the edible-plant derived microvesicle encapsulating the therapeutic agent is further combined with a pharmaceutically-acceptable vehicle, carrier, or excipient.

Further provided, in some embodiments of the presently-disclosed subject matter, are methods for treating an inflammatory disorder. In some embodiments, a method for treating an inflammatory disorder is provided that comprises administering to a subject in need thereof an effective amount of a composition that includes a therapeutic agent encapsulated by an edible plant-derived microvesicle. In some embodiments, the composition is administered orally or intranasally. In some embodiments, administering the edible-plant derived microvesicle composition reduces an amount of an inflammatory cytokine in a subject, including, in some embodiments, a reduction in an amount of tumor necrosis factor-α, interleukin-1β, interferon-γ, or interleukin-6.

In some embodiments of the presently-disclosed methods of treating an inflammatory disorder, the inflammatory disorder is selected from sepsis, septic shock, colitis, colon cancer, and arthritis. In some embodiments, the inflammatory disorder is colitis, where, in certain embodiments, administering the composition increases an amount of intestinal epithelial cell proliferation in a subject or increases an amount of Wnt-f3-catenin signaling in the intestine of a subject to thereby treat the colitis.

Still further provided, in some embodiments of the presently-disclosed subject matter, are methods for treating a cancer. In some embodiments, a method for treating a cancer in a subject is provided that comprises administering to a subject an effective amount of a composition including a therapeutic agent encapsulated by a microvesicle, where the microvesicle is derived from an edible plant. In some embodiments, the therapeutic agent encapsulated by the edible-plant derived microvesicle is selected from a phytochemical agent, a stat3 inhibitor, and a chemotherapeutic agent. In some embodiments, the microvesicles of the present compositions comprise a cancer targeting moiety for directing the composition to a cancer cell. In some embodiments, the cancer targeting moiety comprises folic acid.

In some embodiments of the methods for treating a cancer disclosed herein, the methods are used to treat a brain cancer, a breast cancer, a lung cancer, or a colon cancer. In some embodiments, the cancer is a brain cancer that, in some embodiments, comprises a glioma. In some embodiments, the microvesicle compositions of the presently-disclosed subject matter are used to treat the cancer by administering the microvesicle compositions intranasally, orally, or intratumorally.

Still further provided, in some embodiments of the presently-disclosed subject matter, are methods for diagnosing a colon cancer. In some embodiments, a method for diagnosing a colon cancer in a subject is provided that includes the steps of: administering an effective amount of a composition that includes an edible plant-derived microvesicle incorporating a detectable label; determining an amount of the detectable label in an intestine of the subject; and comparing the amount of the detectable label, if present, to a control level of the detectable label, such that the subject is then diagnosed as having colon cancer or a risk thereof if there is a measurable difference in the amount of the detectable label as compared to the control level. In some embodiments, the subject has colon cancer. In some embodiments, based on the determined amounts of detectable label, a treatment is further selected or modified. In some embodiments, the detectable label comprises a radioisotope or a fluorescent probe.

Further advantages of the presently-disclosed subject matter will become evident to those of ordinary skill in the art after a study of the description, Figures, and non-limiting Examples in this document.

BRIEF DESCRIPTION OF THE DRAWINGS

(FIG. 3A), where after ultracentrifugation for 1.5 h, the GELP-Cur complex observed in the sucrose gradient (top of panel) was examined by electromicroscopy (bottom of panel); graphs showing the concentration of TNF-α (FIG. 3B) and IL-6 (FIG. 3C) in sera of mice twenty days after DBA/1j mice were immunized with collagen II, where mice were orally administered, every other day for 20 days, GELP-Cur complex (4.0 mg/kg of curcumin encapsulated), GELP at an equal amount used in GELP-Cur, free curcumin (4.0 mg/kg), or PBS, and where blood was taken immediately before or 1 h after treatments on days 1, 10, and 20; and graphs showing the levels of TNF-α (FIG. 3D) and IL-6 (FIG. 3E) in supernatants of cell cultures of anticoagulated whole blood from the same mice as in FIGS. 3B and 3C; and a graph showing the correlation between the induction of IL-6 in the sera and the amount of CD14$^+$PI$^+$AnnexinV$^+$ cells in the peripheral blood of mice collected at day 1 after the foregoing treatments and analyzed using a Spearman's rank test (FIG. 3F);

FIGS. 5A-5C includes images and graphs showing the reduction of AOM induced colon cancer in mice treated as described in FIG. 4, including: an image of representative excised colons from mice treated with GFELP-cur, GELP-cur and free Cur (FIG. 5A); and an enzyme-linked immunosorbent assay (ELISA) analysis of the levels of MIP1 (FIG. 5B) and IL-6 (FIG. 5C) produced from the colon tissue of treated mice;

FIGS. 6A-6H include images and graphs showing the ability of GELPs to protect mice against DSS induced colitis, including: an image showing C57BL/6 mice who were either provided 3.0% DSS in the drinking water over the course of 7 days and developed severe colitis symptoms with intense depression (DSS+PBS) or were fed GELPs (DSS+GELPs) and exhibited no visible symptoms (FIG. 6A); a graph showing the incidence of occult blood in fecal samples of DSS+PBS mice or DSS+GELPs mice as a function of the number of days after DSS treatment (FIG. 6B); graphs showing the survival (FIG. 6C) and representative colon length (FIG. 6D) in the mice administered DSS+PBS or DSS+GELPs; images and a graph showing the quantification of the villus length from the base of the villus to the villus apex of GELP and PBS gavaged mice administered DSS (FIG. 6E); a graph showing the flux of 4-KDa FITC-dextran across colonic tissues in the mice administered DSS (FIG. 6F); a graph showing the sera levels of IL-6 and IL-1β (FIG. 6G) in the mice administered DSS; and a graph showing the amount of bacteria in the liver of the mice administered DSS (FIG. 6H);

FIGS. 12A-12D include images and graphs showing the transfection efficiency of grapefruit liposome as a nucleic acid delivery vehicle, including: images showing the expression of green fluorescent protein (GFP) in B6 spleen T cells using the transfection agents Fusion HD, LIPOFECTAMINE® 2000 (Invitrogen, Carlsbad, CA), and grapefruit liposome (FIG. 12A); graphs showing representative FACS of GFP positive cells (FIG. 12B), and graphs showing the transfection efficiency percentages (FIG. 12C) or the percent of transfected and untransfected cells (FIG. 12D) as a function of the various delivery vehicles;

DESCRIPTION OF EXEMPLARY EMBODIMENTS

Figure 1A:
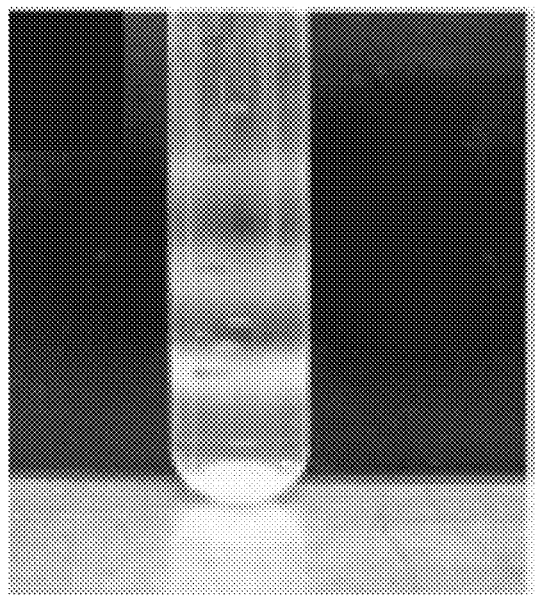
FIGS. 1A-1D are photographs showing the results of sucrose gradient differential centrifugation procedures used to isolate exosomes from grapes and grapefruits, including: a photograph of banded exosomes after sucrose gradient centrifugation (FIG. 1A, middle band); electron microscopy photographs confirming the presence of grape-derived exosome-like particles (GELPs, FIG. 1B) and grapefruit-derived exosome-like particles (GFELPs, FIG. 1C); and a photograph showing the results of an SDS-PAGE analysis of the GELPs and GFELPs, where 100 mg of GELP, GFELP or TS/A exospore proteins were run on a 10% SDS PAGE (FIG. 1D)

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Microvesicles are naturally existing nanoparticles that are in the form of small assemblies of lipid particles, are about 50 to 1000 nm in size, and are not only secreted by many types of in vitro cell cultures and in vivo cells, but are commonly found in vivo in body fluids, such as blood, urine and malignant ascites. Indeed, microvesicles include, but are not limited to, particles such as exosomes, epididimosomes, argosomes, exosome-like vesicles, microparticles, promininosomes, prostasomes, dexosomes, texosomes, dex, tex, archeosomes, and oncosomes.

As noted above, microvesicles can be formed by a variety of processes, including the release of apoptotic bodies, the budding of microvesicles directly from the cytoplasmic membrane of a cell, and exocytosis from multivesicular bodies. For example, exosomes are commonly formed by their secretion from the endosomal membrane compartments of cells as a consequence of the fusion of multivesicular bodies with the plasma membrane. The multivesicular bodies are formed by inward budding from the endosomal membrane and subsequent pinching off of small vesicles into the luminal space. The internal vesicles present in the MVBs are then released into the extracellular fluid as so-called exosomes.

As part of the formation and release of microvesicles, unwanted molecules are eliminated from cells. However, cytosolic and plasma membrane proteins are also incorporated during these processes into the microvesicles, resulting in microvesicles having particle size properties, lipid bilayer functional properties, and other unique functional properties that allow the microvesicles to potentially function as effective nanoparticle carriers of therapeutic agents. In this regard, the term "microvesicle" is used interchangeably herein with the terms "nanoparticle," "liposome," "exosome," "exosome-like particle," "nano-vector" and grammatical variations of each of the foregoing. It has now been discovered though that edible plants, such as fruits, are not only a viable source of large quantities of microvesicles, but that microvesicles derived from edible plants can be used as a effective delivery vehicle for a number of therapeutic agents, while also retaining the biological activity of the therapeutic agents.

The presently-disclosed subject matter thus includes edible plant-derived microvesicle compositions that further include therapeutic agents and are useful in the treatment of various diseases, including inflammatory disorders and cancers. In some embodiments of the presently-disclosed subject matter, a microvesicle composition is provided that comprises a therapeutic agent encapsulated by an microvesicle, wherein the microvesicle is derived from an edible plant. In some embodiments, the therapeutic agent encapsulated by the edible-plant derived microvesicle is selected from a phytochemical agent, a stat3 inhibitor, and a chemotherapeutic agent.

The term "edible plant" is used herein to describe organisms from the kingdom Plantae that are capable of producing their own food, at least in part, from inorganic matter through photosynthesis, and that are fit for consumption by a subject, as defined herein below. Such edible plants include, but are not limited to, vegetables, fruits, nuts, and the like. In some embodiments of the microvesicle compositions described herein, the edible plant is a fruit. In some embodiments, the fruit is selected from a grape, a grapefruit, and a tomato.

The phrase "derived from an edible plant," when used in the context of a microvesicle derived from an edible plant, refers to a microvesicle that, by the hand of man, exists apart from its native environment and is therefore not a product of nature. In this regard, in some embodiments, the phrase "derived from an edible plant" can be used interchangeably with the phrase "isolated from an edible plant" to describe a microvesicle of the presently-disclosed subject matter that is useful for encapsulating therapeutic agents.

The phrase "encapsulated by a microvesicle," or grammatical variations thereof is used herein to refer to microvesicles whose lipid bilayer surrounds a therapeutic agent. For example, a reference to "microvesicle curcumin" refers to an microvesicle whose lipid bilayer encapsulates or surrounds an effective amount of curcumin. In some embodiments, the encapsulation of various therapeutic agents within microvesicles can be achieved by first mixing the one or more of the phytochemical agents, Stat3 inhibitors, or chemotherapeutic agents with isolated microvesicles in a suitable buffered solution, such as phosphate-buffered saline (PBS). After a period of incubation sufficient to allow the therapeutic agent to become encapsulated during the incubation period, the microvesicle/therapeutic agent mixture is then subjected to a sucrose gradient (e.g., and 8, 30, 45, and 60% sucrose gradient) to separate the free therapeutic agent and free microvesicles from the therapeutic agents encapsulated within the microvesicles, and a centrifugation step to isolate the microvesicles encapsulating the therapeutic agents. After this centrifugation step, the microvesicles including the therapeutic agents are seen as a band in the sucrose gradient such that they can then be collected, washed, and dissolved in a suitable solution for use as described herein below.

As noted, in some embodiments, the therapeutic agent is a phytochemical agent. As used herein, the term "phytochemical agent" refers to a non-nutritive plant-derived compound, or an analog thereof. Examples of phytochemical agents include, but are not limited to compounds such as monophenols; flavonoids, such as flavonols, flavanones, flavones, flavan-3-ols, anthocyanins, anthocyanidins, isoflavones, dihydroflavonols, chalcones, and coumestans; phenolic acids; hydroxycinnamic acids; lignans; tyrosol esters; stillbenoids; hydrolysable tannins; carotenoids, such as carotenes and xanthophylls; monoterpenes; saponins; lipids, such as phytosterols, tocopherols, and omega-3,6,9 fatty acids; diterpenes; triterpinoids; betalains, such as betacyanins and betaxanthins; dithiolthiones; thiosulphonates; indoles; and glucosinolates. As another example of a phytochemical agent disclosed herein, the phytochemical agent can be an analog of a plant-derived compound, such as oltipraz, which is an analog of 1,2-dithiol-3-thione, a compound that is found in many cruciferous vegetables.

In some embodiments of the presently-disclosed subject matter, the therapeutic agent is a phytochemical agent selected from curcumin, resveratrol, baicalein, fisetin, and quercetin. In some embodiments, the phytochemical agent is curcumin. Curcumin is a pleiotropic natural polyphenol with anti-inflammatory, anti-neoplastic, anti-oxidant and chemopreventive activity, with these activities having been identified at both the protein and molecular levels. Nevertheless, limited progress has been reported with respect to the therapeutic use of curcumin as curcumin is insoluble in aqueous solvents and is relatively unstable. In addition, curcumin is known to have a low systemic bioavailability after oral dosing, which further limits its usage and clinical efficacy. It has been determined, however, that by encapsulating curcumin in edible plant derived microvesicle, not only can the solubility of curcumin be increased, but the encapsulation of the curcumin within the microvesicles protects the curcumin from degradation and also increases the bioavailability of the microvesicle curcumin.

As also noted herein above, in some embodiments of the presently-disclosed subject matter, the therapeutic agent that is encapsulated within the exosome is a chemotherapeutic agent. Examples of chemotherapeutic agents that can be used in accordance with the presently-disclosed subject matter include, but are not limited to, platinum coordination compounds such as cisplatin, carboplatin or oxalyplatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE® (Millennium Pharmaceuticals, Cambridge, MA); or YONDELIS (Johnson & Johnson, New Brunswick, NJ). In some embodiments, the chemotherapeutic agent that is encapsulated by an exosome in accordance with the presently-disclosed subject matter is selected from retinoic acid, 5-fluorouracil, vincristine, actinomycin D, adriamycin, cisplatin, docetaxel, doxorubicin, and taxol.

As further noted, in some embodiments, the therapeutic agent is a signal transducer and activator of transcription 3 (Stat3) inhibitor. "Stat3" or "Signal Transducer and Activator of Transcription 3" is a transcription factor encoded by the STAT3 gene and, in response to cytokines or growth factors, is known to become phosphorylated and to then translocate to the nucleus of cells where it mediates the expression of a variety of genes in response to various stimuli, and thus plays a role in a number of cellular processes including cell growth and apoptosis. In this regard, the term "Stat3 inhibitor" is used herein to refer to any chemical compound or protein that prevents or otherwise reduces the activity of Stat3 including, but not limited to, chemical compounds or proteins that prevent or reduce the transcriptional activity of Stat3, and chemical compounds or proteins that prevent or reduce the activation of Stat3 by preventing its activation (e.g., the phosphorylation and/or translocation of Stat3 to the nucleus of a cell). A number of Stat3 inhibitors are known to those skilled in the art including, but not limited to, the PIAS3 protein, Stattin, or JSI-124, which is also referred to as curcurbitacin I. In some embodiments of the presently-disclosed subject matter, the Stat3 inhibitor that is encapsulated within the edible plant-derived microvesicles is JSI-124.

In other embodiments of the presently-disclosed subject matter, therapeutic agents included within the microvesicle compositions comprises nucleic acid molecules selected from a siRNA, a microRNA, and an expression vector, such as a mammalian expression vector. The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) Nucleic Acid Res 19:5081; Ohtsuka et al. (1985) J Biol Chem 260:2605-2608; Rossolini et al. (1994) Mol Cell Probes 8:91-98). The terms "nucleic acid" or "nucleic acid sequence" can also be used interchangeably with gene, open reading frame (ORF), cDNA, mRNA, siRNA, microRNA, and the like.

The terms "small interfering RNA," "short interfering RNA," "small hairpin RNA," "siRNA," and "shRNA" are used interchangeably herein to refer to any nucleic acid molecule capable of mediating RNA interference (RNAi) or gene silencing. See, e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA can comprise a double stranded polynucleotide molecule comprising complementary sense and antisense regions, wherein the antisense region comprises a sequence complementary to a region of a target nucleic acid molecule. In another embodiment, the siRNA can comprise a single stranded polynucleotide having self-complementary sense and antisense regions, wherein the antisense region comprises a sequence complementary to a region of a target nucleic acid molecule. In yet another embodiment, the siRNA can comprise a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

MicroRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression. There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

In some embodiments, the nucleic acid molecules that are encapsulated or otherwise incorporated into a microvesicle composition of the presently-disclosed subject matter are included in the microvesicles are part of an expression vector. The term "expression vector" is used interchangeably herein with the terms "expression cassette" and "expression control sequence," and is used to refer to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression vector comprising the nucleotide sequence of interest can be chimeric, meaning that at least one of its components is heterologous with respect to at least one of its other components. The expression vector can also be one that is naturally occurring but has been obtained in a recombinant form useful for heterologous expression. In some embodiments, the expression vector is a mammalian expression vector that is capable of directing expression of a particular nucleic acid sequence of interest in a mammalian cell.

In some embodiments of the presently disclosed subject matter, a pharmaceutical composition is provided that comprises an edible plant-derived microvesicle composition disclosed herein and a pharmaceutical vehicle, carrier, or excipient. In some embodiments, the pharmaceutical composition is pharmaceutically-acceptable in humans. Also, as described further below, in some embodiments, the pharmaceutical composition can be formulated as a therapeutic composition for delivery to a subject.

A pharmaceutical composition as described herein preferably comprises a composition that includes pharmaceutical carrier such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the microvesicle compositions of the presently-disclosed subject matter can also be formulated as rectal compositions, such as suppositories or retention enemas, e.g., containing conventional suppository bases such as cocoa butter or other glycerides. Further, the exosomal compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

Further provided, in some embodiments of the presently-disclosed subject matter, are methods for treating an inflammatory disorder or a cancer. In some embodiments, a method for treating an inflammatory disorder is provided that comprises administering to a subject in need thereof an effective amount of a microvesicle composition of the presently-disclosed subject matter, wherein the microvesicle included in the composition is derived from an edible plant, such as a fruit.

As used herein, the terms "treatment" or "treating" relate to any treatment of a condition of interest (e.g., an inflammatory disorder or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to atherosclerosis; arthritis; inflammation-promoted cancers; asthma; autoimmune uveitis; adoptive immune response; dermatitis; multiple sclerosis; diabetic complications; osteoporosis; Alzheimer's disease; cerebral malaria; hemorrhagic fever; autoimmune disorders; and inflammatory bowel disease. In some embodiments, the inflammatory disorder is selected from the group consisting of sepsis, septic shock, colitis, colon cancer, and arthritis.

For administration of a therapeutic composition as disclosed herein (e.g., an edible plant-derived microvesicle encapsulating a therapeutic agent), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082).

Regardless of the route of administration, the compositions of the presently-disclosed subject matter are typically administered in amount effective to achieve the desired response. As such, the term "effective amount" is used herein to refer to an amount of the therapeutic composition (e.g., a microvesicle encapsulating a therapeutic agent, and a pharmaceutically vehicle, carrier, or excipient) sufficient to produce a measurable biological response (e.g., a decrease in inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

In some embodiments of the therapeutic methods disclosed herein, administering an edible plant-derived microvesicle composition of the presently-disclosed subject matter reduces an amount of an inflammatory cytokine in a subject. In some embodiments, the inflammatory cytokine can be interleukin-1β (IL-1β), tumor necrosis factor-alpha (TNF-α), interferon-γ (IFN-γ), or interleukin-6 (IL-6).

Various methods known to those skilled in the art can be used to determine a reduction in the amount of inflammatory cytokines in a subject. For example, in certain embodiments, the amounts of expression of an inflammatory cytokine in a subject can be determined by probing for mRNA of the gene encoding the inflammatory cytokine in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, CA). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently-disclosed subject matter.

With further regard to determining levels of inflammatory cytokines in samples, mass spectrometry and/or immunoassay devices and methods can also be used to measure the inflammatory cytokines in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

With still further regard to the various therapeutic methods described herein, although certain embodiments of the methods disclosed herein only call for a qualitative assessment (e.g., the presence or absence of the expression of an inflammatory cytokine in a subject), other embodiments of the methods call for a quantitative assessment (e.g., an amount of increase in the level of an inflammatory cytokine in a subject). Such quantitative assessments can be made, for example, using one of the above mentioned methods, as will be understood by those skilled in the art.

The skilled artisan will also understand that measuring a reduction in the amount of a certain feature (e.g., cytokine levels) or an improvement in a certain feature (e.g., inflammation) in a subject is a statistical analysis. For example, a reduction in an amount of inflammatory cytokines in a subject can be compared to control level of inflammatory cytokines, and an amount of inflammatory cytokines of less than or equal to the control level can be indicative of a reduction in the amount of inflammatory cytokines, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In some embodiments of the presently-disclosed methods for treating an inflammatory disorder described herein, the inflammatory disorder is colitis. In some embodiments, administering the composition to a subject increases an amount of intestinal epithelial cell proliferation in the subject to thereby treat the colitis. In some embodiments, administering an effective amount of the edible plant-derived microvesicle compositions increases an amount of Wnt-β-catenin signaling in the intestine of a subject to thereby treat the colitis.

Still further provided, in some embodiments, are methods for treating a cancer. In some embodiments, a method for treating a cancer is provided that comprises administering to a subject in need thereof an effective amount of an edible-plant derived microvesicle composition of the presently-disclosed subject matter (i.e., where a microvesicle encapsulates a therapeutic agent). In some embodiments, the therapeutic agent encapsulated within the microvesicle and used to treat the cancer is selected from a phytochemical agent, a chemotherapeutic agent, and a Stat3 inhibitor as such agents have been found to be particularly useful in the treatment of cancer. As used herein, the term "cancer" refers to all types of cancer or neoplasm or malignant tumors found in animals, including leukemias, carcinomas, melanoma, and sarcomas.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from the group consisting of skin cancer, head and neck cancer, colon cancer, breast cancer, brain cancer, and lung cancer. In some particular embodiments, the cancer is a brain cancer such as, in some embodiments, a glioma.

In some embodiments, the edible plant-derived microvesicle compositions used to treat the cancer further comprise a cancer targeting moiety or, in other words, a moiety that is capable of preferentially directing a composition of the presently-disclosed subject matter to a cancer cell. Such cancer targeting moieties include, but are not limited to, small molecules, proteins, or other agents that preferentially bind to cancer cells. For example, in some embodiments, the cancer targeting moiety can be an antibody that specifically binds to an epitope found predominantly or exclusively on a cancer cell. As another example, in some embodiments, the cancer targeting moiety is folic acid, as folic acid or folate receptors have been found to be overexpressed on a variety of different types of cancer.

In yet further embodiments of the presently-disclosed subject matter, methods for diagnosing a colon cancer in a subject are provided. In some embodiments, a method for diagnosing a colon cancer in a subject is provided that comprises the steps of: administering to a subject an effective amount of a microvesicle composition including an edible plant-derived microvesicle incorporating a detectable label; determining an amount of the detectable label in a colon of the subject; and comparing the amount of the detectable label, if present, to a control level of the detectable label, wherein the subject is diagnosed as having colon cancer or a risk thereof if there is a measurable difference in the amount of the detectable label as compared to the control level. In some embodiments, the subject has colon cancer.

The terms "diagnosing" and "diagnosis" as used herein refer to methods by which the skilled artisan can estimate and even determine whether or not a subject is suffering from a given disease or condition (e.g., colon cancer). The skilled artisan often makes a diagnosis on the basis of one or more diagnostic indicators, such as for example an amount of a detectable label attached to an exosomal composition, the amount (including presence or absence) of which is indicative of the presence, severity, or absence of the condition.

Along with diagnosis, clinical disease prognosis is also an area of great concern and interest. It is important to know the stage and rapidity of advancement of the colon cancer in order to plan the most effective therapy. If a more accurate prognosis can be made, appropriate therapy, and in some instances less severe therapy for the subject can be chosen. Measurement of amounts of detectable labels attached to an edible plant-derived microvesicle composition of the presently-disclosed subject matter can be useful in order to categorize subjects according to advancement of colon cancer who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measured amounts of detectable labels disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of the detectable labels attached to the exosomal compositions. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition, the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, an amount of the detectable label of greater than a control level in some embodiments can signal that a subject is more likely to suffer from a colon cancer than subjects with a level less than or equal to the control level, as determined by a level of statistical significance. Additionally, a change in detectable label concentration from baseline levels can be reflective of subject prognosis, and the degree of change in detectable label levels can be related to the severity of adverse events.

In other embodiments, a threshold degree of change in the amounts of a detectable label can be established, and the degree of change in the amounts can simply be compared to the threshold degree of change in the level. A preferred threshold change in the detectable labels of the presently-disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently disclosed subject matter, multiple determination of one or more diagnostic or prognostic levels of the detectable labels attached to the administered exosomal compositions can be made, and a temporal change in the label levels can be used to monitor the progression of disease and/or efficacy of appropriate therapies directed against the disease. In such an embodiment for example, one might expect to see a decrease or an increase in the labels over time during the course of effective therapy. Thus, the presently-disclosed subject matter provides, in some embodiments, a method for determining treatment efficacy and/or progression of a colon cancer in a subject. In some embodiments, the method comprises administering the edible plant-derived microvesicle compositions including a detectable label at various time points and determining an amount of the detectable labels in the subject at a plurality of different time points such that those amounts can be compared with one another to provide an assessment of the measurements collected at the different time points. For example, a first time point can be selected prior to initiation of a treatment and a second time point can be selected at some time after initiation of the treatment. One or more levels of the detectable labels can then be measured at each of the different time points and qualitative and/or quantitative differences noted. A change in the amounts of the levels from the first and second samples can be correlated with determining treatment efficacy and/or progression of the disease in the subject.

The terms "correlated" and "correlating," as used herein, refers to comparing the presence or quantity of the measured detectable label in a subject to its presence or quantity in subjects known to suffer from, or known to be at risk of, a given condition (e.g., a colon cancer); or in subjects known to be free of a given condition, i.e. "normal individuals". For example, a level in a particular subject can be compared to a level known to be associated with a specific type of colon cancer. The subject's measured level of the detectable label subsequent to the administration of the labeled exosomal compositions is said to have been correlated with a diagnosis; that is, the skilled artisan can use the level to determine whether the subject suffers from a specific type of colon cancer, and respond accordingly. Alternatively, the subject's level can be compared to a control level known to be associated with a good outcome (e.g., the absence of colon cancer), such as an average level found in a population of normal subjects.

As noted, in some embodiments, multiple determination of one or more amounts of detectable labels can be made, and a temporal change in the amounts can be used to determine a diagnosis or prognosis. For example, a diagnostic level of the labels can be determined at an initial time, and again at a second time. In such embodiments, an increase in the amounts from the initial time to the second time can be diagnostic of a particular type of colon cancer, or a given prognosis. Likewise, a decrease in the levels from the initial time to the second time can be indicative of a particular type of colon cancer or a given prognosis. Furthermore, the degree of change can be related to the severity of colon cancer and future adverse events.

With regard to the term "detectable label," as used herein, the terms "detectable label," "label" and "labeled" refer to the attachment or incorporation (e.g., encapsulation) of a moiety, capable of detection by spectroscopic, radiologic, or other methods, to a microvesicle. Examples of labels include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for antibodies, metal binding domains, epitope tags). In some embodiments, labels are attached by spacer arms of various lengths to reduce potential steric hindrance. In some embodiments, the detectable label comprises a radioisotope or a fluorescent probe.

Fluorescent probes that can be utilized include, but are not limited to fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3, 3.5, 5, 5.5, and 7; phycoerythrin; phycoerythrin-Cy conjugates; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives (e.g., hydroxycoumarin, aminocoumarin, and methoxycoumarin); pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diazas-indacene; Alexa fluors (e.g., 350, 430,488, 532, 546, 555, 568, 594, 633, 647, 660, 680, 700, and 750); green fluorescent protein; and yellow fluorescent protein. The peak excitation and emission wavelengths will vary for these compounds and selection of a particular fluorescent probe for a particular application can be made in part based on excitation and/or emission wavelengths.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. Some of the following examples are prophetic, notwithstanding the numerical values, results and/or data referred to and contained in the examples. Additionally, the following examples may include compilations of data that are representative of data gathered at various times during the course of development and experimentation related to the presently-disclosed subject matter.

EXAMPLES

Throughout the following examples, the terms "exosome," "exosome-like particles," "ELP," "nano-vector," "edible plant-derived nano-vector," "EPNV," and grammatical variations thereof and other similar terms are used interchangeably to refer to the microvesicle compositions of the presently-disclosed subject matter, as described herein above.

Materials and Methods for Examples 1-6

Purification of Exosomes from Grapefruit and Grapes.

Fresh grapefruit and grapes were purchased from a local market and were washed and sterilized under a UV lamp for 30 min and processed using Good Laboratory Practice (GLP) procedures. The fruit was cut into two pieces, and the fruit fluids were collected into centrifuge tubes for exosomal purification using gradient centrifugation. Briefly, the skin of the fruit was removed by centrifugation for 10 min at 200×g. Supernatants were collected and centrifuged sequentially twice for 10 min at 500×$g_{max}$, once for 15 min at 2,000× $g_{max}$, and once for 30 min at 10,000×$g_{max}$. The pellet was referred to as microparticles. The supernatants were mixed with endogenous exosome depleted skim milk (1:1 by volume) and centrifuged for 60 min at 100,000×$g_{max}$. The pellet was collected, resuspended and the exosomes collected by sucrose gradient centrifugation. Exosomes were then washed with endogenous exosome depleted skim milk once and then resuspended in PBS. Purity and integrity of sucrose gradient-isolated exosomes was analyzed using a Hitachi H7000 electron microscope (Electronic Instruments, Akishima, Japan). To further minimize potential contamination during exosomal purification, exosomal endotoxin levels were quantified using the Limulus amebocyte lysate assay (Associates of Cape Cod Inc., Falmouth, MA) according to the manufacturer's protocol. The concentration of exosomes was then determined using the Bio-Rad (Hercules, CA) protein quantitation assay kit with BSA as a standard.

Labeling of Grape-Derived Exosomal-Like Particles (GELPs).

GELPs were labeled using an odyssey fluorescent dye IRDye800 kit (LI-COR Biosciences, Lincoln, NE) or DIR dye kit (Invitrogen, Carlsbad, CA). C57BL/6j mice were gavaged with the IRDye 800CW-labeled or DIR-labeled GELPs (100 μg), and mice were imaged using a prototype LI-COR imager (LI-COR Biosciences) for IRDye 800CW-labeled GELPs or for DIR-labeled GELPs. Mice receiving nonlabeled GELPs were used for establishing a baseline background.

Facs Analysis.

For cell surface marker staining, isolated cells were blocked at 4° C. for 5 minutes with 10 µg/ml of mouse Fc block (BD Biosciences, San Jose, CA) and then reacted with various fluorochrome-labeled antibodies including appropriate isotype controls for 30 minutes at 4° C. After washing twice, cells were fixed and analyzed using a FACS Calibur flow cytometer (BD Biosciences, San Jose, CA). Data were analyzed using FlowJo software (TreeStar, Ashland, OR). The following antibodies were used for immunostaining: EPCAM, CD14, F4/80, and annexin V (eBiosciences, San Diego, CA).

Preparation of Exosomal Curcumin and Quantification of Curcumin.

Exosomal curcumin was prepared by mixing curcumin with GELPs in PBS. After incubation at 22° C. for 5 min, the exosomal curcumin was separated from unbound curcumin by sucrose gradient centrifugation as described. To determine the concentration of curcumin in the samples, samples collected from mice were precipitated with emodin to remove proteins and analyzed using a method described previously. Protein concentration was calculated based on the absorbance units with respect to the concentration of curcumin in the standard curve.

ELISAs.

Supernatants, colon homogenates or serum were analyzed for the presence of IL-6, MIP1, IL-1β (all BD Biosciences, San Jose, CA), as per the manufacturer's suggested protocol.

Coomassie Blue staining of protein gels.

Total protein extracts from GELP, Grapefruit-derived Exosomal-like Particles (GFELP) and TS/A exosomes (100 µg/lane) were prepared using cold RIPA buffer (Pierce, Rockford, IL) and separated by 10% SDS PAGE. The gels were stained subsequently with Coomassie Blue and scanned using an Odyssey Scanner (Li—COR).

Induction of Arthritis.

DBA/1j female mice (Jackson Lab) were immunized at 7 weeks of age at the base of the tail with 200 µg of bovine collagen II (CII) dissolved in 100 µl of 0.05 M acetic acid and mixed with an equal volume (100 µl) of CFA (Chondrex Inc., Redmond, Washington, USA).

Treatment Protocols for Mice Immunized with CII.

Three weeks after challenge with collagen II and one day after a boost with incomplete adjuvant, mice received the following oral treatments every other day for 20 days: (1) GELP-Cur (4 mg/kg of body weight dose was used based on a dose-response curve); (2) Free curcumin (4.0 mg/kg of body weight), (3) GELPs, and (4) PBS (n=10 per group). Blood was collected immediately before and 1 h after treatment on days 1, 10 and 20, and urine and feces were collected on days 1, 10, and 20, as well as the day before treatment. Blood samples were collected for analysis of glutathione-s-transferase (GST) and alanine transaminase (ALT) activity on the last day of treatment. Curcumin in plasma, urine, and feces was quantified using reverse-phase HPLC analysis. At least ten mice were included per group.

Evaluation of the Development of Arthritis and Joint Damage.

Calipers were used to determine the diameter of each paw of each mouse every day for 20 days. Paw swelling was determined as the increase in diameter compared with the diameter at the initiation of the experiment. The severity of arthritis was graded according to the following scale: 0, normal with no swelling and erythema and no increase in joint diameter; 1, slight swelling and erythema with 0.1 to 0.3-mm increase in joint diameter; 2, swelling and erythema with 0.3 to 0.6-mm increase in joint diameter; 3, extensive swelling and erythema with 0.6 to 0.9-mm increase in joint diameter; 4, pronounced swelling and erythema with 0.9 to 1.2-mm increase in joint thickness or obvious joint destruction associated with visible joint deformity or ankylosis. Each limb was graded, resulting in a maximum clinical score of 16 per animal and expressed as the mean score on a given day.

LPS Mouse Septic Shock Model.

Curcumin (Cur) or GELPs-Cur (4 mg/kg of body weight) was injected intraperitoneally (IP) into C57BL/6j mice together with LPS (18.5 mg/kg, Sigma-Aldrich). PBS and GELPs alone (equal to the amount in GELPs-Cur) were used as controls. Mouse mortality was monitored over a period of 4 days.

DSS Plus AOM Induced Colon Cancer in a Mouse Model.

Colitis-associated colorectal cancer (CAC) was induced as described below. Six to seven week old female mice were injected intraperitoneally (IP) with 12.5 mg/kg azoxymethane (AOM; Sigma-Aldrich Chemical Co, St. Louis, MO). Beginning on the same day, mice were provided 0% dextran sulfate sodium (DSS; MP Biomedicals, Solon, OH, molecular weight 35,000-50,000 kDa) water for 7 days followed by 14 days of untreated drinking water. Mice were subjected to two more DSS water—untreated drinking water cycles followed by untreated water for 28 days. Three days after the last DSS cycle, the mice were randomly grouped for treatments as described below: The treatment groups were: Group 1: grape exosomes containing curcumin (GELP-Cur, 4.0 mg/Kg of body weight); Group 2: grape-fruit exosomes containing curcumin (GFELP-Cur, 4.0 mg/Kg of body weight) and Group 3: curcumin in liposomes (4.0 mg/Kg of body weight). The mice were gavaged treated every other day for 9 days (10 mice/group). At the termination of the study, mice were sacrificed by $CO_2$ asphyxiation and all organs were carefully inspected for macroscopic pathological lesions. The intestines, liver, and spleen were removed, and fixed in 10% buffered formalin for a minimum of 24 h. The colon was excised, flushed with saline, the length measured, cut open longitudinally, flattened on filter paper and washed with saline. Macroscopic inspection of the colons was carefully carried out, with the number, size and location of visible tumors recorded.

Statistical Analysis.

Statistical analysis of the survival curves was performed using a log-rank test. Statistical analyses of tumor sizes were performed using the Mann-Whitney test. Comparisons of one-variable data were performed using a two-tailed unpaired Student's T-test. When the F-test indicated variances differed significantly, Welch's correction to the Student's T-test was employed. Comparisons of two variable data were performed using a two-way ANOVA with Bonferroni post test. All tests were performed using 95% confidence intervals. Data were expressed as the means±SEM. *=$p<0.05$, =$p<0.01$, *=$p<0.001$.

Example 1—Analysis of Quantities of Exosome-Like Particles in Fruit

Figure 1B:
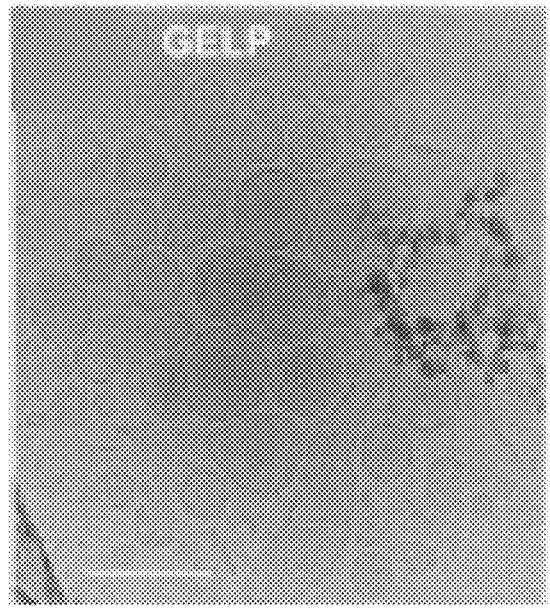
Figure 1C:
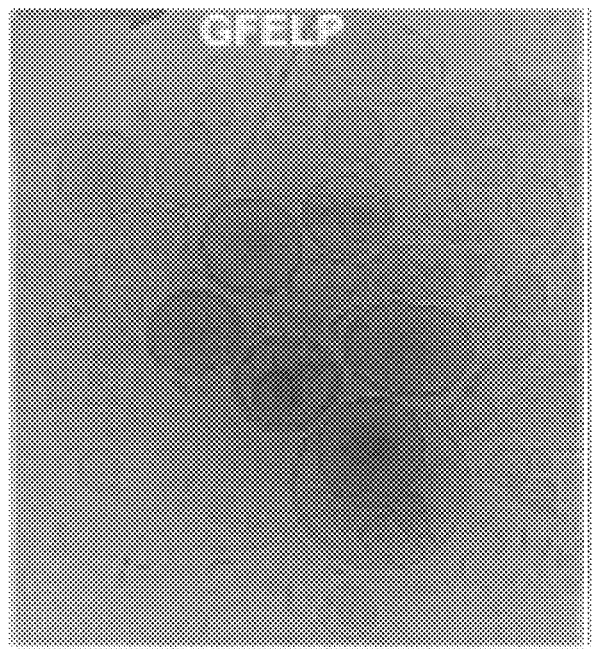
Figure 1D:
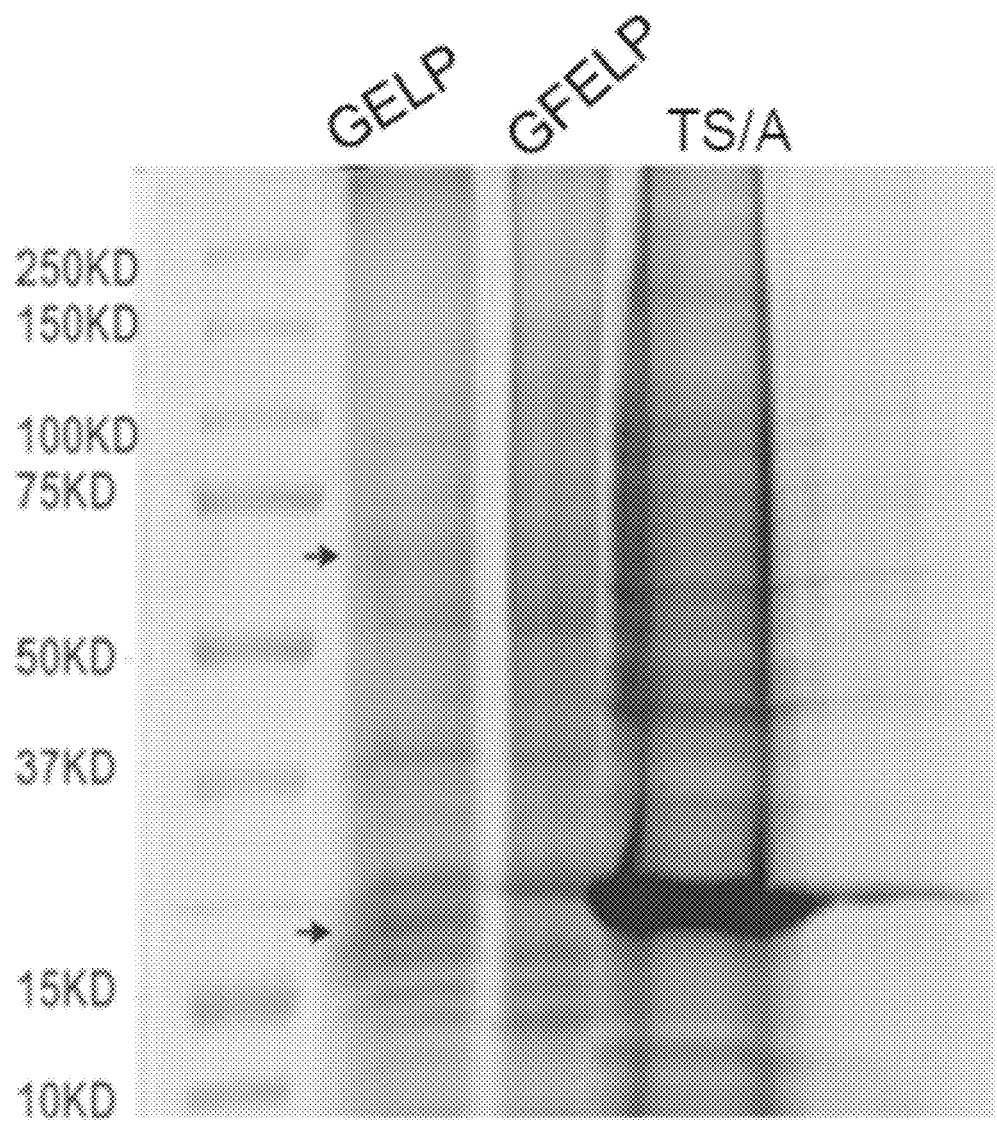

Based on the reports that plants also release exosome-like particles (nanoparticles), edible fruits were screened and it was found that grapes release large quantities of nanoparticles. In brief, under Good Laboratory Practice (GLP) guidelines, fresh grapes were purchased from the market, washed and sterilized under UV lamps for 30 min. The juice from crushed grapes was collected into centrifuge tubes. GELPs were purified using gradient centrifugation with three bands being visible (FIG. 1A); the middle band (density=1.12-1.23 g/ml) was washed and resuspended in PBS. The concentration of GELPs was determined by analyzing protein concentration using the Bio-Rad protein quantitation assay kit with BSA as a standard. The sucrose-separated GELPs were examined with a TECNAI T-12 electron microscope (FEI Co., Hillsboro, Oregon). EM examination indicated that grapes produce particles 50-100 nm in size with features characteristic of exosomes (FIG. 1B). Using a protocol identical to the one described above, grape-fruit nanoparticles (FIG. 1C) were also isolated. Quantification of the exosomes suggested that both grapes (2.2 g/pound of grape), and grapefruit (1.6 g/pound of grapefruit) release large quantities of nanoparticles. Coomassie blue stained 10% polyacrylamide gels of fruit nanoparticle samples showed that both of the fruit-derived nanoparticles have a different composition from exosomes derived from the mouse TS/A breast tumor cell line (FIG. 1D).

Example 2—Analysis of Lipid Content in Fruit Exosomes

Using a tandem mass spectrometer with a collision cell (chamber where fragmentation occurs) between the two mass specs, the FELPs samples we submitted to the Kansas Lipidomics Research Center, (Kansas State University, Manhattan, KS) for lipid analyses. Among the lipids detected, phosphatidylcholines (PC) are enriched in exosomes isolated from tomatoes (20.8%), and grapefruit (28.5%). Phosphatidylethanolamines (PE) are enriched in exosomes isolated from tomatoes (18.1%), and grapefruit (26.09%), grapefruit (45.5%). Phosphatidic acid (PA) is enriched in both exosomes and microparticles isolated from tomatoes (40.5%, 46.5%), and grapefruit (53.1%, 73.4%), but significantly lower in grapefruit exosomes and microparticles (2.4% and 1.9%).

Figure 2A:
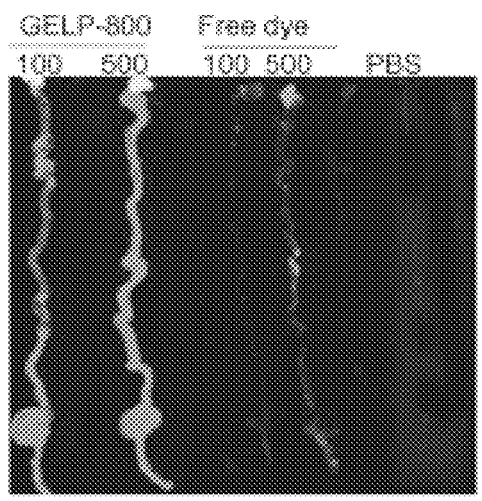
FIGS. 2A-2E include images and graphs showing the uptake of GELPs by various cells and tissues subsequent to oral administration of the GELPs, including: photographs showing the binding of GELPs in mice intestines after the mice were orally administered GELPs labeled using an IRDye 800CW labeling kit, PBS diluted free IRDye 800CW dye used at an equal amount for labeling GELPs, or PBS, where the GELPS or free dye were administered at a dose of 100 or 500 mg in 100 μl of PBS (FIG. 2A); graphs showing the fluorescence activated cell sorting (FACS) of intestinal epithelial cells or peripheral blood for EPCAM$^+$PHK67$^+$ or CD14$^+$PHK67$^+$ cells within the gated R1 region, where mice were treated with GELP (200 mg), and where PHK67 dye was administered orally at doses from 10 to 200 mg in 100 μl of PBS and the cells were collected three hours after administration (FIG. 2B); a graph showing the percent of PKH67+ cells in the peripheral blood of mice as a function of the amount of GELP orally administered to each mouse (FIG. 2C); photographs showing synovial tissues of mice orally administered 200 μg of GELPs or free dye orally (FIG. 2D); and a graph and images showing the FACS analysis of F4/80$^+$PHK67$^+$ cells (inset, right panel) in the gated R1 region (inset, left panel) of cells from synovial tissues of mice orally administered GELP.
Figure 2B:
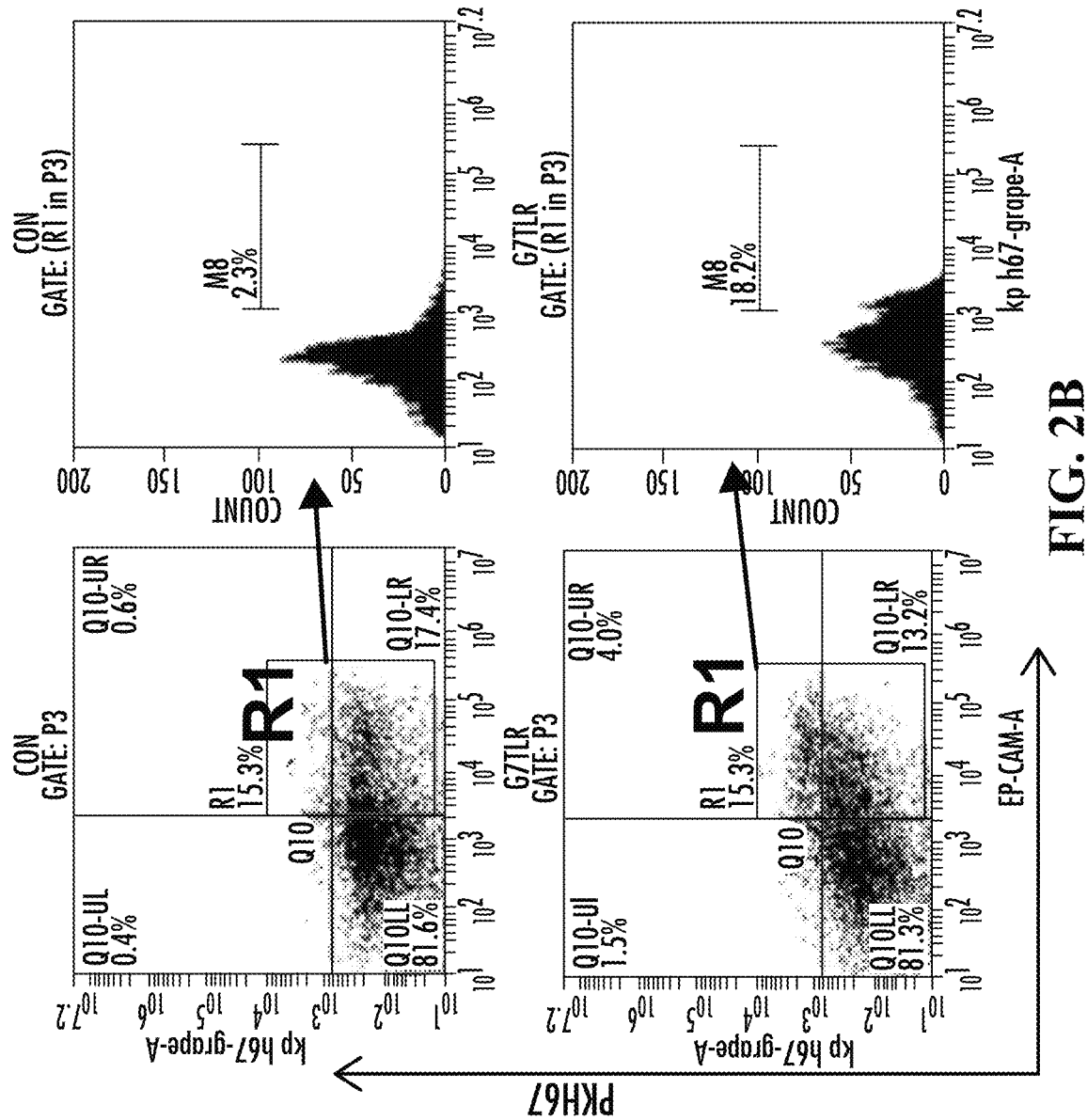
Figure 2C:
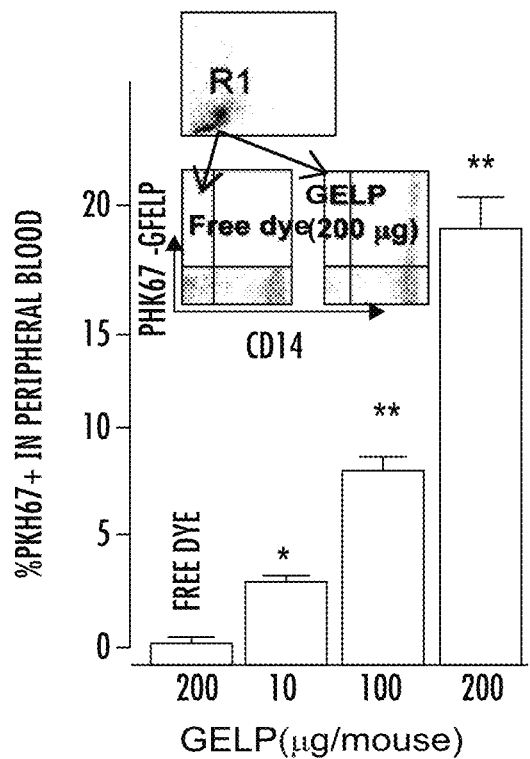
Figure 2D:
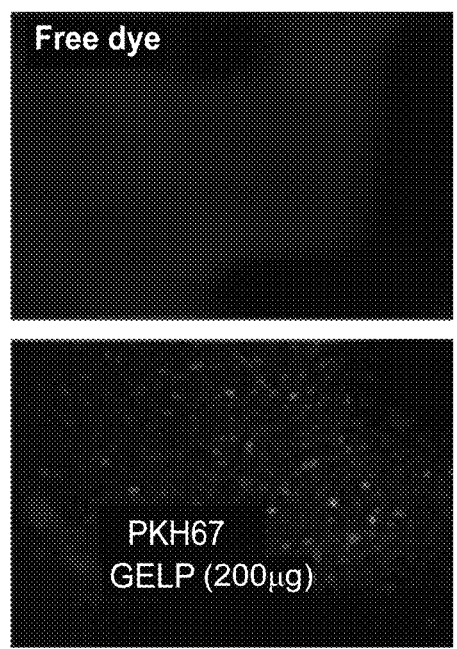
Figure 2E:
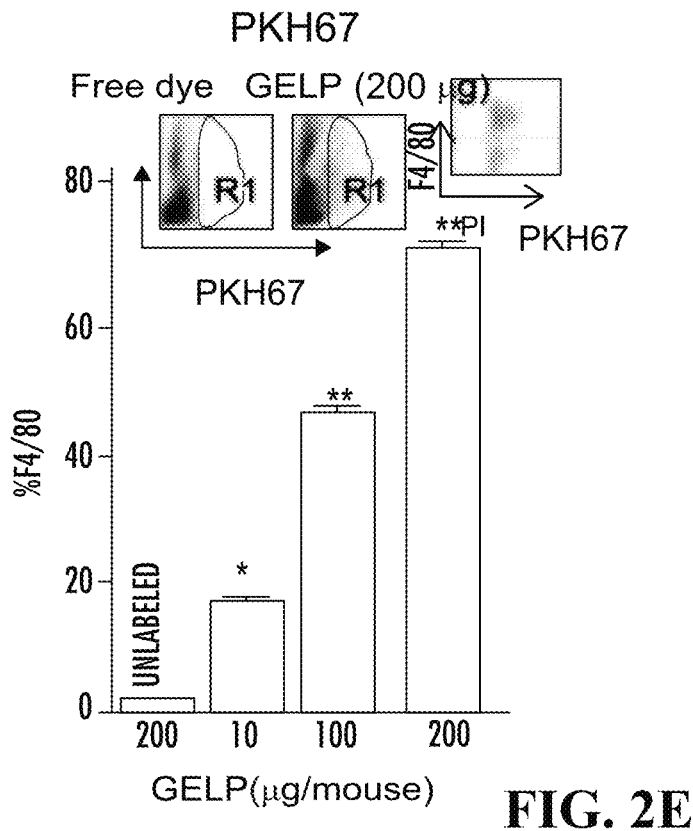

Example 3—Analysis of the Ability of Intestinal Epithelial Cells and Macrophages to Take Up Grape Exosomes DBA/1j female mice were immunized at 7 weeks of age at the base of the tail with 200 μg of bovine CII dissolved in 100 μl of 0.05 M acetic acid and mixed with an equal volume (100 μl) of CFA (Chondrex Inc., Redmond, Washington, USA). Three weeks later, DBA/1j mice that had been immunized with collagen II for 3 weeks to induce arthritis were administered Odyssey 800 dye-labeled GELPs orally. Control groups of DBA/1j mice that had been similarly immunized with collagen II to induce arthritis were administered the same amount of free Odyssey 800 dye or PBS. Twelve hours after oral administration of the GELPs, the results of imaging analysis showed that Odyssey 800 dye-labeled GELPs bind to the intestine (FIG. 2A). The binding was GELP specific as the binding signal generated from mice given free dye or PBS was much weaker. Further FACS analysis of cells isolated from the intestines provided the evidence that most of the PHK67$^+$ cells are also EPCAM$^+$ (FIG. 2B), which is a marker for epithelial cells. It was then determined whether the intestine-bound GELPs can enter into peripheral blood as do other nanoparticles. To identify the types of cells that take up GELPs, the sucrose-purified GELPs were labeled with PKH67 as described previously. Labeled GELPs or free dye were administered orally to 10-week-old DBA/1j mice that had been immunized with collagen II for 3 weeks to induce arthritis. Analysis of the distribution labeled GELPs indicated that 3 h after administration GELP-positive cells were observed in the peripheral blood and spleen (CD14$^+$PHK67$^+$), but not in the lung or liver (FIG. 2C). It was further observed that the higher the amount of GELP administered, the higher percentage of PHK67$^+$ cells was present in the peripheral blood. Twenty-four hours after oral administration, the mice were killed. An accumulation of GELP-positive cells was observed in frozen sections of the synovial tissue of the inflamed joints of the mice with collagen-induced arthritis (FIG. 2D) but not naïve DBA/1j mice. FACS analysis of collagenase-digested swollen joints indicated that within the gated R1 region more than 65% of the PHK67$^+$ cells were F4/80$^+$ macrophages (FIG. 2E). The percentage of F4/80$^+$ macrophages was dependent on the dose of GELPs administrated orally (FIG. 2E). These data suggested that GELPs are taken up by intestinal epithelial cells, as well as CD14$^+$ cells, and that these CD14+ cells carrying GELP migrate to areas of inflammation.

Figure 3A:
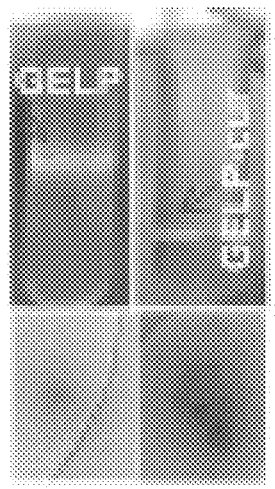
FIGS. 3A-3F includes images and graphs showing the attenuation of collagen II-induced arthritis in DBA/1j mice orally administered GELPs encapsulating curcumin (GELP-Cur), including: images of GELPS before and five minutes after co-incubation of 40 μl of 20 mM curcumin with 500 μg GELP in 200 μl PBS at 22° C.

Example 4—Analysis of Use of GELPs as Curcumin Carriers to Treat Collagen II-Induced Arthritis of DBA/11 Mice without Toxicity Since GELPs are selectively taken up by monocytes, it was conceivable that the GELPs could be used as a vehicle to deliver anti-inflammatory drugs in a monocyte-specific manner Initially, curcumin was selected as it is an anti-inflammatory agent that is hydrophobic and could complex with GELPs, which are lipid-enriched, hydrophobic nanoparticles. Moreover, curcumin has therapeutic effects on both collagen II-induced arthritis and human rheumatoid arthritis. In these experiments, it was observed that the GELPs bound curcumin (FIG. 3A). Using an HPLC method as described to quantify curcumin bound to GELPs, the results indicated that curcumin bound to GELPs in large quantities (2.5±0.3 mg/g of GELPs). To determine whether treatment of mice with GELP-complexed curcumin (GELP-Cur) can reduce or eliminate arthritis in a mouse model, the collagen II-induced inflammatory arthritis of DBA/1j mice was used for proof of concept. Arthritis was induced using a standard protocol. Three weeks after challenge with collagen II and one day after a boost with incomplete adjuvant, mice received the following oral treatments every other day for 20 days: (1) GELP-Cur (4.0 mg/Kg of body weight); (2) Free curcumin (4.0 mg/kg of body weight), (3) GELPS, and (4) PBS (n=10 per group). Blood was collected immediately before and 1 h after treatment on day 1, 10 and 20, and urine and feces were collected on days 1, 10, and 20, as well as the day before treatment. Blood samples were collected for analysis of GST and ALT activity on the last day of treatment. Curcumin in plasma, urine, and feces was quantified using reverse-phase HPLC analysis as described previously.

Levels of Curcumin in Blood and Excreta.

The results of HPLC analysis of plasma indicated that mice receiving GELP-Cur had curcumin amounts of 78±4.2 nmol/L 1 h post-oral administration on day 1 and at similar levels 1 h post-administration on days 10 and 20. Curcumin was not detected in the plasma of the groups of mice treated with free curcumin, GELPs alone, or PBS. In contrast, analysis of urine indicated that curcumin was present at much higher levels in the group of mice receiving free curcumin (0.7±0.1 μmol/L) than those that received GELP-Cur (0.02±0.01 μmol/L). In day 1 fecal samples, the curcumin levels from mice treated with free curcumin were 101±11.2 nmol/g dried feces; whereas, the levels in the GELP-Cur-treated group were 15±1.1 nmol/g dried feces. The liver enzyme levels for ALT (36±8.1 U/I) and GST (25±5.2) were not significantly different among the treatment groups: GELP-Cur (p=0.56), curcumin (p=0.46), and GELPs (p=0.78) in comparison with the group treated with PBS.

Biological Affects of Oral Curcumin.

Figure 3B:
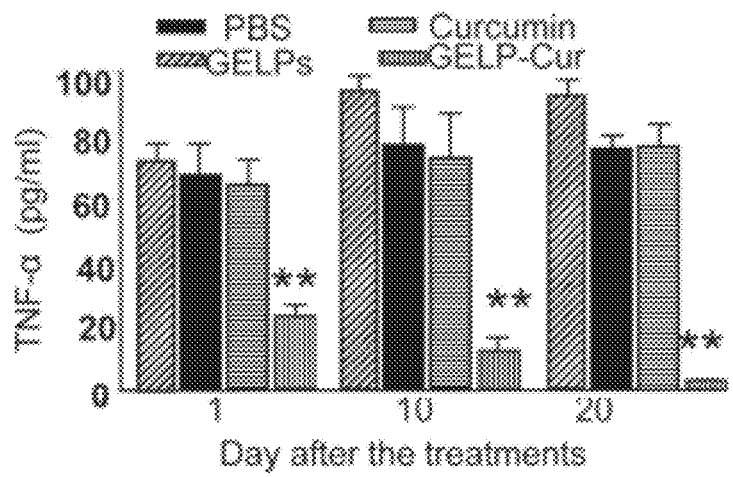
Figure 3C:
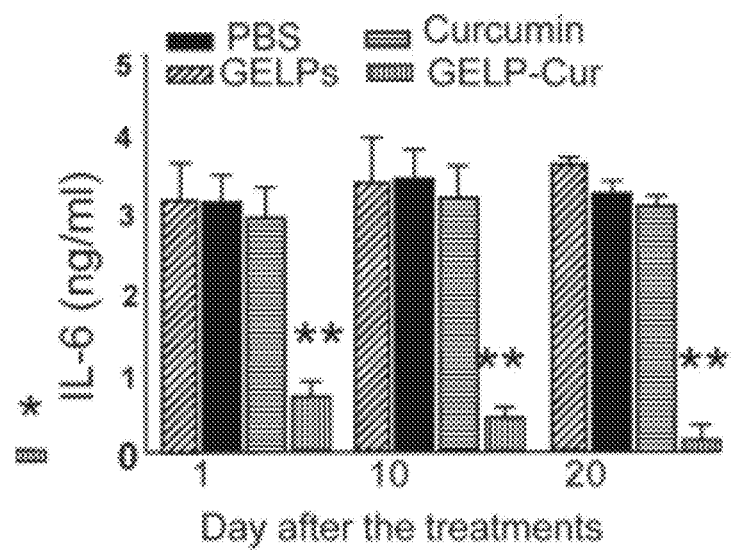
Figure 3D:
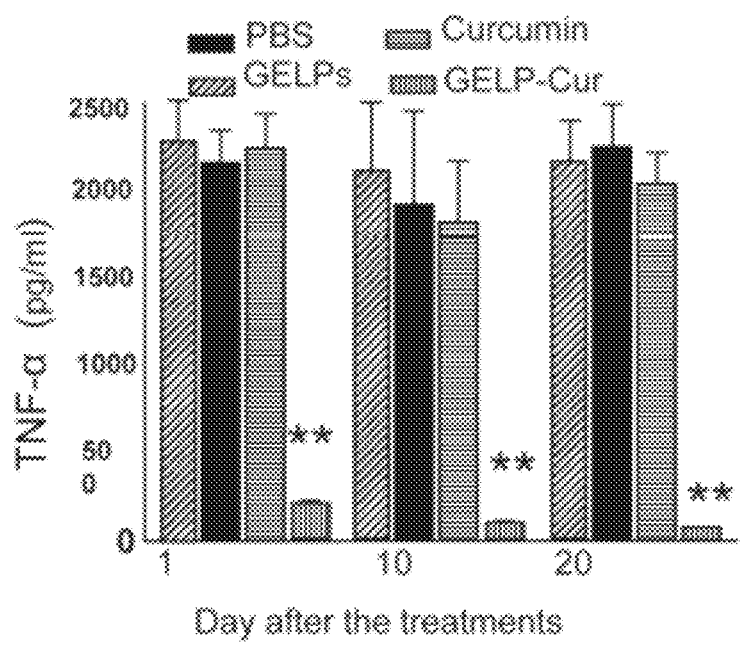
Figure 3E:
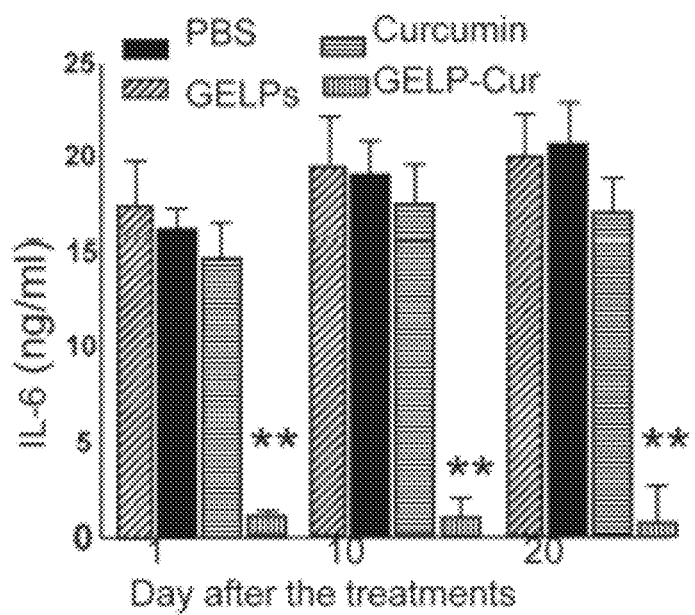
Figure 3F:
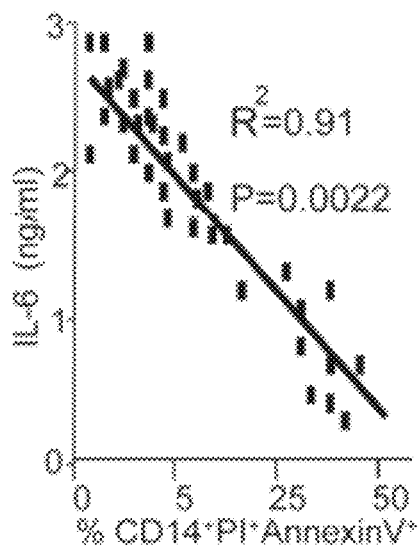

The sera levels of TNF-α (FIG. 3B) and IL-6 (FIG. 3C) were much lower in the group of mice treated with GELP-Cur than in the other treatment groups. This was supported by lower levels of both TNF-α (FIG. 3D) and IL-6 (FIG. 3E) in supernatants when whole blood samples were cultured for 24 h with LPS (100 ng/ml). The in vivo inhibition of induction of IL-6 (FIG. 3F) or TNF-α correlated with the induction of apoptosis in monocytes that were CD14$^+$PI$^+$ AnnexinV$^+$ (FIG. 3F). In addition to the reduction in IL-6 and TNF-α and the induction of monocyte apoptosis after GELP-Cur treatment, there was less macroscopic evidence of arthritis in the GELP-Cur-treated mice when compared with mice treated with free curcumin, GELPs only, or PBS.

Collectively, the data generated in this study supports the notion that curcumin strongly binds to GELPs leading to an enhancement of curcumin stability and bioavailability. After GELP-Cur treatment, there was less macroscopic evidence of arthritis in the GELP-Cur-treated mice when compared with mice treated with free curcumin, or PBS.

Example 5—Analysis of Use of GELPs as Curcumin Carriers to Treat Septic Shock

GELPs can be used as curcumin carriers to protect mice against LPS induced septic shock. Using an identical treatment protocol as described above, GELP-Cur-treatment led to 100% protection of C57BL/6 mice (10 mice/group) against LPS induced sepsis in a murine model. In contrast, oral administration of free curcumin at an amount equal to that in GELP-Cur had no effect on morality (8/10 mice died) as compared to mice treated with PBS (9/10 mice died).

Example 6—Analysis of Ability of GELP-Cur Treatment to Decrease Development of Colitis-Associated Colon Cancer To examine the therapeutic effects of GELP-Cur during colitis-associated tumorigenesis, a well-established model of colitis-associated cancer (CAC) was used. Mice received a single injection of azoxymethane (AOM, 10 mg/kg body weight), followed by administration of three cycles of dextran sulfate sodium (DSS, 2% in water) as outlined in FIG. 4. GELP-Cur or GFELP-Cur (gavaged at 4 mg/kg of body weight, every other day for 3 weeks) treated mice had a significantly lower tumor burden than mice treated with free curcumin (FIG. 5A). The average tumor number per mouse was more than two-fold decreased in GELP-Cur or GFELP-Cur treated mice compared to curcumin treated mice (3.1 vs. 8.5, p<0.01). In addition to the decrease in tumor burden, GELP-Cur or GFELP-Cur treated mice also had a significantly lower number of larger tumors (>1 mm$^2$) (p<0.05). Significantly decreased serum levels of IL-6 and MIP-1 were also detected in whole colon homogenates of GELP-Cur or GFELP-Cur treated mice compared to curcumin treated mice (p<0.05) (FIGS. 5B and 5C).

Discussion of Examples 1-6

Oral delivery using artificially-synthesized nanoparticles has been identified as an alternative delivery system that can overcome the poor absorption of curcumin through the intestines; however the challenges related to efficient nanoparticle delivery, clearance and toxicity must be overcome before nanoparticles can be used in a clinical setting. In this regard, it is appreciated that exosomes are released from many types of cells and theoretically could be used as a biodegradable delivery vehicle. Data suggest that the stability, solubility and bioavailability of curcumin is enhanced dramatically by encapsulating the curcumin in mammalian-derived exosomes (Exo-cur). It has further been demonstrated that mice treated orally with Exo-cur are completely protected against LPS-induced septic shock. Although promising, the feasibility of that approach for treatment of patients is limited by the need for large scale production of mammalian exosomes. In the foregoing studies, alternative sources of exosomes were thus explored and it was surprisingly found that several edible fruits are a source of large quantities of nanoparticles (also referred to as exosome-like particles). This indicated the possibility that fruit-derived nanoparticles might be a potential delivery vehicle for use in clinic settings. It was found that nanoparticles released from the flesh of grapes and other fruit as well could be of particular usefulness as a therapeutic delivery vehicle based on data presented in the foregoing Examples, indicating that: (i) oral administration of grape nanoparticles at doses of up to 40 mg/kg of mouse body weight was safe without evidence of liver damage; (ii) using mammalian T cell-derived exosomes, grape-derived exosomes could be used to encapsulate curcumin and oral administration of those grape exosome-like particles (GELP) carrying curcumin (GELP-Cur) protected mice against LPS-induced septic shock and did so by specifically targeting inflammatory myeloid cells; (iii) oral administration of GELP-Cur protected mice against collagen II-induced arthritis, and (iv) oral administration of GELP-Cur had a significant therapeutic effect on AOM/DSS induced colon cancer. The data also suggested that grape nanoparticles were preferentially taken up by intestinal epithelial cells, monocytes and macrophages. As such, it was further believed that the foregoing strategy could be applied to any disease in which activation of macrophages and monocytes played a role in the disease process.

In addition, the foregoing studies indicated that the exosomal compositions could play a role in the development of a non-invasive food-derived system for the delivery of curcumin and perhaps other drugs, as well as multiple drug carriers. The foregoing results provided novel approaches to eliminate/reduce chronic inflammation in inflammatory tissue and yielded a new, cost-effective, and practical therapeutic method for treatment of inflammatory-related diseases including inflammatory RA in patients; thus improving the health status of that patient population. The studies also had more general implications in terms of the basic biology of the effects of diet and the consumption of edible fruits and vegetables on health and disease. Exosome-like nanoparticles are released from many types of fruits or plants and it is conceivable that these exosomes may play key roles in promoting the delivery of specific nutrients, phytochemicals, and other ingested bioactive compounds (beneficial or otherwise) to the immune system.

Example 7—Analysis of Ability of GELP Treatment to Protect Mice Against DSS-Induced Mortality and Colitis Treatment:

To test whether fruit derived nanoparticles prevented DSS-induced colitis, C57BL/6 were given 3% DSS (MW 36,000-50,000; MP Biomedicals, Solon, OH) dissolved in reverse osmosis water ad libitum for 7 d (i.e., one cycle of DSS). Gavages of PBS, GFELP or GELP treatments (100 ug/mouse/gavage in 200 ul PBS) were given for five consecutive days starting at day 0 after the administration of 3% DSS. On day 8, mice were returned to untreated drinking water and sacrificed on day 15 since all PBS-fed mice were dead within day 15 after drinking 3% DSS contained water.

Evaluation for Treatment Effects:

Mice were checked for rectal prolapse/macroscopic bleeding, and accumulated mortality. The presence of blood in the stools was assessed by a guaiac paper test (ColoScreen Occult Blood Test, Helena Laboratories, Beaumont, TX) using a 0 to 4 scale: 0=negative, 1=faintly blue, 2=moderately blue, 3=dark blue, 4=fecal blood visible to the eye. Each mouse was scored 4 times per day, resulting in a maximum clinical score of 16 per animal and expressed as the mean score on a given day.

After mice were sacrificed, cryostat sections (5 µm) of the intestinal tissue were prepared and stained with hematoxylin and eosin. The stained section was analyzed in a blind fashion with a light microscope (BX10, Olympus). The pathophysiology of the tissue was characterized by crypt loss and thickening of the villus length from the base of the villus to the villus apex of GELP and PBS gavaged intestines was measured microscopically. The intestinal tissues were also fixed and stained for cell proliferation by BRDU staining, immunohistologically stained for the stem cell marker, BMI1, and β-catenin using a method as described.

Permeability Test:

At day 7 post-DSS treatment, mice were sacrificed via $CO_2$ asphyxiation and intestinal tissues were resected. Upon equilibration of the tissue and measurement of electrical parameters, 4-kD FITC-dextran was added to the mucosal side to achieve a final concentration of 0.01 mM. Permeability (flux) was determined after removal of medium from the serosal compartment at the end of a 90 minute experimental period. The medium was then assessed for fluorescence using a microplate fluorescence reader (FL-500, BIO-TEK, Vermont, USA) at an excitation wavelength of 485 nm and an emission wavelength of 530 nm.

Immunoblotting.

Isolated jejunal IECs and jejunal tissues were saved. Total cellular protein extracts from intestinal tissues, CT26 colon cells (ATCC) or MCA38 colon cells were prepared using cold RIPA buffer (Pierce, Rockford, IL). Expression of total and phosphorylated GSK3β were detected using a method as described previously.

Immunohistochemistry.

Frozen tissue sections from mouse jejunum (4 µm), CT26 (ATCC) or MCA38 (ATCC) colon cells were prefixed in paraformaldehyde. Tissue sections were stained with anti-β-catenin, BMI1, and anti-BRDU antibodies. 4',6-diamidino-2-phenylindole dihydrochloride (DAPI) was used for nuclear counterstaining Images were captured using a Zeiss microscope and Axioviewer image analysis software (Carl Zeiss Corp).

Bacterial Counts in the Liver.

For the determination of bacterial burden in mouse liver, at day 7 after 3% DSS treatment, 5 mice from each treated group were sacrificed, and livers were homogenized. Dilutions of the homogenates were plated on cystine heart agar plates and incubated for 24 h at 37° C. Bacterial colonies were counted and recorded as CFU per ml per gram of tissue.

Statistical Analysis.

Results were presented as the mean±SEM. Data were analyzed using analysis of variance, 2-tailed Student's t test, and the Mann-Whitney test as appropriate (Prism, GraphPad, San Diego, CA). P values of ≤0.05 were considered significant.

Figure 6C:
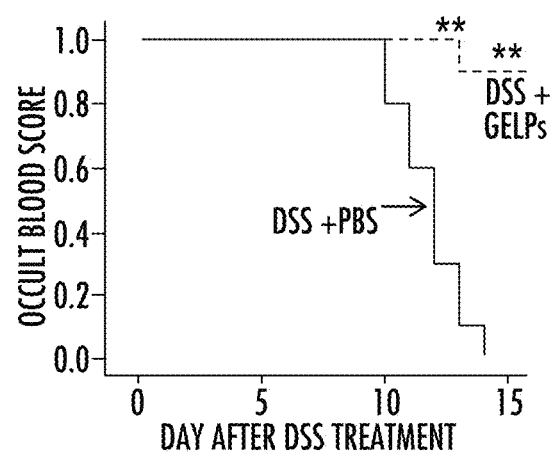
Figure 6D:
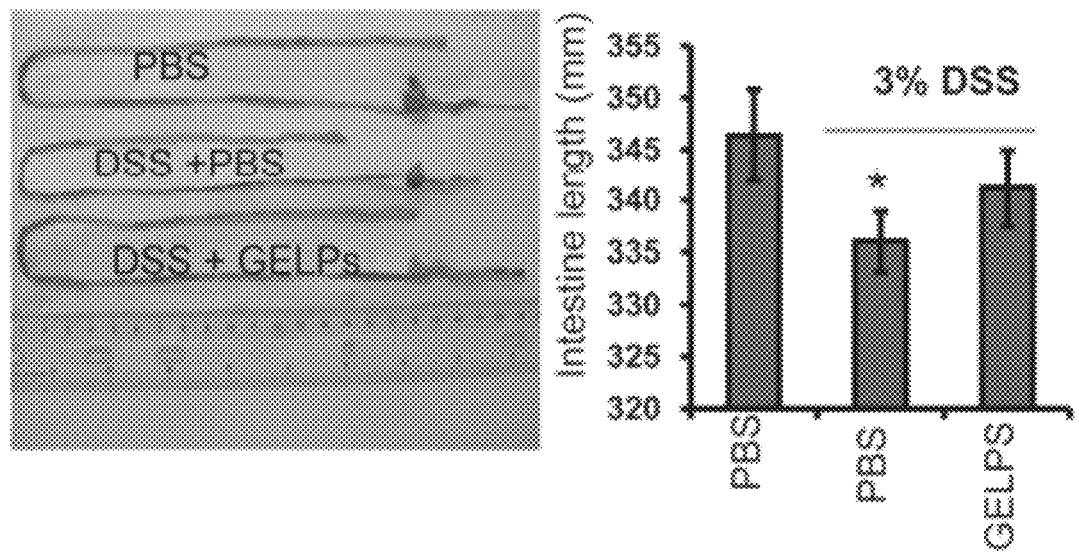
Figure 6E:
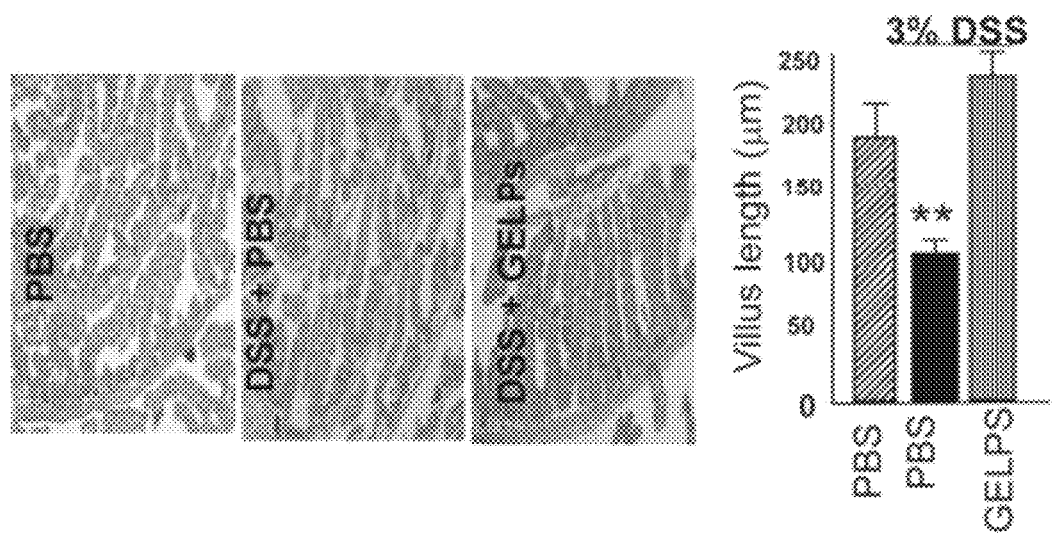

GELP gavaged mice and PBS mice were provided a 3.0% solution of DSS in the drinking water for 7 d and observed for 15 days. All DSS-treated mice developed colitis, as indicated by being severely depressed (FIG. 6A) and based on stool quality (bloody stool, FIG. 6B). At day 13, more than 80% of the mice gavaged with PBS were dead. In contrast, GELP gavaged mice showed no signs of depression and less blood was detected in stool samples (FIGS. 6A and 6B). There were no GELP treated mice dead by day 15 (FIG. 6C). Mice were sampled and killed at day 7 after being provided 3% DSS in water and histological and intestine permeability analyses were performed. As expected, colon length in PBS-gavaged control mice was significantly shorter (FIG. 6D, P<0.01) compared with non-DSS untreated control mice. However, in GELP gavaged mice, colon length was the same as non-DSS treated control mice (FIG. 6D). Histological scoring of colonic sections showed less severe damage of intestinal tissue in GELP gavaged mice compared with PBS gavaged mice (FIG. 6E) with a significantly thicker mucous layer in the GELP gavaged mice (FIG. 6E).

Figure 6F:
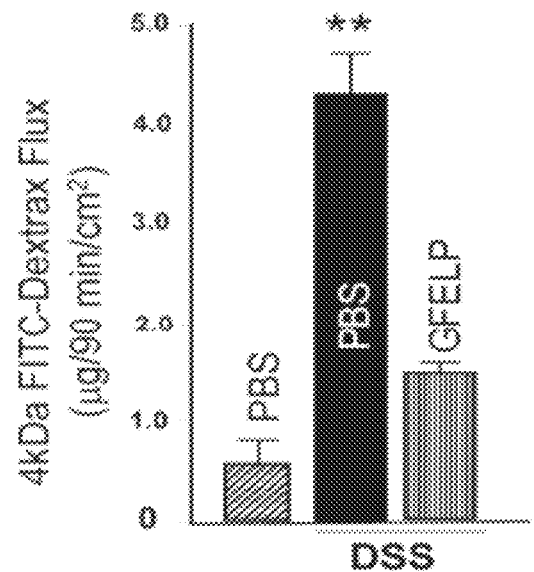
Figure 6G:
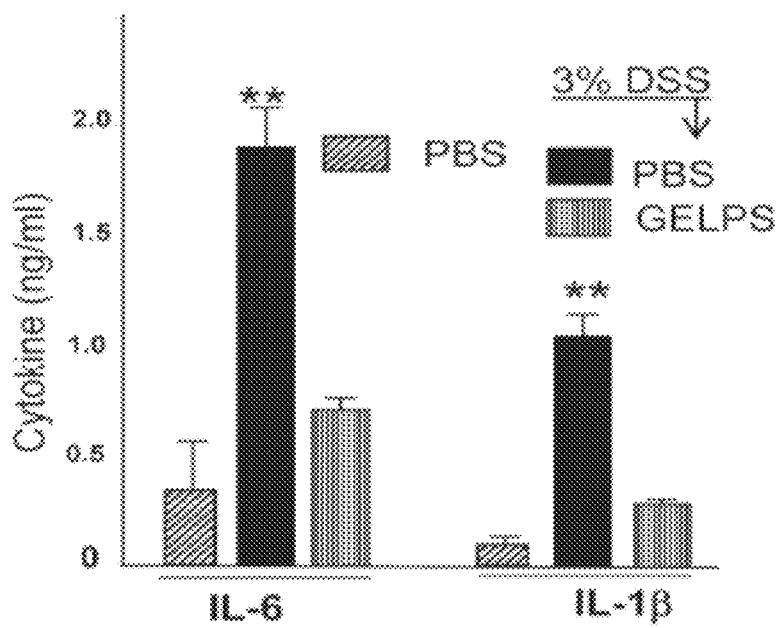
Figure 6H:
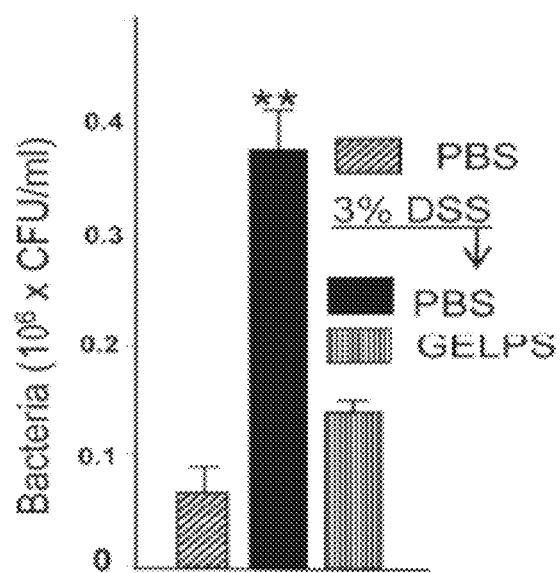

Intestinal epithelial cells, in addition to promoting digestion and absorption of nutrients, perform essential barrier functions by tightly regulating intestinal permeability. It was found that there was remarkably elevated permeability in the small intestine after 7 days consumption of 3% DSS in drinking water and the increase was significantly higher in PBS gavaged mice compared to GELPs gavaged mice (FIG. 6F). Consistently, a significantly higher amount of bacteria translocated to mesenteric lymph nodes (MLN) in PBS gavaged mice relative to GELP treated mice after 7 days consumption of 3% DSS water (FIG. 6H), demonstrating that GELPs treatment prevented DSS induced intestinal barrier dysfunction after a DSS challenge. DSS induced colitis is accompanied by an increase in the levels of inflammatory cytokines, including IL-6 and IL-1β. Levels of circulating cytokines in the serum were measured, and it was found that IL-6, as well as IL-1β were significantly higher in the peripheral circulation in PBS gavaged mice (FIG. 6G) when compared to GELP gavaged mice. This indicated that GELP treatment prevented the induction of inflammatory cytokines that play an essential role in DSS induced colitis.

Figure 7A:
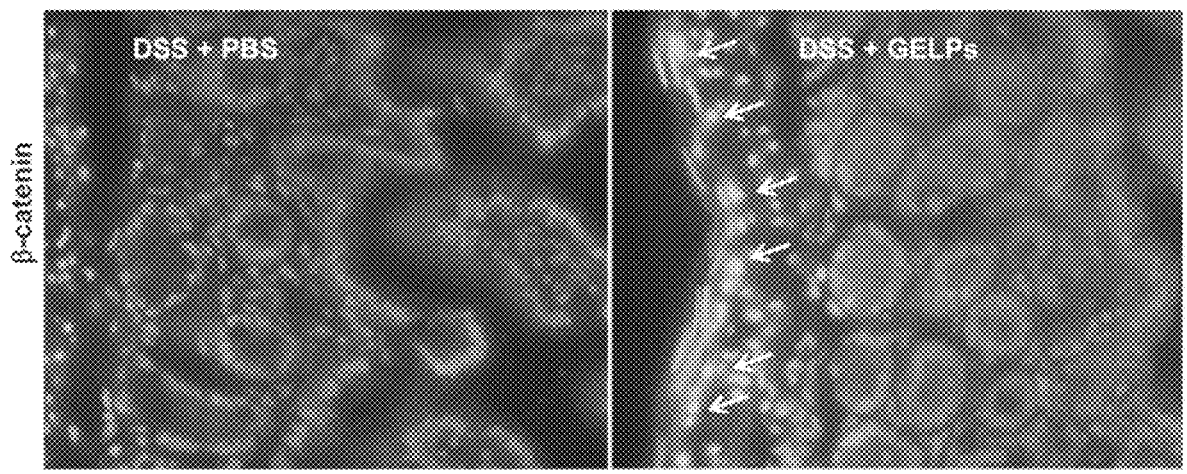
FIG. 7A-7G include images showing the increased expression and heterogeneous distribution of nuclear β-catenin in the intestine of mice gavaged with PBS or GELPs; including images showing representative staining for β-catenin from PBS or GELP gavaged mice at a low magnification (FIG. 7A, 10×) and a high magnification (FIG. 7B, right column), where the arrows indicate that the β-catenin positive cells; an image of a western blot of protein lysates from the intestines of PBS or GELP gavaged mice that were analyzed for ser 9 phosphorylated GSK3β, total GSK3β and β-actin (loading control) expression (FIG. 7C); and images showing immunohistochemistry and western blot analysis of CT26 (FIGS. 7D and 7F, respectively) or MCA38 (FIGS. 7E and 7G, respectively) in colon cells treated with GELPs (10 μg/ml) or BSA as control, where β-catenin expression and localization was determined via immunohistochemistry with β-catenin and is shown at low magnification (left panels) or increased magnification (right panels), and where total protein from lysates of each treatment was analyzed for ser 9 phosphorylated GSK3β, total GSK3β, and β-actin (loading control) expression.
Figure 7B:
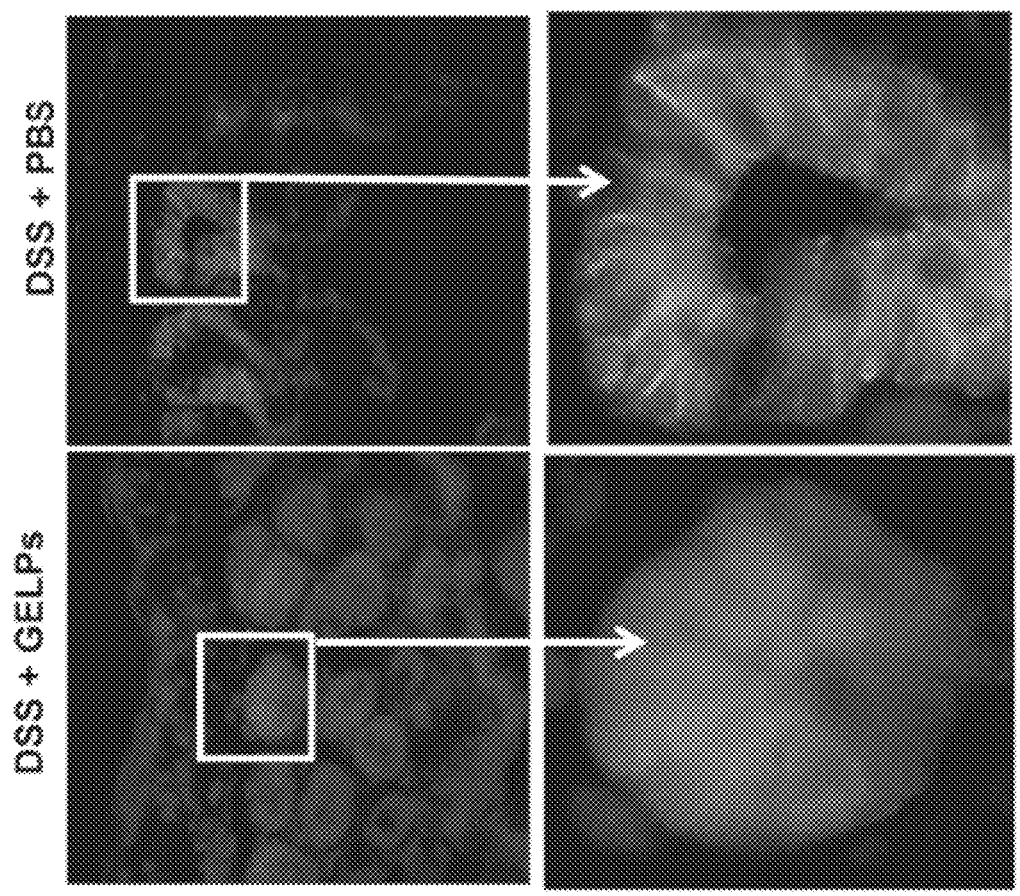
Figure 7C:
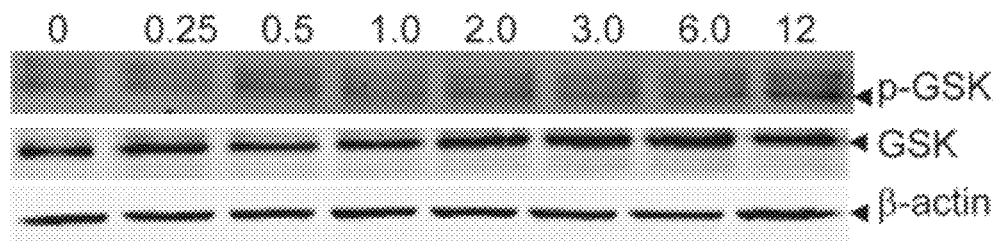
Figure 7D:
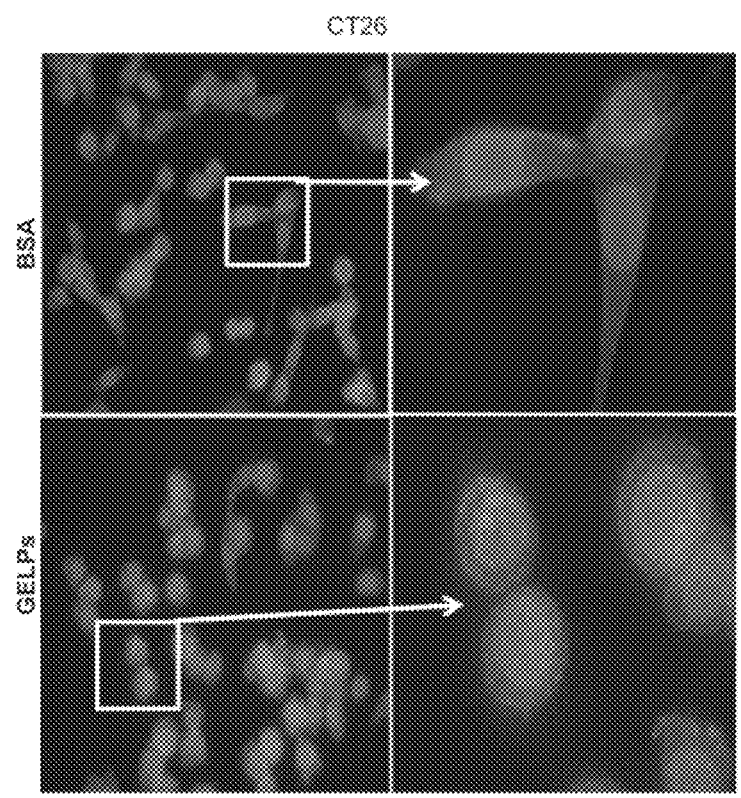
Figure 7E:
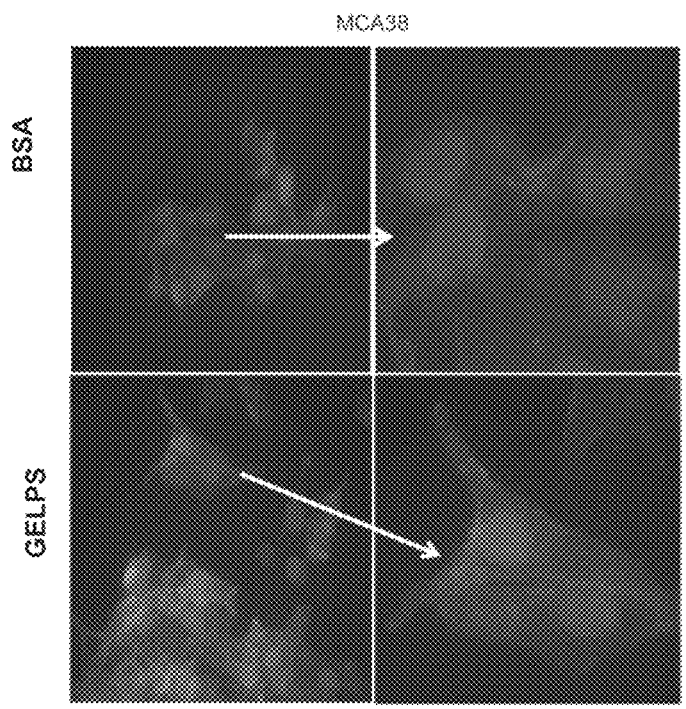
Figure 7F:
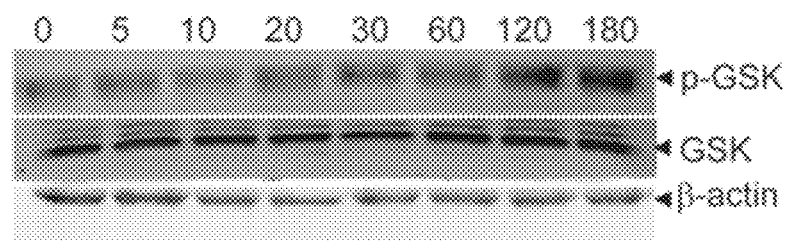
Figure 7G:
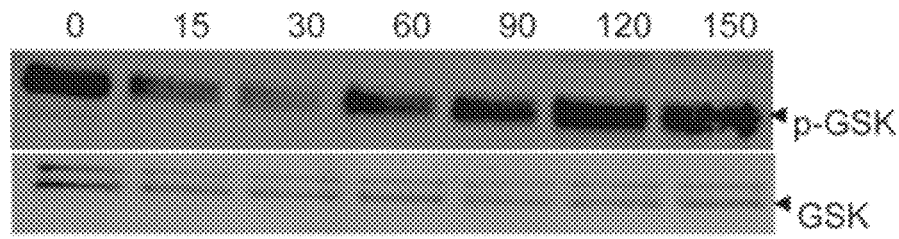
Figure 8A:
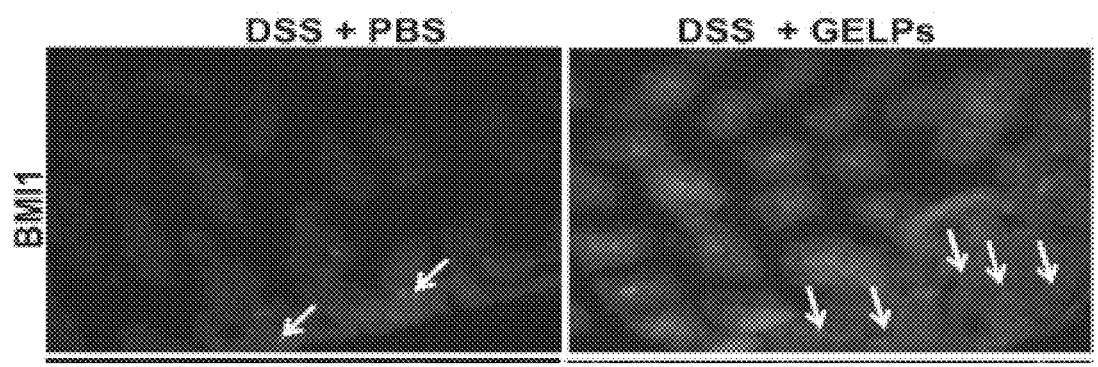
FIGS. 8A-8C are images showing the induction of BMI1 positive stem cells in the intestine of mice gavaged with GELPs, including: images showing BMI1 positive stained cells (FIG. 8A) or BRDU+proliferative cells (FIG. 8B); and an image showing a representative haematoxylin and eosin staining of crypts from PBS or GELP gavaged mice (FIG. 8C)
Figure 8B:
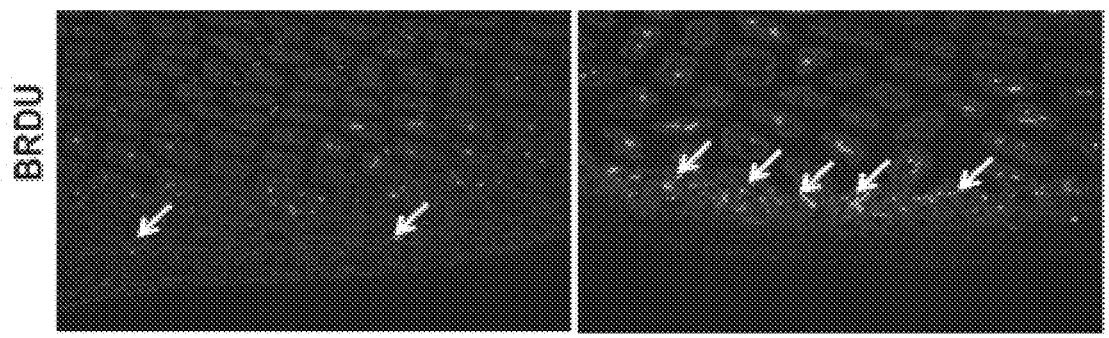
Figure 8C:

Next, it was determined whether GELP treatment effected the localization of β-catenin in intestine epithelia. It is appreciated that activation of the Wnt-β-catenin pathway promotes the regeneration of epithelial cells after DSS induced intestinal injury, including stem cell regeneration. In this regard, it was hypothesized that GELP accelerated that regeneration process by enhancing β-catenin mediated activation of the Wnt-β-catenin pathway. One of the initiating events of activating the Wnt-β-catenin pathway is nuclear translocation of β-catenin, so, to determine whether GELP treatment had effects on the translocalization of β-catenin in intestinal epithelium, the localization of intestinal β-catenin was analyzed in PBS-versus GELP-treated mice Immunostaining of sections from these mice 7 days after being provided 3% DSS in drinking water showed β-catenin stains much stronger in the cytosol and nucleus of mice treated with GELP than in mice that received PBS (FIGS. 7A and 7B). Induction of phosphorylation of GSK3β is required for translocation of β-catenin from the cell membrane to the nucleus. Next, it was tested whether GSK3β is phosphorylated after mice were treated with GELPs. The results of western blot analysis showed that the phosphorylated form of GSK3β is induced in the small intestine of mice treated with GELPs (FIG. 7C). These in vivo results were further confirmed by immunohistological staining (FIGS. 7D and 7E) and western blot analysis (FIGS. 7F and 7G) of β-catenin in mouse colon cell lines, including CT26 (FIG. 7D) and MCA38 (FIG. 7E). The results indicated that β-catenin is translocated from the cell membrane into the cytosol and nucleus and that the phosphorylated form of GSK3β was induced when the cells were exposed to (iELPs but not PBS. Collectively, these results further indicated that GELP treatment led to the inactivation of GSK3β and caused β-catenin nuclear translocation in both in vitro as well as in vivo mouse models. This was believed to be important as β-catenin translocation is required for activation of the Wnt signaling pathway that plays an important role in generation of intestinal stem cells (ISCs), and ISCs are important for maintaining tissue homeostasis and replacing lost cells in response to tissue damage such as DSS induced epithelial cell damage Next, it was tested whether epithelial renewal driven by stem cells played a role in GELP-mediated protection of mice against DSS induced colitis. A polycomb transcriptional repressor family member (BMI1) has recently been identified as a specific marker of stem cells in epithelium. To investigate whether BMI1 expression is altered in the setting of colitis, C57BL/6 (WT) mice administered 3.0% DSS in the drinking water were gavaged with GELPS or PBS (as a control) every other day for 6 days. The mice were examined for levels and cellular localization of BMI1 and cell proliferation at day 7 after the treatments. In contrast to the expected BMI1 immunoreactivity, there was a generally very low frequency of BMI1-positive cells, which were usually found in the base region of the intestinal crypts (FIG. 8A, left), with no expression at the luminal surface. In contrast, there was a very obvious significant increase in the frequency of strongly BMI1-positive cells throughout the crypts of grape exosome gavaged mice (FIG. 8A, right). Increased levels of BMI1 correlated with an increase in BRDU incorporation in the same regions of the intestinal crypts (FIG. 8B) and an increase in cellularity in the base region of the crypts of HE stained intestinal tissue sections (FIG. 8C). These results indicated that GELP treatment led to the promotion of intestinal epithelial cell proliferation and the cells were likely to be BMI1 positive stem cells.

Example 8—Use of Fruit-Derived Exosomes as a Noninvasive Detection Method for Colon Cancer-Associated Inflammation Colorectal cancer (CRC) is the second leading cause of cancer mortality in the United States, and the third most common type of cancer in men and women. Diagnosis of CRC indicating lymph node metastasis, is associated with poor survival rates, demonstrating the necessity for early detection. Currently, the most commonly used screening techniques are fecal occult blood testing (FOBT), sigmoidoscopy, colonoscopy, and computed tomographic (CT) colonography, all of which possess both advantages and disadvantages. All of these methods either fail to detect most early precancerous polyps and cancerous lesions or are very invasive. In addition, these methods are both time- and cost-intensive and require substantial expertise. Based on the results described below, it was found that using DIR dye labeled GELP is useful for identification of CRC in the early stages of disease or even before disease onset, thus allowing for both the elimination from expensive therapeutic studies, as well as the assessment of therapeutics at various stages of disease.

Figure 4:
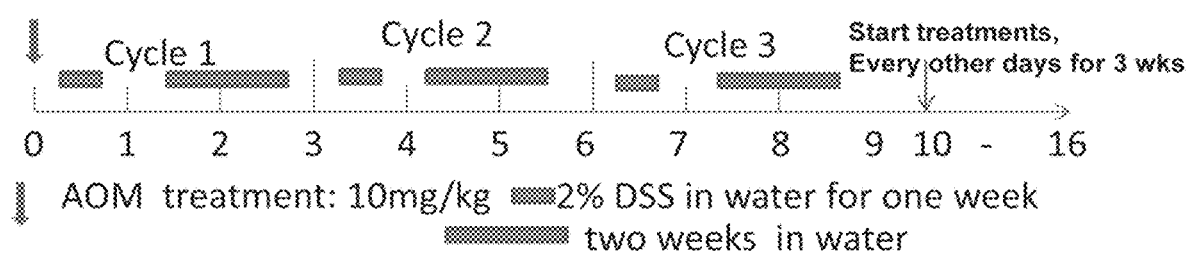
FIG. 4 is a schematic diagram showing the protocols used for investigating colon carcinogenesis, where 7-week old female C57BL/6j mice were given a single dose of AOM (10 mg/kg/body wt) or PBS as a control by oral gavage and on the same day, mice were provided 2% DSS in their drinking water for 7 days, followed by 2 weeks of untreated water, where the cycle was repeated two more times for a total of three cycles, and where, at the beginning of week 10, mice were treated with GFELP-Cur, GELP-Cur, or Cur every other day for three weeks.
Figure 9A:
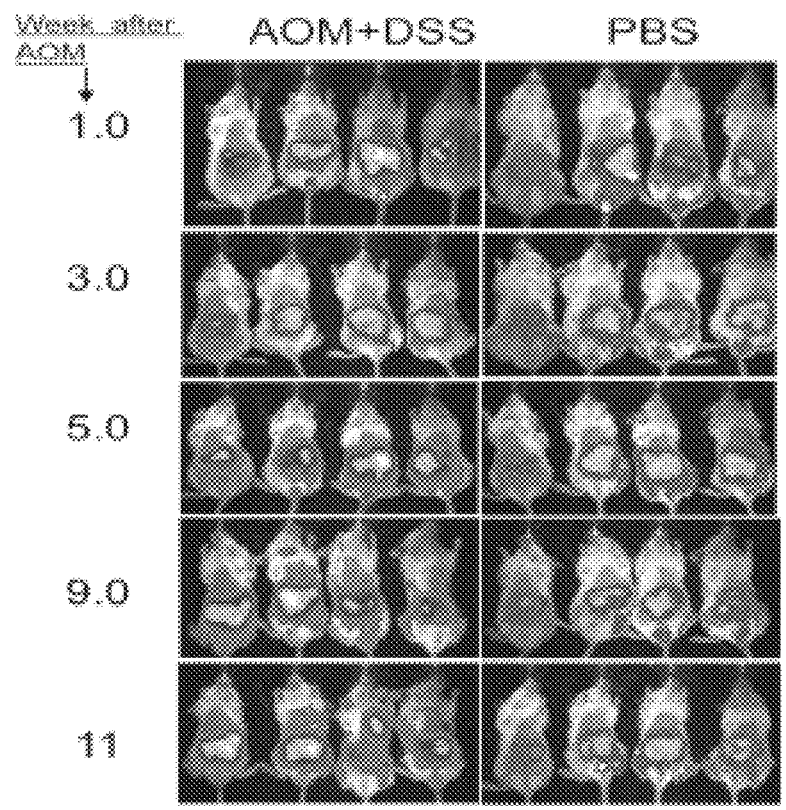
FIGS. 9A-9B include an image and a graph showing the use of DIR dye-labeled GELPs as an early indicator for AOM induced intestine leisure, including: representative photographs from PBS or AOM injected mice (FIG. 9A); and a graph showing the signal intensities in the intestine of AOM injected mice as determined by measuring the numbers of photons collected from AOM injected mice divided by the number of photons collected from PBS injected mice (FIG. 9B)
Figure 9B:
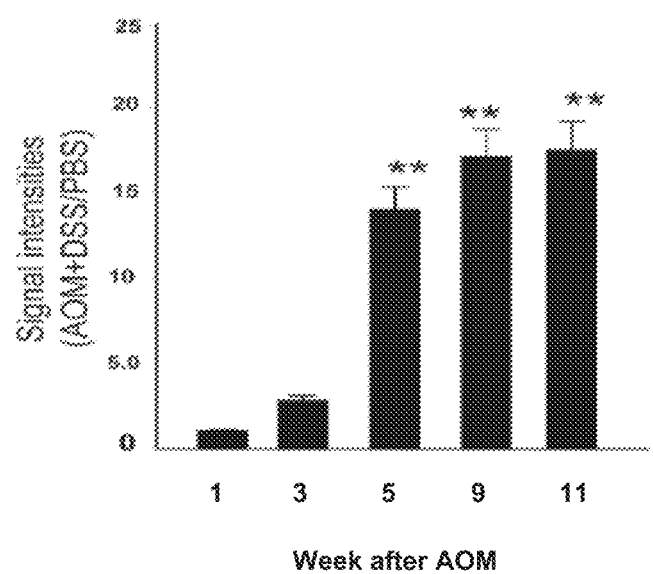

Briefly, in these studies, mice received a single injection of azoxymethane (AOM, 10 mg/kg body weight) or PBS (as a control), followed by administration of three cycles of dextran sulfate sodium (DSS, 2% in water) as outlined in FIG. 4. Mice (8 mice/group) were imaged at week 1.0, 3.0, 5.0, 9.0 and 13.0 weeks after the AOM administration using a Carestream Molecular Imaging System (Carestream Health, Inc). Mice were anesthetized with 2% isoflurane in oxygen through a nose cone during the imaging. Body temperature was supported with warm air circulating in the magnet bore (SA Instruments, Inc, Stony Brook, NY). Immediately after the imaging, mice were killed and carefully dissected without disturbing the position of abdominal contents in situ, and then examined for macroscopic tumor formation. The results showed that macroscopically visible tumor was not evident until week 11. In contrast, starting at week 5 after AOM administration, mice gavaged with DIR-dye labeled GELP have a much stronger signal in the colon than of PBS control mice (FIGS. 9A and 9B).

Example 9—Clinical Investigation of GELP-Cur Treatment for Rheumatoid Arthritis

To investigate the safety of GELP-Cur treatment for rheumatoid arthritis (RA) patients and to generate data in support of conducting a large clinical trial. An initial clinical trial is performed. Eligible patients must meet the most recent American College of Rheumatology (ACR) criteria for rheumatoid arthritis, be at least 18 years of age, and have had clinical features of RA for less than 12 months. To be included, patients will have had an inadequate response to disease-modifying antirheumatic drugs (DMARDs) including anti-TNF-α therapy, after at least three months of such treatment. Patients must have 5 or more swollen joints and/or tender joints at the time of enrollment. Changes in the doses of background DMARDs will not be permitted except to avoid adverse effects. Forty-five patients are enrolled for a pharmacokinetics and safety study using GELP-Cur treatment with each dose as described in Table 1 below.

TABLE 1

| Dosing guidelines |
|---|
| 1. If no one in a cohort of 15 patients (pts) treated with 5 mg/kg of body weight experiences side effects (SE), the dose will be doubled for the next cohort. |
| 2. If 1-2 of a cohort of 15 pts experiences SE, the dose will remain the same for the next cohort as the first cohort. |
| 3. If 3 or more of 15 pts experience SE, the dose will be reduced to 2.5 mg/Kg of body weight for the next cohort. |
| 4. If 4 or more pts out of 30 consecutive pts (2 cohorts of 15 pts each, all at the same dose) experience SE, the dose will be reduced to 2.5 mg/Kg of body weight for the next cohort. |

Patients who have allergies to curcumin or grapes, and patients taking drugs that are known to interact with grape juice are excluded. Patients are educated on food sources of curcumin and asked to avoid all foods containing high concentrations of curcumin within the 14 d before GELP-Cur administration. Subjects complete a food checklist to verify that they are not consuming any curcumin-rich foods before dosing.

The curcumin for the study is purchased from Sabinsa Corp. (Piscataway, NJ), which has also furnished the material for several other clinical trials, including a recent pancreatic cancer trial conducted at M. D. Anderson Hospital, Houston, TX The GELP-Cur is prepared under GLP protocol by qualified personnel. The GELP is prepared using gradient centrifugation as described previously. The GELP is resuspended in sterile 0.9% NaCl and the concentration of GELPs is determined by analyzing protein concentration using the BioRad protein quantitation assay kit with BSA serving as the standard. Quality control procedures include the precautions described previously, and analysis of potential contamination of the exosomes during the purification process by assessing endotoxin levels using the Limulus amebocyte lysate assay (Associates of Cape Cod, Inc.). In addition, the composition of the GELP is analyzed by HPLC to monitor the presence of flavinoids and other potentially bioactive molecules in the GELPs. Two-dimensional gel electrophoresis is used to generate a protein signature for quality control purposes.

The GELP-Cur is then prepared by mixing curcumin with a standardized amount of GELPs in 0.9% NaCl. After incubation at 22° C. for 5 min, the GELP-Cur is separated from unbound curcumin by centrifugation and lyophilized. The concentration of curcumin in the GELP-Cur is determined by HPLC analysis and the biological activity of the GELP-Cur analyzed by measuring inhibition of TNF-α and IL-6 production after LPS stimulation of a macrophage cell line (RAW264.7). Aliquots are stored at −20° C. and administered to patients immediately after suspension in drinking water.

Curcumin used for patients is seldom administered in a pure chemical form. Rather, it typically consists of three separate curcuminoids composed of curcumin itself, as well as demethoxycurcumin and bisdesmethoxycurcumin. To determine the qualitative and quantitative presence of these curcuminoids in the GELP-Cur product as prepared and described above and to be used for this clinical trial, the GELP-Cur material is separated using a Gemini 5 um C18 (2×100 mm) analytic column (Phenomenex) and a linear acetonitrile/methanol/0.2% formic acid gradient. The amount of curcuminoid is detected using a Waters Quattro Ultima tandem mass spectrometer equipped with electrospray-positive ionization capability in the mass spectrometry facility of University of Louisville. All three compounds are quantified using standard calibration curves prepared from reference standard materials obtained from Sigma-Aldrich. Calibration curves are prepared by making a 1 mg/mL stock solution of the authentic materials in methanol and then serially diluting the stock solutions to 1,000, 500, 100, 50, 10, 5, and 1 ng/mL in 50:50 methanol/0.2% formic acid. Calibration curves are then prepared using the mass spectrometry quantification software program.

For the GELP-Cur treatment of patients, the study design is based on a conventional "15+3" dose-escalation model, with patients receiving oral GELP-Cur daily, at a dose of 5 mg/kg of body weight, beginning on the day of enrollment until day 180. Each subsequent cohort will receive a dose of GELP-Cur determined by the guidelines in Table 1. A maximum dose of 20 mg/kg of body weight will be pre-selected during the design of the study because this is within the safety dose of curcumin that has been used in clinical trials. Study medication is administered orally daily for up to 6 months. Subjects take the dose with 8 fl. oz. of water.

All clinical assessments are performed at the University of Louisville Hospital. Blood and urine samples are collected at 0 (immediately preceding GELP-Cur administration), 6, 12, and 24 hours post-dose and before a second dose. The procedure is repeatedly applied to a second and third escalated dose. Serum and urine concentrations of curcumin are determined using methods described previously. Steady-state pharmacokinetic parameters are determined, i.e., maximum observed plasma concentration (Cmax), minimum observed plasma concentration (Cmin), average observed plasma concentration (Cav), area under the plasma concentration-time curve from 0 to 24 hours ($AUC_{0-24}$), and time to Cmax (tmax). These primary model variables are estimated using SAS PROC NLINMIXED (SAS Institute), from which estimates of area under the curve (AUC), Tmax, Cmax, and tin, will be derived.

Safety is assessed by occurrence of adverse events (AEs) as listed in Table 2 below and by monitoring of biochemical, hematological and urinalysis parameters every month during the study period, with toxicity graded according to the Common Toxicity Criteria version 3.0. Adverse events, such as gastrointestinal complaints, vomiting, anorexia, headache, dizziness, insomnia, fever, and mouth ulcers are included. For assessing the safety of the treatments, patients are monitored monthly for AEs, serious AEs, and clinically significant changes in vital signs and laboratory tests at each monthly visit during the study duration. Both the severity of AEs and their relation to the study treatment are noted by the investigator. In addition, standard parameters are evaluated in serum, urine and whole blood of all patients. In addition to standard safety parameters, samples are collected for phenotyping leukocyte subsets by FACS. Phenotyping includes neutrophils, macrophages, and T cells. The inflammatory cytokines IL-6, IL-8, IL-10 and TNF-α are analyzed using a standard ELISA. Patients also are monitored for tolerability and efficacy at monthly intervals from the start of dosing through the completion of the study, as well as at a follow-up visit 6 months after completion of the study.

TABLE 2

| Lists of adverse events: |
| --- |
| General: weight loss, fatigue, sweating |
| Gastrointestinal: Nausea, vomiting, abdominal pain, diarrhea |
| Skin: Rash, pruritis, alopecia, oedema, flush, haematoma, erythema, dermatitis |
| Neuropsychiatric: Psychiatric, sleep disturbance, headache, dizziness, ENT/opthalmological |
| Others: Stomatitis/mouth ulcers, altered taste, blurred vision, Infections: Urinary tract infection, respiratory infection Other infection with fever |

There are two end points determined at six months: the proportion of RA patients with an ACR 20 response; and the proportion of patients with an improvement of at least 0.3 from baseline in the Health Assessment Questionnaire (HAQ) disability index (exceeding the minimal clinically important change of 0.22). An ACR 20 response indicates a decrease of at least 20 percent in the number of both tender and swollen joints, as well as a 20 percent improvement in at least three of the following: the patient's global assessment of disease activity; the patient's assessment of pain; physical function, as assessed by the HAQ disability index; the physician's global assessment of disease activity; and the C-reactive protein level. Secondary objectives include a 50 percent and 70 percent improvement in the ACR response at six months. Changes in disease activity are assessed with the use of the Disease Activity Score 28 (DAS28). Clinical remission is defined by a DAS28 of less than 2.6, and a low level of disease activity will be defined by a DAS28 of 3.2 or less. The mean improvement in physical function at six months is based on the change from baseline in the HAQ disability index. Changes from baseline in the health-related quality of life will be assessed by the Medical Outcomes Study including physical function, pain, general and mental health, vitality, social function, and physical and emotional health.

Various parameters of serum biochemistry, hematology and urine analysis are carried out on each evaluation day. Serum samples are collected on all evaluation days for quantification of pro-inflammatory modulators. If feasible, knee joint synovial fluid is collected aseptically at baseline and at day 180 for evaluation of MMPs and inflammatory cytokine concentrations.

All AEs are reported in a tabular format with the following headings: AE description, AE onset and stop date, grade, relationship to study drug, action, action comments, and outcome. This format enables a thorough review of events and possible causality to ensure the safety of patients enrolled in the trial.

To investigate a potential correlation between blood and joint concentrations of curcumin and anti-inflammation activity, plasma and swollen joint fluid samples are collected over the course of the study for pharmacokinetic profiling of curcumin. In period 1, blood and synovial fluid curcumin pharmacokinetic samples are taken on days 1 and 7. In period 2, blood and synovial fluid curcumin pharmacokinetic samples are collected on day 14, and additional pharmacokinetic samples for curcumin determination are obtained on days 28, 90 and 180.

Standard safety parameters including blood count, serum chemistry panel, and urinalysis will be determined. Concentrations of curcumin in plasma and urine samples are collected monthly and detected using a high-performance liquid chromatography (HPLC)-based method with UV detection as described previously. Assay precision and accuracy are determined via analysis of a standard curcumin control with more than 97% purity. Concentrations of curcumin in the samples are determined by comparison with a standard curve of curcumin.

Various parameters of serum biochemistry, hematology, urine analysis, and bone erosion by radiography are carried out on each evaluation day. Serum samples are collected monthly for quantification of pro-inflammatory modulators and rheumatoid factor. Knee joint synovial fluid is collected aseptically at baseline and on days 28, 90, and 180 for evaluation of MMPs and inflammatory cytokine concentrations. Samples are collected for phenotyping leukocyte subsets by FACS, including neutrophils, macrophages, and T cells. The inflammatory cytokines, i.e., IL-6, IL-8, IL-10 and TNF-α, are also analyzed using a standard ELISA as described previously.

The trial is designed to have more than 80% power to detect a situation in which GELP-Cur treatment yields an improvement of at least a mean change of +0.9 standard deviation in comparison with before treatment. Under this conservative assumption, differences between groups in mean improvement are tested using ANOVA (0=0.05, two-sided). With 45 patients, a 95% confidence of observing at least one example of any side effect occurring in 10% or more of the patient population with a specific treatment is expected.

For the primary analyses of the AEs, ACR 20 and HAQ responses, the proportion of patients who have a response are summarized according to the treatment group. A two-sided Cochran-Mantel-Haenszel chi-square test is used to compare response rates among treated groups at the 0.05 level of significance. For the analyses of AEs, ACR 20 and HAQ responses, all patients who discontinue treatment are subsequently considered not to have a response. The primary and the multiple secondary end points are tested in a pre-specified sequence after the use of a closed testing procedure, thus controlling overall for type I error rate at the 0.05 level. All reported P values are two-sided. Mean changes from baseline in the DAS28, HAQ disability index, and the scores for the physical- and mental-component summary scores of the SF-36 are compared between treatment groups with the use of an analysis of covariance after adjusting for the baseline assessments. Safety is evaluated according to the frequency of AEs, changes in laboratory values, and abnormal clinical findings. P values for safety comparisons are obtained with the use of a chi-square test or, where appropriate, Fisher's exact test.

Based on initial data and current literature, toxicity or severe side-effects are not anticipated. If side effects are observed in RA patients treated with GELP-Cur at the proposed lowest dose (5 mg/kg), a lower dose than 5 mg/kg of GELP-Cur is used. Lower doses should still have therapeutic effects since 1 uM of curcumin encapsulated in GELP induced apoptosis in more than 50% of human monocytes (FIG. 10). Also, the concentration of curcumin in RA patients treated with GELP-Cur is expected to remain high during the 24 hour period after treatment. If this is the case, RA patients may not need daily treatments with GELP-Cur. Based on the data expected to be generated from the pharmacokinetics study of GELP-Cur treatment, the frequency of taking GELP-Cur may be reduced which would further minimize any potential side-effects. Additionally, a reverse correlation between joint concentration of curcumin and disease activity is expected, and it is further anticipated that the data indicates whether a particular subset of RA patients is more (or less) responsive to treatment with GELP-Cur than other subsets of patients. However, as curcumin affects many pro-inflammatory pathways, it is anticipated that a large group of the patients are responsive. For example, RA patient's refractory to anti-TNF-α therapy may have a similar response to GELP-Cur as non-refractory RA patients. Since macrophages are one of the major sources of TNF-α and other inflammatory cytokines, RA patients who are resistant to TNF-α treatment may develop a TNF-α independent pathway(s) that contributes to the progression of inflammation in RA. Using a GELP-Cur strategy will eliminate these macrophages, regardless of which inflammatory cytokines are released.

Figure 10A:
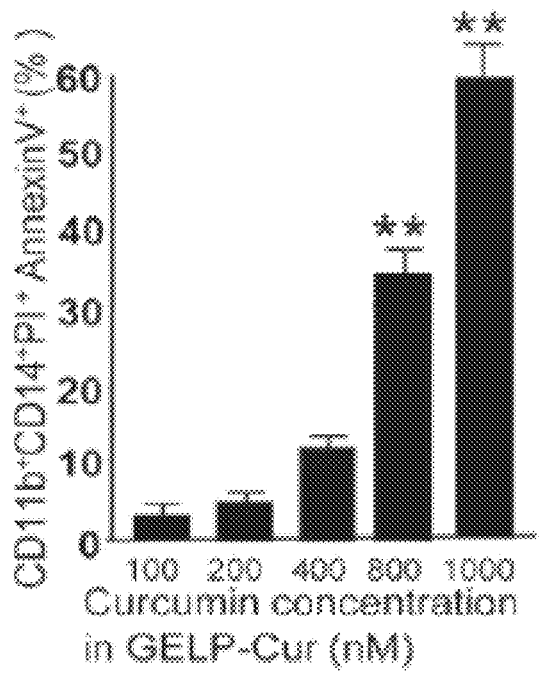
FIGS. 10A-10B include graphs showing the ability of lower concentrations of curcumin encapsulated in the GELPS to not induce apoptosis of human monocytes and to suppress T cell proliferation, including: a graph showing the results of FACS analysis of CD11b+PI+AnnexinV+ cells (FIG. 10A); and a graph showing the extent of T cell proliferation as was measured by $^3$H-thymidine incorporation in GELP-Cur treated mice (FIG. 10B)
Figure 10B:
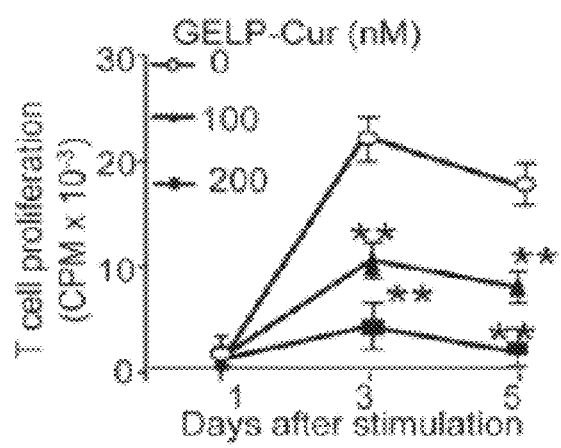
Figure 11:
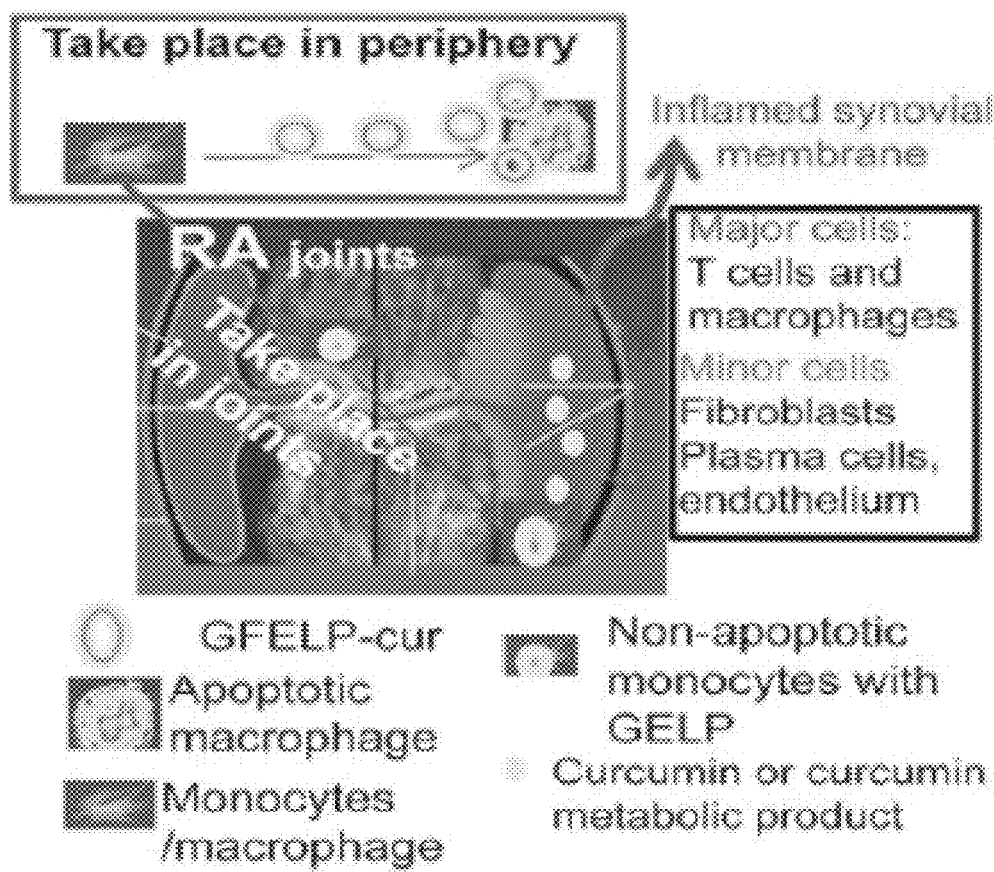
FIG. 11 includes a schematic diagram showing a model used to test whether oral GELP-Cur treatment of rheumatoid arthritis patients is safe and leads to selective induction of monocyte apoptosis and subsequent attenuation of RA progression, and to test whether monocytes taking up less GELP-Cur nanoparticles result in the accumulation of curcumin or its metabolic products in inflamed joints and further inhibit the proliferation of other infiltrating immune cells.

Based on the data generated from the mouse model, it is thought that the therapeutic effect is due to elimination of activated monocytes and macrophages. Other types of immune cells also play a role in the pathogeneses of RA; however, the fact that monocytes preferentially migrate into inflamed joints in RA patients allowing for the release of curcumin and/or its metabolic products locally in the joints where the infiltrating autoreactive T cells, B cells and neutrophils accumulate are utilized. Theoretically, this would suppress the activities of these autoreactive cells. This suppression is increased as treatment continues due to the accumulation of curcumin and/or its metabolic products in the joints. Initial data support the hypothesis that lower doses of GELP-Cur (200 nM) do not cause apoptosis of CD14+ cells isolated from peripheral blood of healthy subjects. FACS assay of Annex V- and PI-stained cells showed no effect on the viability of cells treated with 200 nM of GELP-Cur (p=0.002) (FIG. 10A). Furthermore, co-culture of these cells pretreated with GELP-Cur (200 nM) with T cells (5:1) suppressed T cell proliferation (FIG. 10B). In RA patients who are administered GELP-Cur orally, non-apoptotic monocytes (due to carrying less GELP-Cur) migrate to inflamed joints, where curcumin is released and T cell, B cell and neutrophil activities are subsequently suppressed as illustrated in FIG. 11. If this hypothesis is true, it should be observed that the concentration of curcumin is increased as the GELP-Cur treatment is prolonged. This hypothesis is tested as follows: (a) FACS analysis of the number of CD14+ and CD6S+ cells with intracellular staining of TNF-α or IL-6 in synovial fluid of RA patients receiving GELP-Cur will significantly be reduced as the GELPs-Cur treatment is prolonged. These data are correlated with a reduction of disease progression based on ACR20, ACR50 and ACR70 scores; (b) Curcumin and curcumin metabolic products in the synovial fluid are increased as the treatment is prolonged; (c) it is anticipated that the percentage of RA patients who response to GELP-Cur treatment increase since this strategy not only applies to macrophage dependent RA patients but also to T cell, B cell and neutrophil dependent RA patients; and (d) using FACS analysis of CD4/CD69/IL-2/Ki-67/IFN-γ, CD19/Ki-67/BAFF-R/TACI, CD11b/TLRs, the numbers of activated T cells, B cells and neutrophils in the synovial fluid are expected to decrease in the RA patients receiving GELP-Cur.

Without wishing to be bound by any particular theory or belief, it is thought that the proposed studies indicate a viable alternative exists for the development of a non-invasive fruit-derived system for the delivery of curcumin and other drugs, as well as multiple drug carriers. The results provide a novel means to eliminate/reduce chronic inflammation in inflammatory tissue and would yield a new, cost-effective, and practical therapeutic method for treatment of inflammatory-related diseases including inflammatory RA patients; thus improving the health status of this patient population. Systemic inhibition of inflammation using drugs such as etanercept (Enbrel) (a soluble TNF receptor), infliximab (Remicade), and adalimumab (Humira) (anti-TNF antibodies) can result in severe adverse side effects and are costly. Hence, orally active blockers of inflammation that are safe, efficacious and inexpensive are urgently needed.

One of purposes of the study is to examine the efficiency of using curcumin as an alternative to pharmacological management of chronic musculoskeletal pain. The proposed study evaluate the safety and toxicity of grape exosomes carrying curcumin (GELP-Cur) as a treatment in patients with active RA, and further identifies which subset population of RA patients is more response to treatment with GELP-Cur. The outcomes from this study will further support the rational for a potentially larger clinical trial to treat both OA and RA patients. The success of the novel approach also sheds light on using fruit-derived exosomes for carrying other complementary and alternative agents, such as resveratrol (similar poor solubility as curcumin), to target inflammatory cells.

Moreover, the proposed study leads to a larger clinical study for the following reasons: (1) the study as proposed leads to the identification of a subset of RA patients who do not respond, or only partially respond to DMARD treatment, and who can be effectively and safely treated with GELP-Cur. The results generated through the study also are used as a basis for selecting a larger population of RA patients who are resistant to current treatments, and also permit longer safety trials. Although a number of immunomodulatory agents other than anti-TNF-α therapy have shown efficacy in patients with RA, the other agents are associated with a dose-dependent risk of gastrointestinal, cardiovascular, hematologic, hepatic, and renal adverse events.

Example 10—Analysis of Fruit-Derived Exosomal-Like Particles for Nucleic Acid Delivery Artificial systems including liposomes have been developed for the delivery of transgenes to mammalian cells in vitro and in vivo. However, all of the methods developed to date have too low of a transfection efficacy in vivo and in vitro or they are cost prohibitive for gene therapy use in clinical practice. Based on the results described below, it has been found that using grapefruit-derived liposomes is effective for delivery of nucleic acids in both in vitro cell-culture systems and in vivo. The in vivo delivery is successful when done repeatedly even in the presence of sera. This technology eliminates the need for expensive therapeutic studies as well as the assessment of high transfection efficiency without causing cytotoxicity. More specifically, the in vitro studies show that grapefruit-derived liposomes composed of optimized ratios of lipids (phosphatidylethanolamine, phosphatidylcholine, phosphatidylserine, monogalactosyldiacylglycerol (MGDG), and digalactosyldiacylglycerol) result in higher transfection efficacy than any of the other popular transfection agents on the market, including LIPOFECTAMINE® 2000 (Invitrogen) and FuGENE® HD (Roche). Furthermore, unlike other transfection agents, grapefruit-derived liposomes do not cause any detectable cytotoxicity and the presence of sera does not interfere with transfection efficiency. Also important is the fact that the methodology is much less expensive (less than $0.01/per reaction versus $3.50/reaction for current commercial products, calculated based on the cost for the transfection of one 6-well plate). Therefore, the methodology and resulting product could be used much more efficiently and economically for the in vitro and in vivo delivery of siRNA, miRNAs and mammalian expression vectors for gene therapy without causing non-specific cytotoxicity.

In these studies, grapefruit exosomal and microparticle lipids were first extracted. In brief, 10 mg of grapefruit exosomes or microparticles were suspended in 3 ml of preheated (75° C.) isopropanol containing 0.01% BHT (butylated hydroxytoluene, e.g., Sigma). After 15 min of incubation, 1.5 ml of chloroform and 0.6 ml water were added to the reaction, the mixture vortexed; and then agitated (shaking incubator) at 22° C. for 1 hour at which time the lipid extracts were transferred with glass Pasteur pipettes to glass tubes with Teflon-lined screw-caps. Four ml of chloroform/methanol (2:1) containing 0.01% BHT was then added to each tube and the mixture shaken for 30 min. This extraction procedure was repeated 5 times. One ml of 1 M KCl was added to the combined extracts, the mixture vortexed or shaken, centrifuged, and the upper phase discarded. Two ml of water was then added, the mixture vortexed or shaken, centrifuged, and the upper phase discarded. Tubes containing the lipid extract were then filled with nitrogen gas, stored in a freezer until transported on dry ice to the KLRC Analytical Laboratory for MS/MS identification of lipids.

Upon obtaining the results, it was found that the lipid analysis data indicated a similar composition of grapefruit exosomes and microparticles, i.e., similar ratios of phosphatidylethanolamine (PE):phosphatidylcholine (PC):phosphatidylinositol:phosphatidylserine:monogalactosyldiacylglycerol:digalactosyldiacylglycerol:LysoPC:LysoPE=35:35:10:3:5:2:2:2).

To then produce grapefruit exosomal or microparticle liposomes that deliver siRNA and mammalian expression vectors, two ml of grapefruit exosomes or microparticles in PBS were transferred into a glass vial, 7.5 ml of $CHCl_3$ added, the mixture vortexed for 1 min, 2.5 mil of MeOH added, the mixture vortexed again, and finally 2.5 mil of water added. The mixture was then centrifuged at 500×g for 10 min at 22° C. and the lower phase carefully collected. The extracted sample was subsequently dried at 100° C. under N2 gas, and the dried lipids were dissolved in 100 µl $CHCl_3$ and transferred to a glass bottle. The lipid was dried as before, and siRNA, miRNAs or mammalian expression vectors in PBS were added as experimentally desired, with the mixtures being sonicated in a water sonication bath for 40 min to prepare the samples for transfection of cells.

For the cell culture, the 4T-1 cell line, murine mammary adenocarcinoma of spontaneous BALB/c origin, GL-26 murine microglioma tumor cells, CT26 murine colon cancer cell lines, RAW 264.7 murine macrophage, A549 human lung carinonoma cell line, MDA-MB-231 human breast cancer cell line, and 293 human kidney cell line were purchased from ATCC and maintained in vitro at 37° C. in a humidified 5% $CO_2$ atmosphere in air in complete medium (Dulbecco's modified Eagle's medium with 10% fetal bovine serum) as described previously. The fetal bovine serum used in cell cultures was exosome depleted by differential centrifugation using a method described previously.

The DNA plasmid, pEGFP expressing green fluorescent protein with cytomegalovirus promoter was purchased from Clontech (Palo Alto, CA). The plasmid was purified using a Qiagen (Valencia, CA) kit according to the manufacturer's instructions. The plasmid purity was assessed by measuring the $A_{260}/A_{280}$ ratio and confirmed by agarose gel electrophoresis. siRNAs including luciferase siRNA and scramble siRNA were purchased from Ambion Inc.

To transfect the cells, the cells were seeded at a density of $2 \times 10^5$ cells per well onto 6-well plates (Nunclon) in 2-ml growth medium. At 24 h of culture time the cells were about 80% confluent and used for transfection. The grapefruit-derive liposome/DNA complexes or the grapefruit-derived liposome/siRNA complexes prepared as described above were then added to the media drop by drop up to a volume of 100 µl. Plasmid DNA (4 µg/well) or siRNA (1 µg/well) was used.

To transfect primary spleen T cells, spleen T cells obtained from C57BL/6j mice were isolated. Purity of the spleen T cells was routinely between 95 and 98% as determined by flow cytometry. Total T cells were transfected with 4 µg of plasmid DNA at a cell density of $1 \times 10^7$ cells per 100 µl of solution using FuGENE® HD, LIPOFECTAMINE® 2000, or grapefruit liposome methodology. After transfection, cells were transferred immediately into prewarmed RPMI1640 culture medium supplemented with 2 mM glutamine, penicillin (100 U/ml), streptomycin (100 µg/ml), and 10% fetal calf serum in the presence of recombinant mouse interleukin-2 (50 u/ml) plus anti-CD3 (100 ng/ml). Forty-eight hr after the transfection, transfection efficiencies were determined by flow cytometry analysis of GFP cells.

48 hr after cells were transfected with a reporter plasmid encoding the GFP from either grapefruit liposome or two commercial reagents (FuGENE® HD and LIPOFECTAMINE® 2000), cells were detached from the culture well using PBS containing 0.02% EGTA and 1 µg/ml propidium iodide. Propidium iodide was included to identify the nonviable cells. The percentages of dead cells were determined by flow cytometry, evaluated with the Cellquest software (BD Biosciences, San Jose, CA). The percent cytotoxicity following transfection was calculated as follows: (number of nontransfected adherent or total number of cells when grown in suspension present at the time of harvest—the number of adherent or total number of cells when grown in suspension in the transfected sample at the time of harvest. The transfection efficacy was determined as the: number of EGFP positive cells/total numbers of cells.

GL26 murine microgliomas stably transfected with Lent-luc were also transfected with luciferase siRNA or scramble siRNA (Ambion) as a negative control. 48 hr after transfection, the cells were lysed with lysate buffer (Promega luciferase assay system kit, Madison, WI). Luciferase activity in each well was determined using a luminometer (Applied Biosystems, Foster City, CA) and the luciferase assay system kit (Promega) according to the instruction manual. The ratio of firefly luciferase activity of cells transfected with luciferase siRNA to scramble siRNA was calculated. An asterisk (*) indicates a p-value of less than 0.05 in a Student's t-test.

Figure 12A:
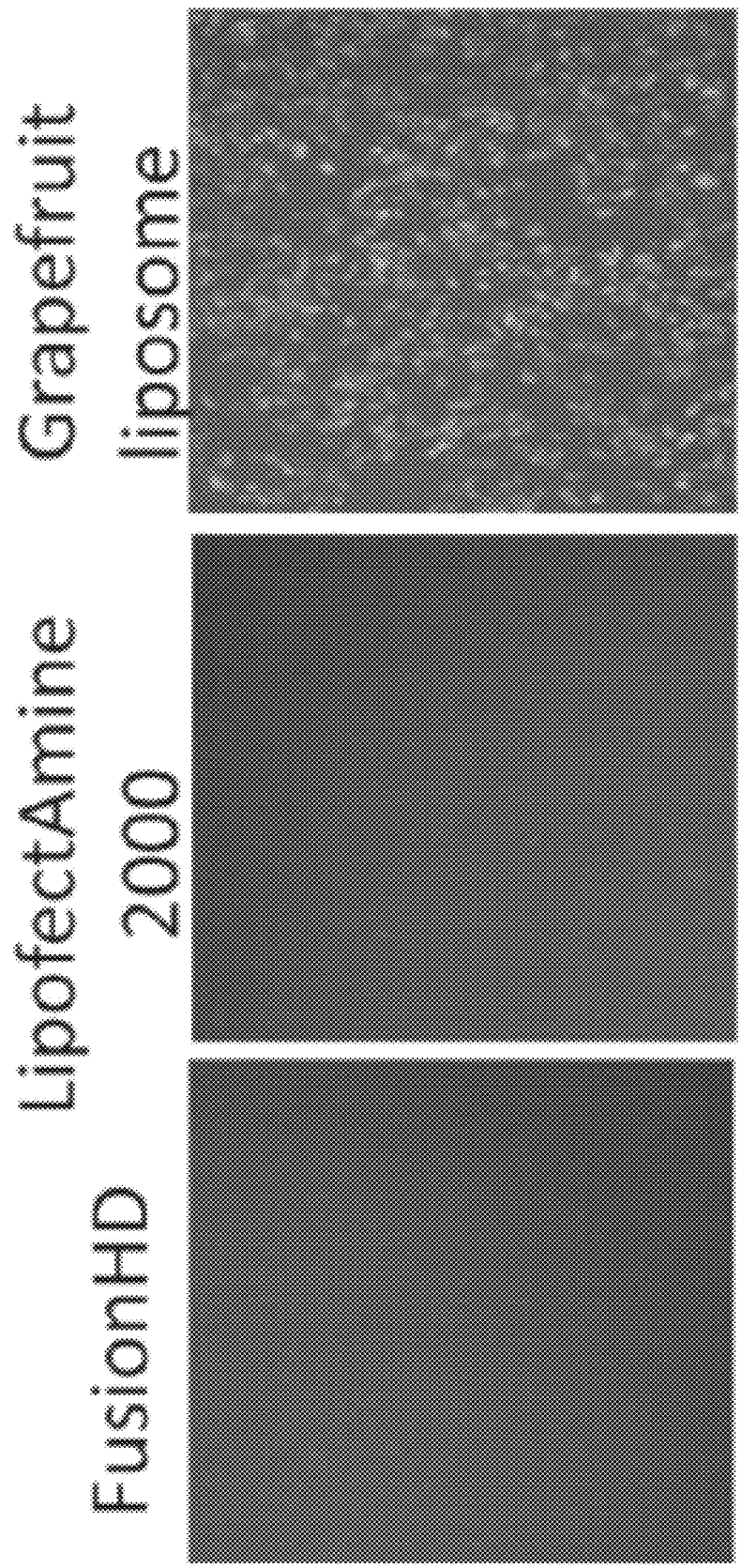
Figure 12B:
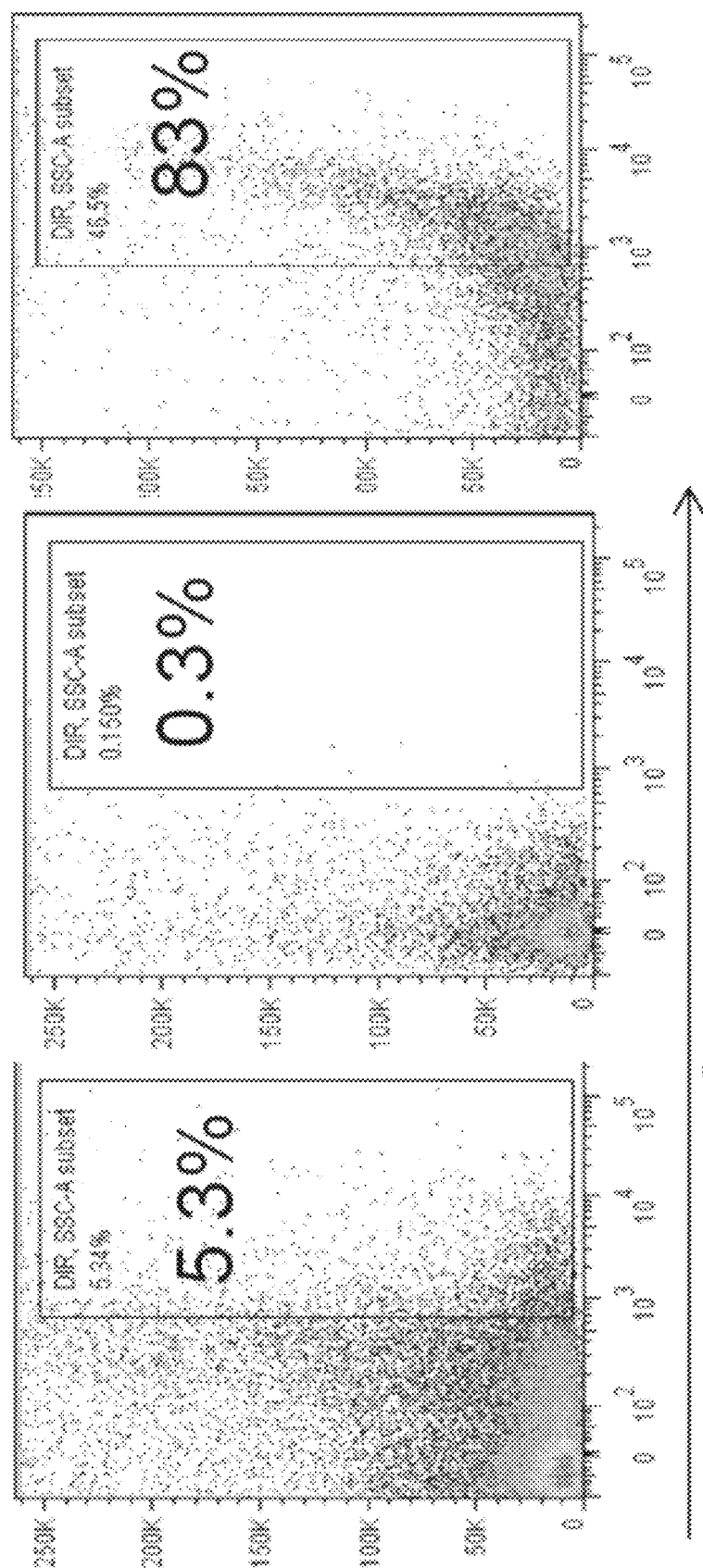

The ability to transfect primary immune cells opens up many possibilities for the study of disease and the development of therapies that modulate the host immune response. However, there is no agent available to effectively transfect primary immune cells, in particular T cells. Lentiviral vector has potential to be used as a delivery vehicle for T cells; however the major drawbacks of using lentiviral vector include insufficient transduction efficiency, putative aberrant expression near integration sites raising safety issues and the high cost for its production. The data obtained from the experiments described herein above indicate that grapefruit-derived liposomes, which consist of 100% natural components of this often consumed fruit, are effective and result in more than 80% transfection efficiency of GFP expression in primary T cells (FIGS. 12A-12C) isolated from B6 spleen with only 5% cytotoxicity. In comparison, only 5.3-0.3% transfection efficiency was achieved when FuGENE® HD or LIPOFECTAMINE® 2000 were used (FIGS. 12A-12C) and a higher cytotoxicity resulted (10-15%, FIG. 12D), respectively.

Figure 13A:
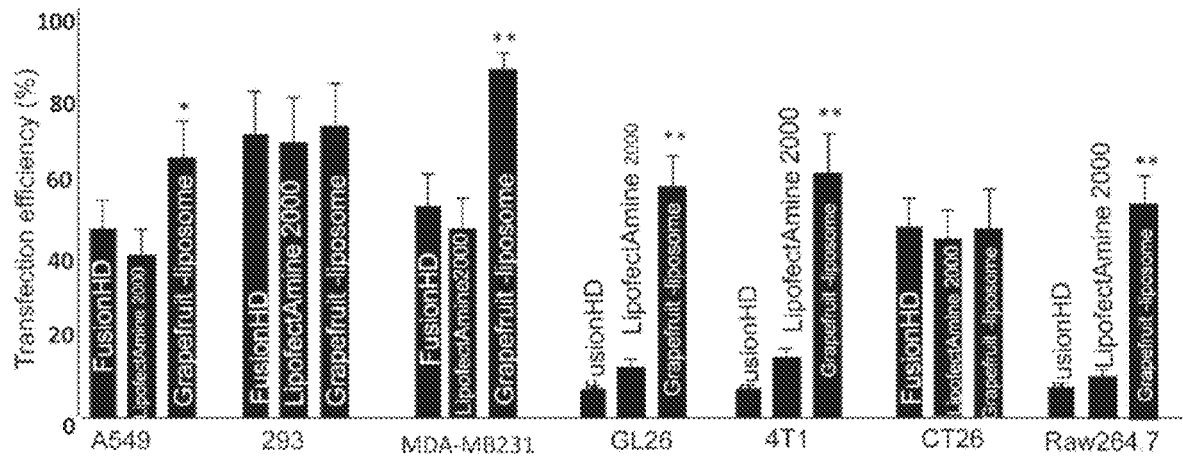
FIGS. 13A-13B are graphs showing the ability of grapefruit liposomes to transfect a broad spectrum of cell lines, including: a graph showing the transfection efficiency of the transfection agents, Fusion HD and LIPOFECTAMINE® 2000 (Invitrogen, Carlsbad, CA), and grapefruit liposome as measured by FACS analysis for GFP cells (FIG. 13A); and a graph showing the percent of cytoxocity in the transfected cells as measured by the extent of propidium iodide positive cells (FIG. 13B)
Figure 13B:
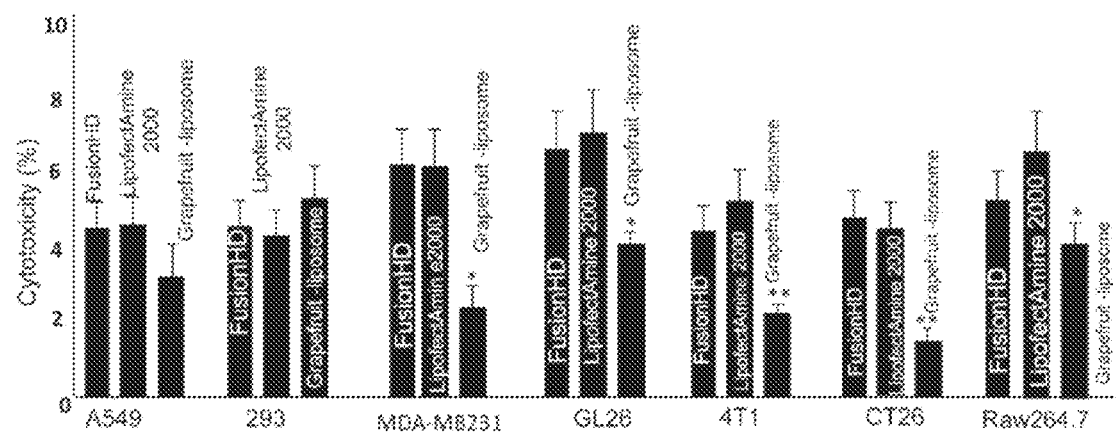

The transfection efficiency of other types of cells listed in FIG. 13A was also tested. Most of the cell types have a much higher susceptibility of being transfected with grapefruit liposome than with FuGENE® HD or LIPOFECTAMINE® 2000. This higher transfection efficiency with grapefruit liposomes was also associated with lower cytotoxicity (FIG. 13B). These results were though to not be due to poor quality of the other two transfection agents since all three agents have similar transfection efficiency in 293 cells.

Figure 14:
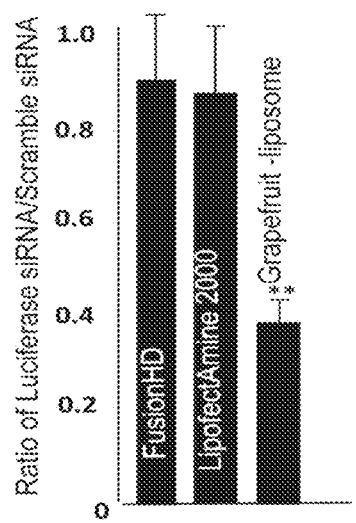
FIG. 14 is a graph showing the ability of grapefruit liposome to effectively deliver a siRNA, where GL26-Luc microglioma cells stably expressing a luciferase gene were transfected with either luciferase siRNA or scrambled siRNA (1 μg/well of a 6-well plate) using the transfection agents Fusion HD and LIPOFECTAMINE® 2000 (Invitrogen, Carlsbad, CA), or with grapefruit liposome.

To determine whether grapefruit liposomes were suitable for delivery of siRNA, the GL26 murine microglioma cell line stably expressing the firefly luciferase gene (GL26-luc) was used. The GL26-luc cells were transfected with either luciferase siRNA or scramble siRNA. Results from luciferase assays showed that transfection with luciferase siRNA significantly repressed luciferase activity of the luciferase reporter by about 60% when compared to the control siRNA (FIG. 14). In contrast, there was very limited luciferase activity repression when FusionHD or LIPOFECTAMINE® 2000 was used for transfection (FIG. 14).

Based on the data described herein using grapefruit-derived liposomes, it was believed that the liposomes have a number of advantages over other transfection agents, including: a much higher transfection efficiency of immune cell; a more simple, rapid and inexpensive protocols for making grapefruit liposomes to package nucleic acids; the ability, unlike other transfection agents, to increase the transfection efficiency by adding grapefruit liposome to the cells repeatedly without causing cytotoxicity; and the presence of sera not affecting the transfection efficiency when using grapefruit-derived liposomes in vivo. Thus, the foregoing study further demonstrated that grapefruit liposomes are effective for a broad range of cell lines and cell types, resulting in high levels of transgene expression and low cytotoxicity that can then be used for therapeutic applications for in vivo gene delivery.

Materials and Methods for Examples 11-16

Isolation and Purification of Grapefruit Nanoparticles.

Grapefruits with the skin removed manually were pressed and the collected juice was diluted in PBS, differentially centrifuged and the nanoparticles then purified on a sucrose gradient. The purified nanoparticles were prepared for EM using a conventional procedure and observed using an FEI Tecnai F20 electron microscope operated at 80 kV at a magnification of 15,000× and defocus of 100 and 500 nm. Photomicrographs were taken using an AMT camera system.

Extraction of Lipids from Grapefruit-Derived Nanoparticles and Reassembling Nano-Sized Particles.

Total lipids were extracted from sucrose band (FIG. 15A) of processed grapefruit nanoparticles. Briefly, 3.75 ml 2:1 (v/v) MeOH:CHCl$_3$ was added to 1 ml of grapefruit nanoparticles in PBS, and vortexed. CHCl$_3$ (1.25 ml) and ddH$_2$O (1.25 ml) were added sequentially and vortexed. The mixture was centrifuged at 2,000 rpm for 10 min at 22° C. in glass tubes to separate the mixture into two-phases (aqueous phase and organic phase). For collection of the organic phase, a glass pipette was inserted through the aqueous phase with gentle positive-pressure and the bottom phase (organic phase) was aspirated and dispensed into fresh glass tubes. The organic phase samples were aliquoted and dried by heat under nitrogen (2 psi). Total lipids were determined using the phosphate assay as described previously.

Mice.

C57BL/6j mice and BALB/c mice, 6-8 weeks of age were obtained from Jackson Laboratories. All animal procedures were approved by the University of Louisville Institutional Animal Care and Use Committee.

Cell Culture.

The mouse 4T1 breast cancer, CT26 colon cancer, and human A549 lung epithelial cancer cell lines were purchased from ATCC. The mouse (H-2$^b$) glioblastoma cell line GL26 stably expressing the luciferase gene (GL26-Luc) was provided by Dr. Behnam Badie (Beckman Research Institute of the City of Hope, Los Angeles, CA), and maintained in RPMI 1640 media supplemented with 10% heat-inactivated FBS in a humidified CO$_2$ incubator at 37° C. Transient transfections of siRNA or plasmid DNAs were performed using LIPOFECTAMINE® 2000 (Invitrogen) according to protocols provided by the manufacturer.

Reagents and Antibodies.

Curcumin, JSI-124 (cucurbitacin I), beta-glucan, chloropromazine, indomethacin, nocodazole, cytochalasin D, bafilomycin A1, paclitaxel, and folic acid were purchased from Sigma-Aldrich (St Louis, MO) and dissolved in DMSO as stock solutions. Antibodies against total and phospho-Stat3 were purchased from Cell Signaling Technology Inc. (Danvers, MA). Antibody against mouse β-actin was purchased from Santa Cruz biotechnology (Santa Cruz, CA). The following fluorescent conjugated Abs were obtained from e-Bioscience: anti-CD4, anti-CD8 and anti-CD19. For FACS analysis of cell apoptosis, an Annexin-V fluorescein isothiocyanate/PI double-staining assay was performed according to the manufacturer's protocol (BioVision, Mountain View, CA). siRNA targeting the luciferase gene was purchased from Life Technologies (NY, USA) and the Label IT Biotin-DNA kit for biotinylation of pEYFP-C1 (Clontech) was purchased from Minis Bio LLC (Pittsburgh, PA). Cell viability was assessed via measurement of cellular ATP levels using the ATPLite luminescence-based assay (Perkin Elmer, Waltham, MA). EPNVs were labeled with near-infrared lipophilic carbocyanine dye (1,1'-dioctadecyl-3,3, 3'3'-tetramethyl-indotricarbocyanine-iodide, DIR, Invitrogen, Carlsbad, CA) or PKH26-GL (Sigma-Aldrich, St. Louis, MO) using a method described previously.

Lipidomic Analysis.

The lipid composition of EPNVs was determined using a triple quadrupole mass spectrometer (Applied Biosystems Q-TRAP, Applied Biosystems, Foster City, CA). The data were reported as % of total signal for the molecular species determined after normalization of the signals to internal standards of the same lipid class.

Confocal Image Analysis of Localization of EPNVs.

Tumor cells (4T1, GL26, A549, CT26 or SW620) were plated on 4-chamber slides (Tissue-Tek, Sakura, USA) Lab-Tek II) and cultured at 37° C. for 24 h. Then, the cells were cultured with fresh culture media in the presence of PKH26-labeled EPNVs (10 nmol). At variable time points after co-culture with PKH26-labeled EPNVs, the cells were fixed with 2% paraformaldehyde in PBS for 20 min at 22° C. The fixed cells were permeabilized with 0.2% Triton X-100 for 15 min, stained with 4',6-diamidino-2-phenylindole (DAPI) for 90 s. PKH26-loaded EPNVs in the cells were examined using a Nikon A1R-A1 confocal microscope equipped with a digital image analysis system (Pixera, San Diego, CA). For analysis of localization of EPNVs in primary lymphocytes, freshly purified splenic T or B cells (5×10$^6$) were co-cultured with PKH26-labeled EPNVs in a 24-well tissue culture plate for 6 h at 37° C. After washing with PBS 3×, the cells were fixed, permeabilized and stained with DAPI using the identical protocol as described above. Washed cells were centrifuged onto slides and PKH26-labeled EPNVs in the cells were examined using a Nikon A1R-A1 confocal microscope equipped with a digital image analysis system (Pixera, San Diego, CA). To determine the effects of temperature on EPNVs uptake, A549 cells were cultured in 4-chamber slides at 37° C., 20° C. or 4° C. for 6 hours with PKH26 loaded EPNVs. After washing 3×, EPNV positive cells were observed using confocal microscopy.

Flow Cytometry Assay for Uptake Quantification of Grapefruit Derived EPNVs.

For uptake experiments, tumor cells were grown in 12-well plates with Eagle's minimal essential medium (EMEM) in the presence of 10% fetal bovine serum (FBS) for 24 h. PKH26-labeled EPNVs (10 nmol/ml) freshly prepared under sterile condition were added to the culture media and incubated with cells for an additional 6 h. After washing with cold PBS 5×, cells were trypsinized with 0.25% Trypsin-EDTA (Invitrogen, Carlsbad, CA) and washed an additional two time. Finally, the cells were resuspended in flow cytometry buffer and analyzed by flow cytometry (BD Accuri™ C6 Cytometer, New Jersey USA) and FlowJo Version 7.6 software (TreeStar Inc). The data presented were based on the mean fluorescence signal for 50,000 cells collected. All assays were performed in triplicate.

To study EPNV taken up by primary lymphocytes, subsets of T and B cells were purified from the spleens of C57BL/6j mice with CD3 and CD19 beads, respectively (Miltenyl Biotec) according to the manufacturer's protocol. In brief, spleens were removed aseptically and splenocytes were obtained by gently pressing the spleens between two sterile glass slides and then washing the lymphocytes from the slides using 10 ml of RPMI 1640 medium containing 10% fetal calf serum (FCS). This was pipetted several times and filtered through a 70-μm cell strainer (Falcon). The filtrate was then centrifuged at 1200 rpm for 5 min with 10% FCS-RPMI used for isolation of CD3+ T cells and CD19+ B cells according to the protocol provided (Miltenyl Biotec). Purified CD3+ T cells or CD19+ B cells were then resuspended and washed in RPMI 1640, cells were cultured in RPMI 1640 (Invitrogen) supplemented with 10% FCS, 2 mM L-glutamine, 100 U/ml penicillin, 100 μg/ml streptomycin, 25 mM Hepes, 50 μM 2-mercaptoethanol, 20 μg gentamicin and 1 mM sodium pyruvate in the presence of PKH26-labeled EPNVs for 6 h at 37° C./5% $CO_2$ incubator. The co-cultured cells were then washed with PBS three times. The percentages of PKH26+ cells were quantified by FACS analysis.

To investigate the effect of pH values on uptake efficiency, A549 cells ($5 \times 10^5$) were seeded in 6-well plates and cultured for 24 h. The culture medium was replaced with fresh medium with different pH values (5.5, 6.5, 7.4 and 9.0) and culturing continued with PKH26-labeled EPNVs (10 nmol/ml) for 6 h. The cultured cells were then washed with PBS 3×. The percentages of PKH26+ cells were quantified by FACS analysis.

To study the effect of endocytosis inhibitors on EPNV uptake, cells were cultured at 37° C. in the presence of an endocytosis inhibitor for 1 h prior to the addition of PKH26-labeled EPNVs, for an additional 6 h culture period. The cultured cells were then washed with PBS 3×. The percentages of PKH26+ cells were quantified by FACS analysis (BD Accuri™ Flow Cytometer) and FlowJo Version 7.6 software (TreeStar Inc.).

To analyze the effects of temperature on EPNVs uptake, A549 cells were cultured in 6-well tissue culture plates with PKH26 loaded EPNVs at 37° C., 20° C. or 4° C. for 6 hours. After washing 3×, PKH26+ cells was analyzed using FACS.

To determine whether the uptake of EPNV by A549 cells was energy dependent, confluent A549 cells were exposed to PKH26 labeled EPNVs (10 nmol/ml) for 3 and 6 hours at 37° C. in the presence or absence of a metabolic inhibitor—50 mM sodium azide. After washing 3× with PBS (pH7.4), PKH26+ cells were determined by FACS analysis as previously described. Cells exposed to the vehicle (PBS; pH 7.4), served as a control for intrinsic fluorescence, both in the presence and the absence of 50 mM sodium azide. The data were analyzed by FACS (BD Accuri™ Flow Cytometer) and FlowJo Version 7.6 software (TreeStar Inc).

To identify the cells that EPNVs targeted in vivo, mice were intravenously injected with PKH26 labeled EPNV (200 nmol/mouse). 72 h after injection, total spleen and liver cells resuspended in FACS analysis buffer were stained with anti-CD4, CD8, CD19, DX5, and F4/80 antibodies for further quantitatively analysis of PKH26+ cells.

Fluorescent Imaging In Vitro and Vivo.

In vitro imaging assays for A549 cells were conducted with EPNVs. A total of $1 \times 10^5$ cells were added to each well of 12-well plates. DIR dye-loaded EPNVs were diluted in PBS and added to 3 wells per concentration. After incubation at 37° C. in 5% $CO_2$ at variable times, cells were washed with ice cold PBS 5×. Light emission from the wells of the plates was measured with a Kodak Image Station (4000 MM Pro system, Carestream, Woodbridge, CT) and quantified using the vendor software. Regions of interest (ROI) were drawn manually around the area of each individual well of plate, and the intensity of light emitted from each ROI was measured. Data were normalized to light emission of an equal number of untreated cells otherwise incubated under the same conditions as the treated cells.

To evaluate the stability of circulating EPNVs in mice, 200 nmol of DIR dye-encapsulated EPNVs were injected via tail vein. At various time points (1 h, 2 h, 6 h, 24 h, 48 h, 72 h, 96 h, 120 h, 144 h and 172 h), blood was withdrawn into an anti-coagulant tube. The DIR signals from equal volume blood samples were then measured with a Kodak Image Station (4000 MM Pro system, Carestream, Woodbridge, CT) and quantified using the vendor software.

To determine the biodistribution of EPNVs in mice administered by different routes, 100 nmol of EPNVs were administered (subcutaneously, intraperitoneally, intravenously, and intramuscularly, and by intranasal drop) using methods as described previously. 72 h after administration mice were sacrificed and each organ was collected and light emission from the samples was measured with a Kodak Image Station (4000 MM Pro system, Carestream, Woodbridge, CT) and quantified using the vendor software.

To evaluate the stability of injected EPNVs, mice were intravenously injected with 100 nmol of DIR dye labeled EPNVs and sacrificed at different time points (1 d, 3 d, 5 d, 7 d, 9 d, 12 d, 15 d, 20 d). Light emission from each organ of mice was then measured using an Odyssey light imager and quantified using the vendor software.

Assessment of Liver Damage and HE Stained Tissues.

ALT and aspartate aminotransferase (AST) in the sera of the mice were quantitatively analyzed using the Infinity Enzymatic Assay Kit (Thermo Scientific). For histopathology analysis, H&E staining was performed on paraffin-embedded liver, lung, spleen, and kidney sections using a method as described.

Western Blot.

Western blots were done by first lysing cells and then the proteins of the lysed cells were separated on 10% polyacrylamide gels using SDS-PAGE. Separated proteins were transferred to nitrocellulose membranes. The western blot was carried out with the anti-Stat3 and anti-phospho-Stat3 antibodies (Cell Signaling) or anti-β-actin antibody as a control (Santa Cruz Biotechnology, Santa Cruz, CA).

Cytokines Assay.

To determine the effect of EPNVs or EPNV encapsulated curcumin on the induction of cytokines, and splenocytes ($5 \times 10^6$), C57BL/6j mice were pre-stimulated with LPS (10 μg/ml) for 3 h, then EPNVs (200 nmol), free curcumin (50 μg) or EPNVs encapsulated curcumin (50 μg curcumin in 200 nmol EPNVs) was added and cultured for another 6 h. TNF-α and IL-6 in culture medium were measured using ELISA kits (eBioscience).

For analysis of immune stimulation of beta-glucan loaded EPNVs, splenocytes ($5 \times 10^6$) from C57BL/6j mice were cultured in 6-well plates in the presence of free beta-glucan (20 μg) or EPNV-beta-glucan (20 μg beta-glucan in 200 nmol EPNVs) for 6 h. then TNF-α and IFN-γ in supernatants were measured using ELISA kits (eBioscience).

Analysis of Storage Stability of EPNVs.

To determine the storage stability of agents carried by EPNVs, free PKH26-GL labeled and curcumin-loaded EPNVs were prepared in PBS (pH7.4) and stored at 4° C. The stability and bioactivity of curcumin was determined by the anti-inflammatory function of curcumin over a 2 month period.

In Vitro and In Vivo Cytotoxicity Analyses.

For evaluation of in vivo toxicity of injected EPNVs, mice were injected intravenously with 100 nmol of EPNVs once per day for 1 or 5 days. 24 h after the last injection, sera were collected for quantification of cytokines (TNF-α, IL-6, IL-10, IFN-γ and TGF-β) using a standard ELISA kit (e-BioScience) and liver ALT and AST were analyzed using AST/ALT Liquid Stable Reagent (Thermo Scientific).

For evaluation of in vitro toxicity of EPNVs, ATPLite assay was used for analysis of A549 cell viability and the Annexin V-FITC/Propidium iodide apoptosis assay was used for quantifying percentages of death of A549 cells treated with EPNVs. Briefly, $1 \times 10^5$ A549 cells were cultured in a 12-well plate at 37° C. under 5% $CO_2$ atmosphere for 24 h. EPNVs at the different concentrations (2, 4, 8, 20 and 40 µM) were added to the 24-h cultured media and the cells were cultured for additional 48 h. The percentage of viable cells was then determined using the ATPlite assay following the protocol provided by the manufacturer (Perkin Elmer). All experiments were conducted in triplicate.

The Annexin V-FITC/Propidium iodide apoptosis assay was used to quantify cell death in vitro. A549 cells were placed in a six-well culture plate and cultured in the presence of different concentrations (4, 8, 20, 40 and 80 µM) of EPNVs for 24 h. Cultured A549 cells were washed with ice cold PBS three times. Cells were harvested by trypsinization and stained using an Annexin V/FITC Apoptosis Detection kit (Roche, Cambridge, MA) according to the manufacturer's protocol. The stained cells were immediately analyzed by flow cytometry (FACScan; Becton Dickinson, Franklin Lake, NJ).

Imaging EPNVs Across the Placental Barrier.

To determine whether the EPNVs passed through the placental barrier of pregnant mice and diffused into the fetus, pregnant C57BL/6 mice were injected intravenously with DIR dye labeled EPNVs daily for 1 or 5 days (50 nmol of final phospholipid at each injection/mouse, n=5). 72 h after the last injection, the fetus and placenta were removed from anesthetized pregnant mice and imaged using the Odyssey image system or a Kodak Image Station.

Purification of Drug/Chemicals/DIR Dye or siRNA Encapsulated EPNVs.

A chemotherapy drug, JSI124, paclitaxel or agents including folic acid, zymosan A or luciferase gene siRNA were mixed with total lipids from grapefruit dissolved in chloroform and dried under nitrogen to obtain a thin and dried lipids-complex film. The film was reconstituted in PBS buffer, followed by sonication in water-bath sonicator for 30 min, allowing the lipids to self-assemble into drugs/chemicals/siRNA-loaded nanoparticles. Then drug/chemicals/siRNA loaded EPNVs were then purified via sucrose gradient. The purified band was collected and washed at 100,000×g for 2 h before use.

For preparation and purification of EPNVs loaded with biotin labeled anti-CD4, CD8 antibodies or eYFP vectors, biotin labeled anti-CD4, CD8 antibodies (2.5 µg, BD Pharmingen, USA) were incubated with EPNVs (200 nmol) at 4° C. overnight. The EPNVs-biotin-anti-CD4 or EPNVs-biotin-anti-CD8 complex was washed with PBS at 36,000 rpm for 2 h and the pellet resuspended in PBS for the transfection of T cells. To prepare eYFP vector loaded EPNVs, biotin labeled eYFP vectors (5 □g) were incubated with EPNVs (200 nmol) in OPTI-MEM at 37° C. for 2 h and subsequently used for transfection.

Brain Tumor-Bearing Mice Model.

GL26-luc brain tumor-bearing mice were prepared as reported previously. Tumor-bearing mice were treated intranasally for 10 consecutive days with EPNVs J51124 (12.5 pmol) or JSI124 loaded EPNVs. GL26 tumor growth was monitored by quantifying the activity of luciferase activity. Images were collected using a high-sensitivity CCD camera with wavelengths ranging from 300 to 600 nm with an exposure time for imaging of 2 minutes. Regions of interest were analyzed for luciferase signals using a Kodak Image Station and reported in units of mean intensity.

In Vivo Imaging of EPNV Mediated Targeting in Tumor Models.

Xenograft tumor growth models were used to demonstrate EPNV mediated targeted delivery of chemotherapy drug to tumors versus standard chemotherapy with paclitaxel. In the first set experiments, six-week-old female BALB/c-SCID mice (Jackson Lab) were injected subcutaneously with the human colon cancer SW620 cell line ($5.0 \times 10^6$ cells/mouse in 50 µl of PBS). In the second set of experiments, six-week-old female BALB/c mice (Jackson Lab) were injected subcutaneously with murine colon cancer CT26 cell line ($1.0 \times 10^6$ cells/mouse in 50 µl of PBS). In the third set of experiments, six-week-old female BALB/c mice (Jackson Lab) were injected at a mammary fat pad with the murine breast tumor 4T1cell line ($1.0 \times 10^6$ cells/mouse in 50 µl of PBS). When tumors reached approximately 60 $mm^3$ volume, the mice were randomly assigned to different treatment groups and injected intravenously with free EPNVs, paclitaxel (PTX, 20 mg/kg), EPNVs (200 nmol) loaded with folic acid (5 µg, EPNVs-FA), EPNVs (200 nmol) loaded paclitaxel (20 mg/kg, EPNVs-PTX) and EPNVs (200 nmol) loaded folic acid plus PTX (EPNVs-FA-PTX). Mice were treated every 3 days for 30 days with the last injection of being DiR dye labeled EPNVs. Growth of the tumors was measured. Biodistribution of EPNVs was monitored using a Kodak Image System after the final intravenous injection. Mice were sacrificed, tumors and other organs were removed and biodistribution of DiR labeled EPNVs was analyzed with a Kodak Image System.

In Vivo Imaging of EPNV Mediated Targeted Delivery of siRNA Model.

CT26-luc tumor bearing mice were prepared as described above and injected intravenously with free EPNVs, folic acid loaded EPNVs, EPNVs encapsulated with luciferase gene siRNA or both folic acid and luciferase gene siRNA every 3 days for a total of 5 injections. Before starting the imaging, mice were intraperitoneally administrated D-luciferine (150 mg/kg; Xenogen, Alameda, CA) dissolved in PBS and then anesthetized for determining the intensity of the mouse luciferase signals using a Kodak Image Station.

Figure 15A:
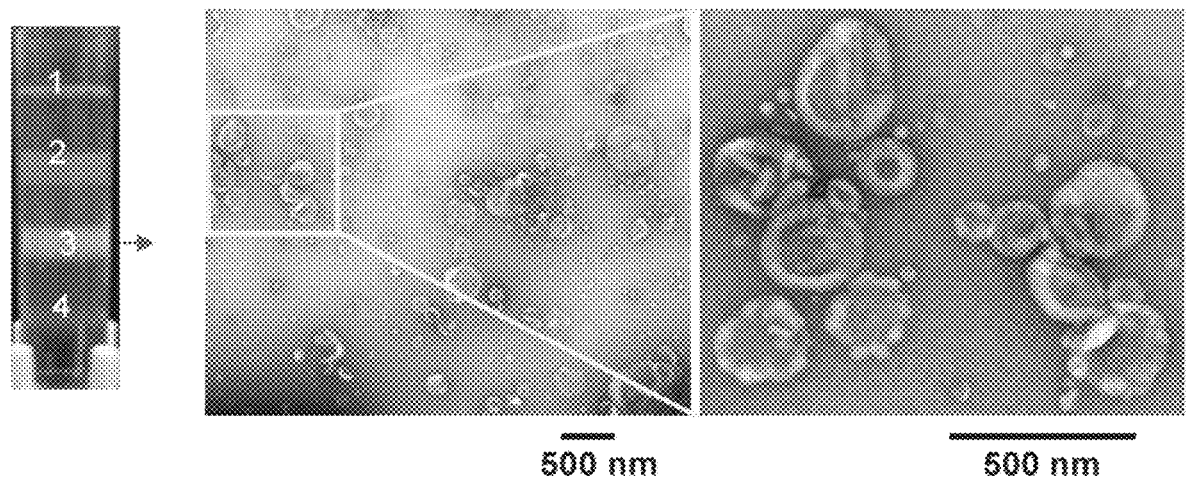
FIGS. 15A-15E include images and graphs showing the characterization of flower-like, nano-sized particles made from grapefruit-derived lipids, including: an image showing sucrose banded particles from grapefruit juice (FIG. 15A, left) and electromicroscopy visualization of nano-sized particles at low and high magnification (FIG. 15A, middle and right); images showing sucrose banded grapefruit lipid-derived edible plant nano-vectors (FIG. 15B, EPNVs, left) and electromicroscopy visualization of the nano-sized particles at low and high magnification (FIG. 15B, middle and right); a pie chart with a summary of the putative lipid species in the EPNVs (FIG. 15C); images showing electromicroscopy analysis of EPNVs before (left) and after (right) homogenization (FIG. 15D); and images showing electromicroscopy analysis of EPNVs embedded in polyBed 812, sectioned, and examined by electromicroscopy (FIG. 15E)

Example 11—Characterization of Nano-Sized Particles Assembled from Edible Plant-Derived Nanoparticles Lipids Using the foregoing techniques, edible plant nanoparticles were isolated from the juice of grapefruits. The particles were identifiable as nanoparticles based on electron microscopic examination (FIG. 15A, right) of a sucrose gradient purified band (FIG. 15A, left). Nanoparticles purified from grape and tomatoes were also identified by electron microscopy. Juices from edible plants were enriched in nanoparticles (0.8±0.07 g/pound of grape, 1.0±0.02 g/pound of grapefruit, and 0.2±0.01 g/pound of tomatoes), indicating that certain edible plants could serve as a resource for large scale production of fruit derived nanoparticles.

Figure 15B:
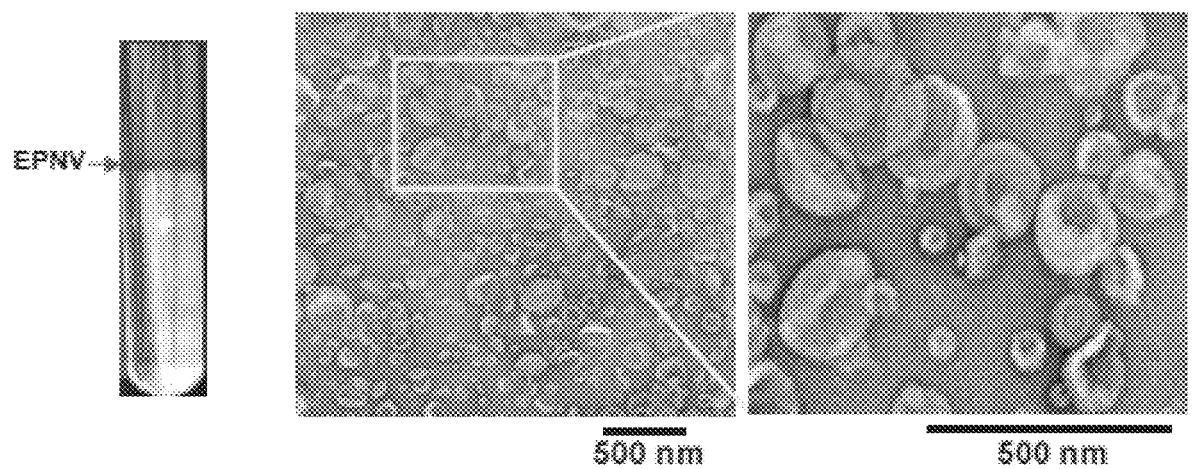
Figure 15C:
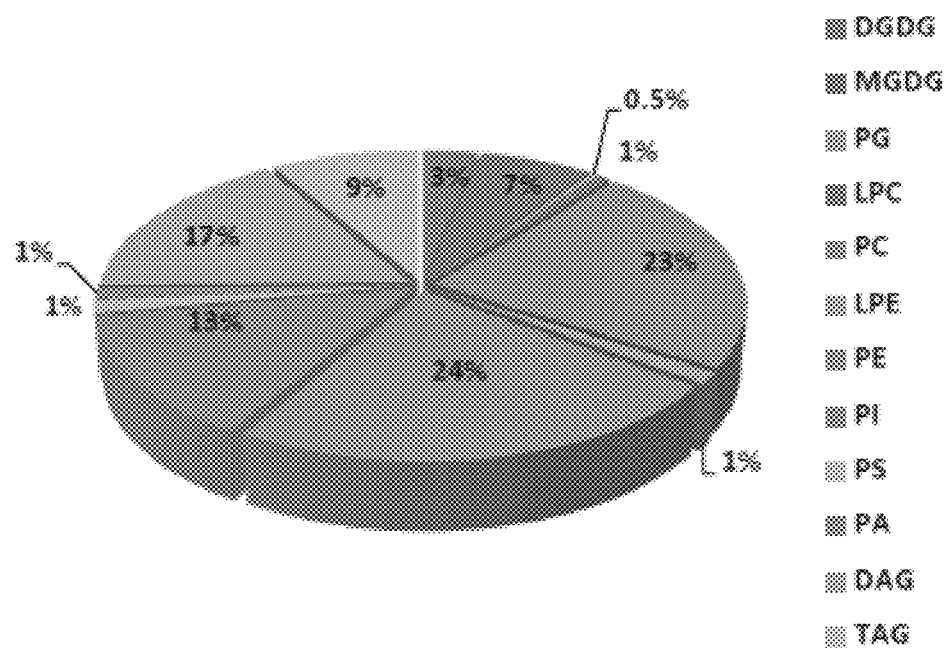
Figure 15D:
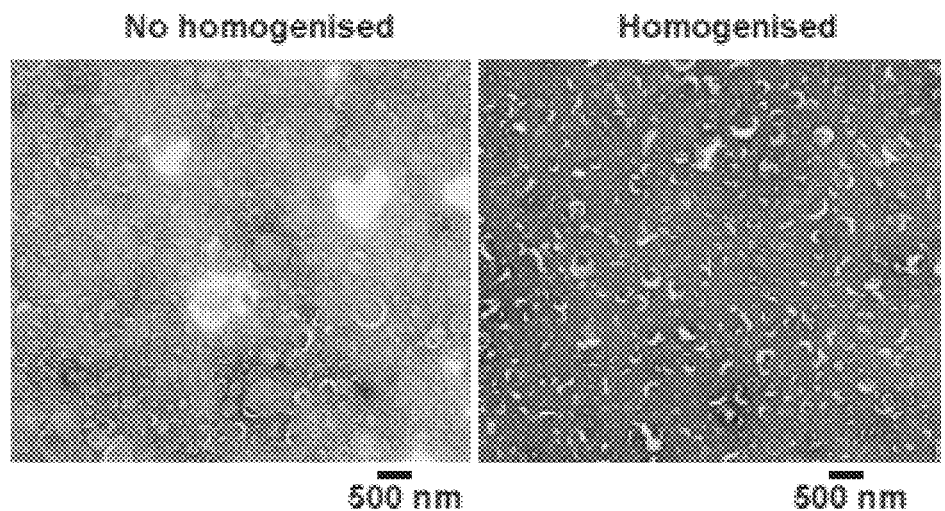
Figure 15E:
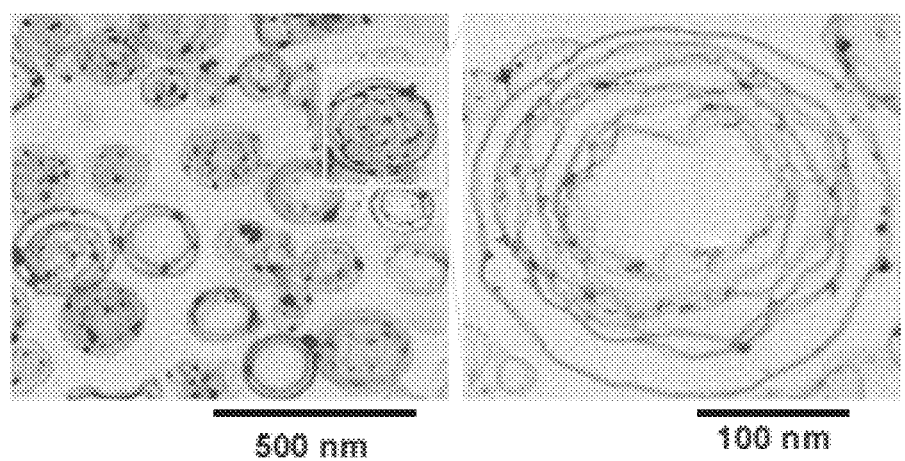
Figure 20:
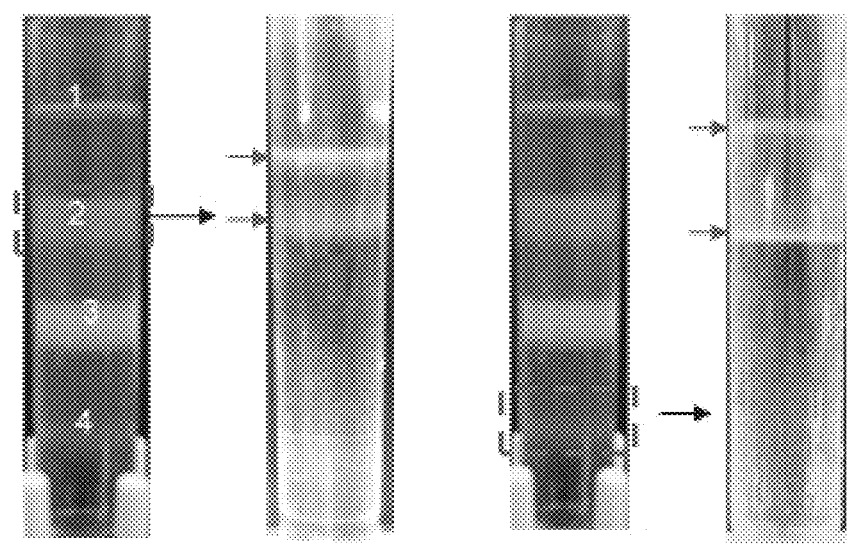
FIG. 20 includes images showing particles reassembled from lipids derived from two other bands of sucrose purified grapefruit particles.

To determine whether lipids from grapefruit nanoparticles could be reassembled into nano-sized particles for use as a delivery vector, grapefruit nanoparticle derived lipids were used and are referred to hereafter as an edible plant-derived nano vector or EPNV. Based on electron microscopic examination (FIG. 15B, right) of a sucrose gradient purified band (FIG. 15B, left) and the lipid profile (FIG. 15C, FIG. 20), the reassembled nano-sized particles were similar to the grapefruit nanoparticles. Nanoparticles assembled from the lipids of two other sucrose gradient bands (band 2 and 4, FIG. 15A, left) were also prepared, but a single uniform band could not be obtained (FIG. 20). Although the nanoparticles generated initially were heterogenous in size, passing the nano particles through a homogenizer resulted in more uniform sized nanoparticles (FIG. 15D). Electron microscopy results showed that most of the reassembled nanoparticles had a multi-layer flower-like structure (FIG. 15E). Collectively, these results indicated that lipids derived from grapefruit nanoparticles could be reassembled into nano-sized particles and in large quantities.

Example 12—Uptake and Toxicity of EPNVs

Figure 16A:
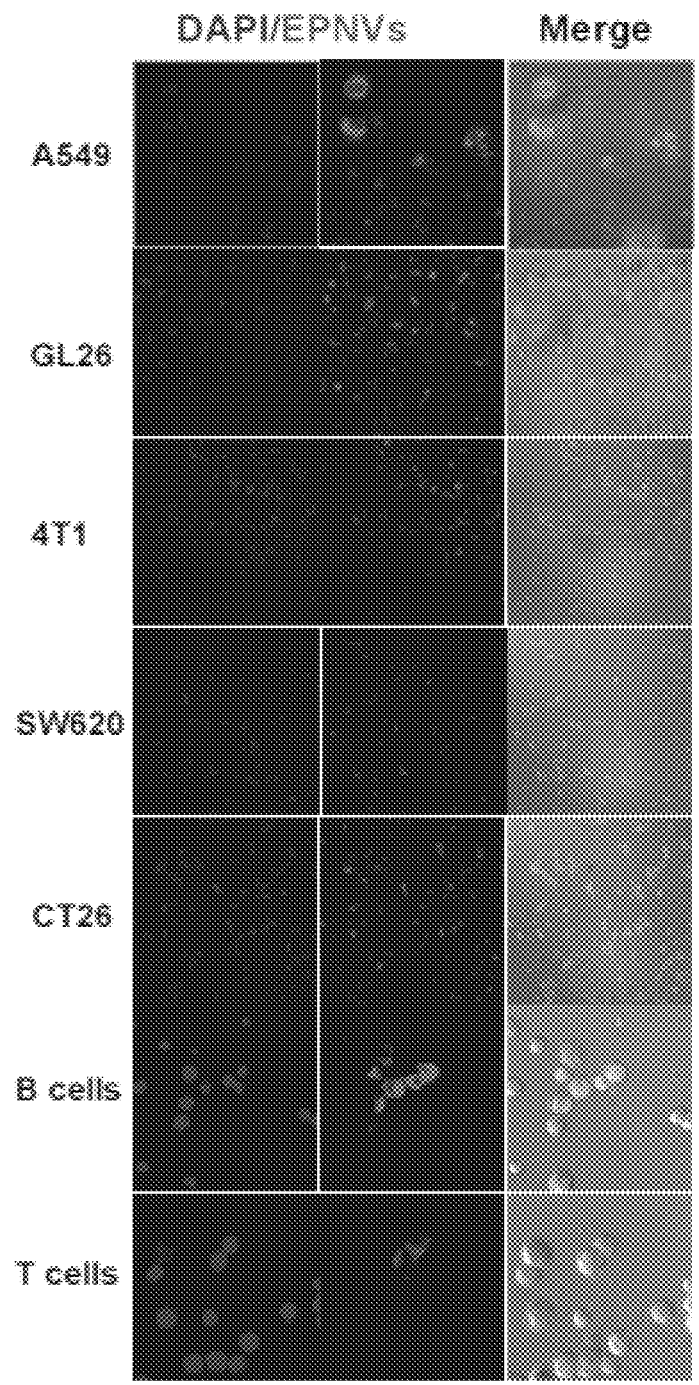
FIGS. 16A-16F include images and graphs showing the ability of both hematopoietic and non-hematopoietic cells to take up EPNVs; including: confocal images (FIG. 16A) of EPNVs taken up by various tumor cells (A549, GL26, 4T1, SW620 and CT26) and primary lymphocytes (T and B cells); graphs showing the FACS quantitative analysis of uptake efficiency of EPNVs (FIG. 16B); graphs showing the temperature (T, FIG. 16C), Time (FIG. 16D) and concentration dependence (FIG. 16E) of the efficiency of EPNVs uptake; and graphs showing the identification of potential pathways utilized by EPNVs to enter A549 cells (FIG. 16F)
Figure 16B:
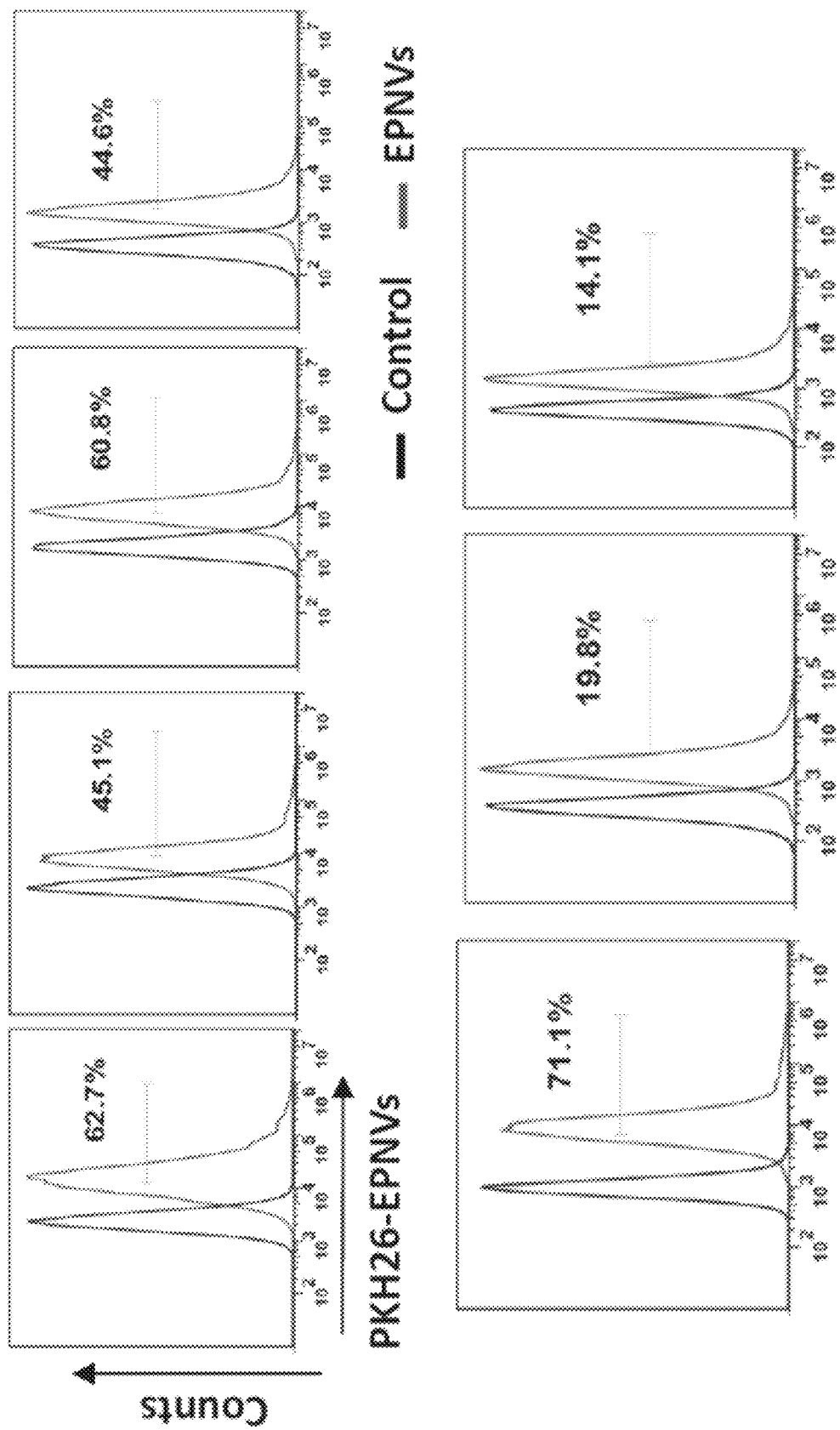
Figure 16C:
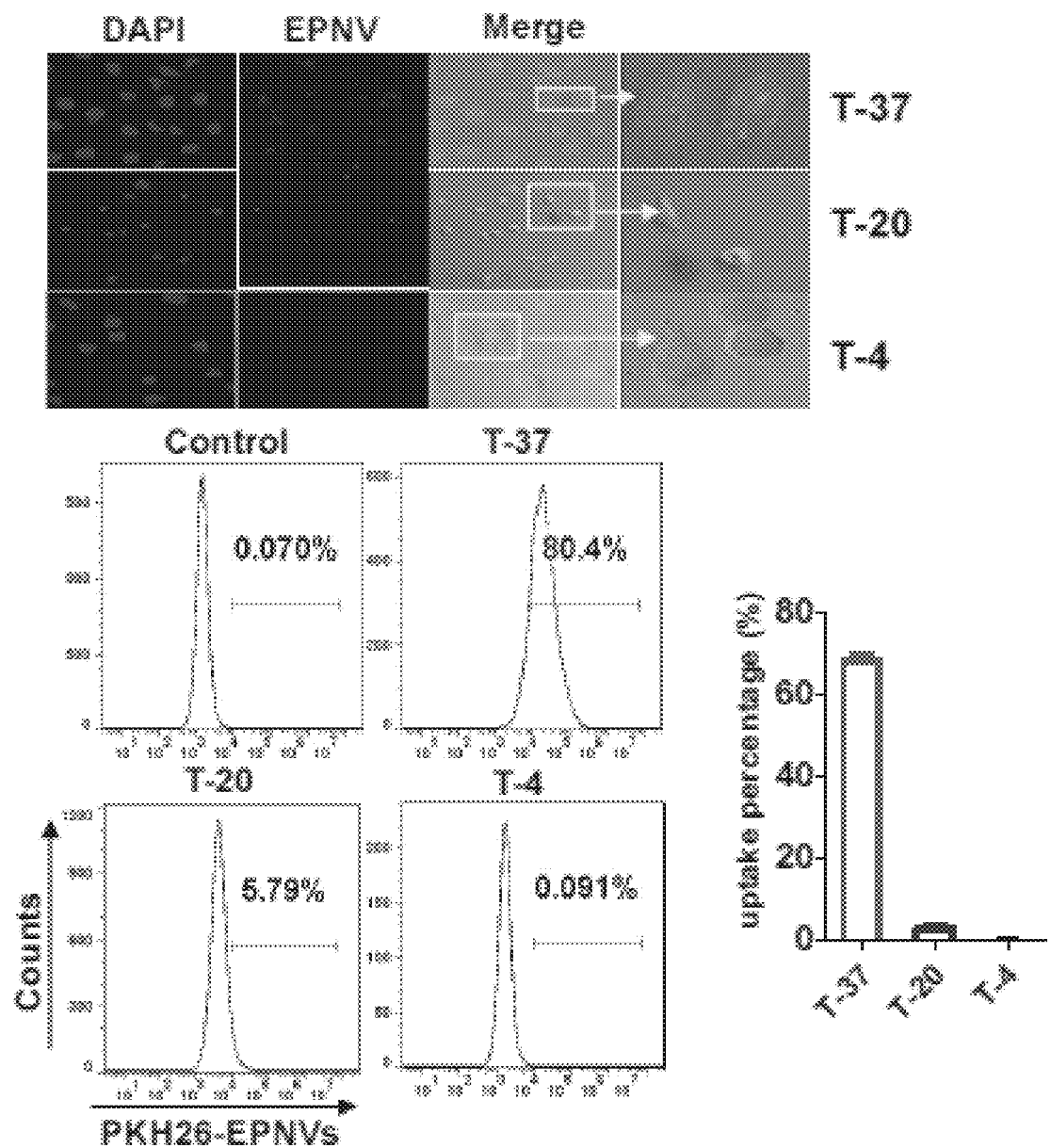
Figure 16D:
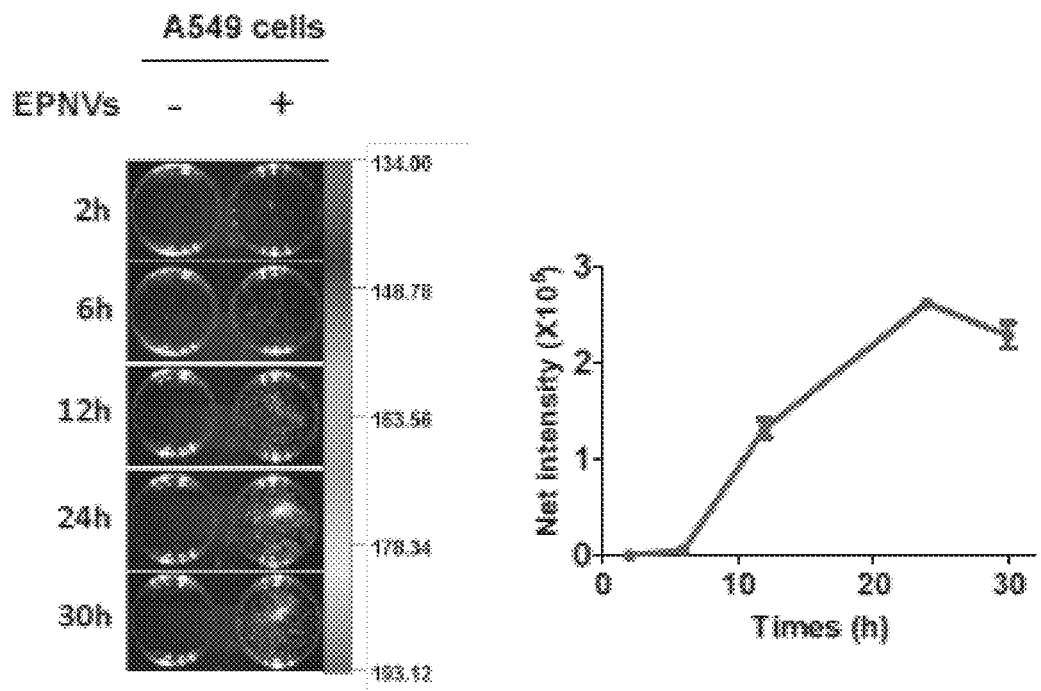
Figure 16E:
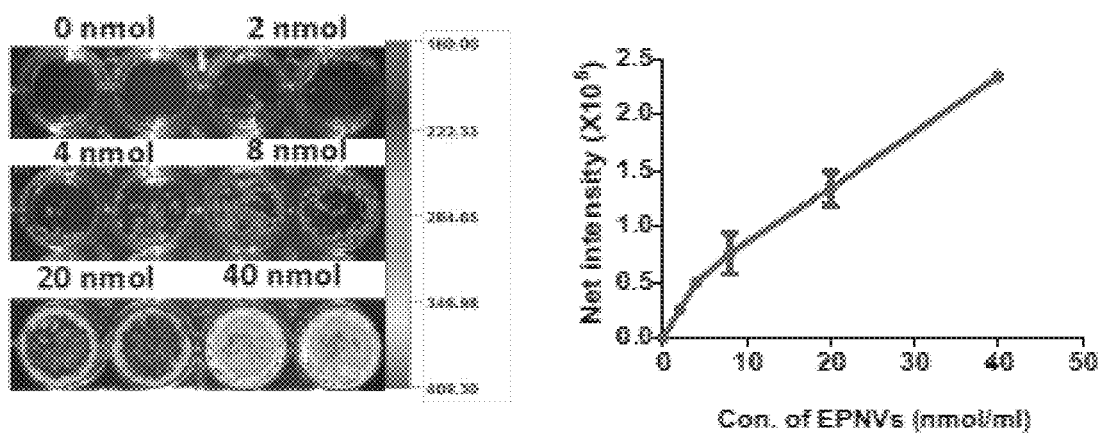
Figure 16F:
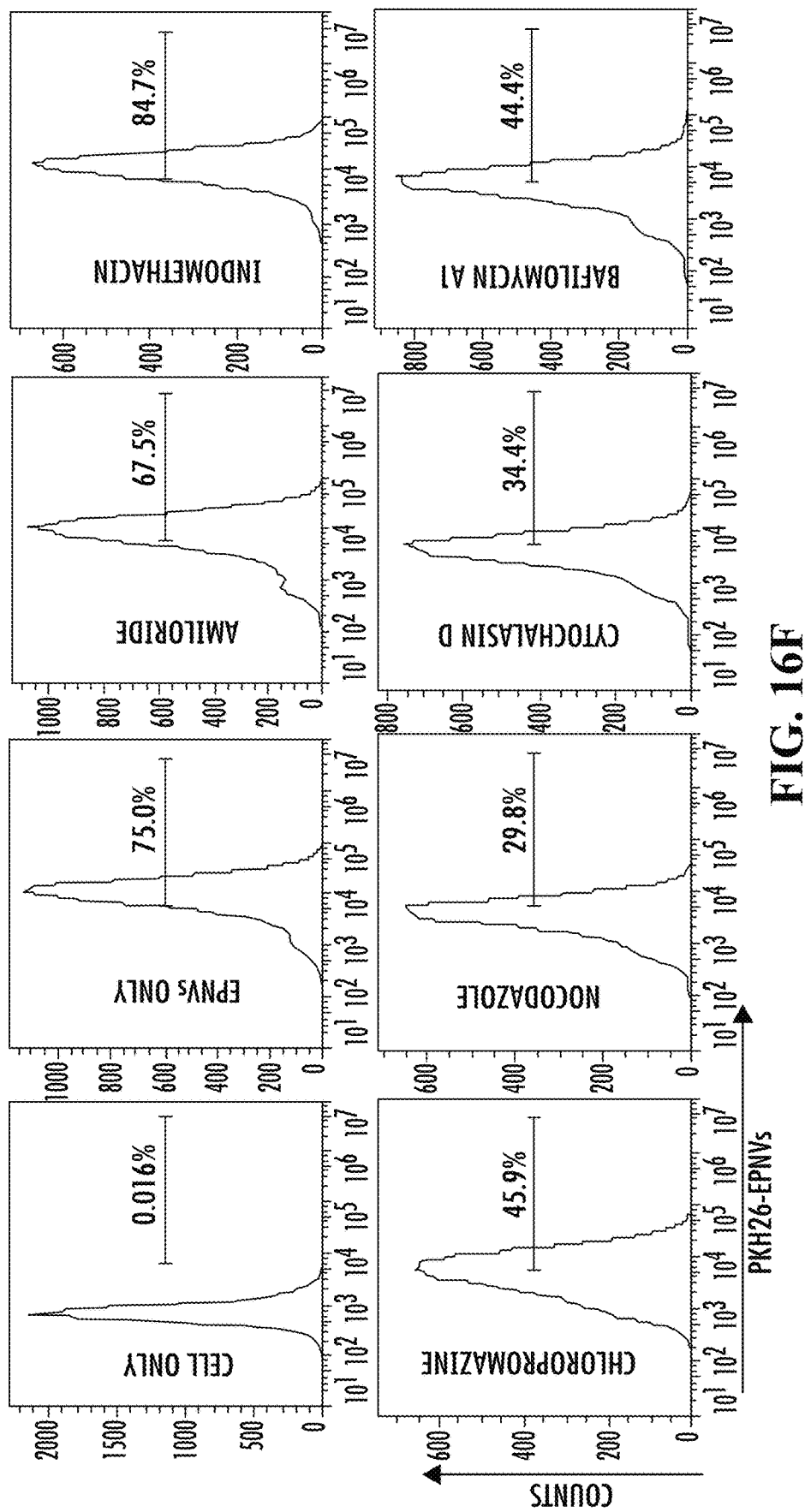
Figure 17A:
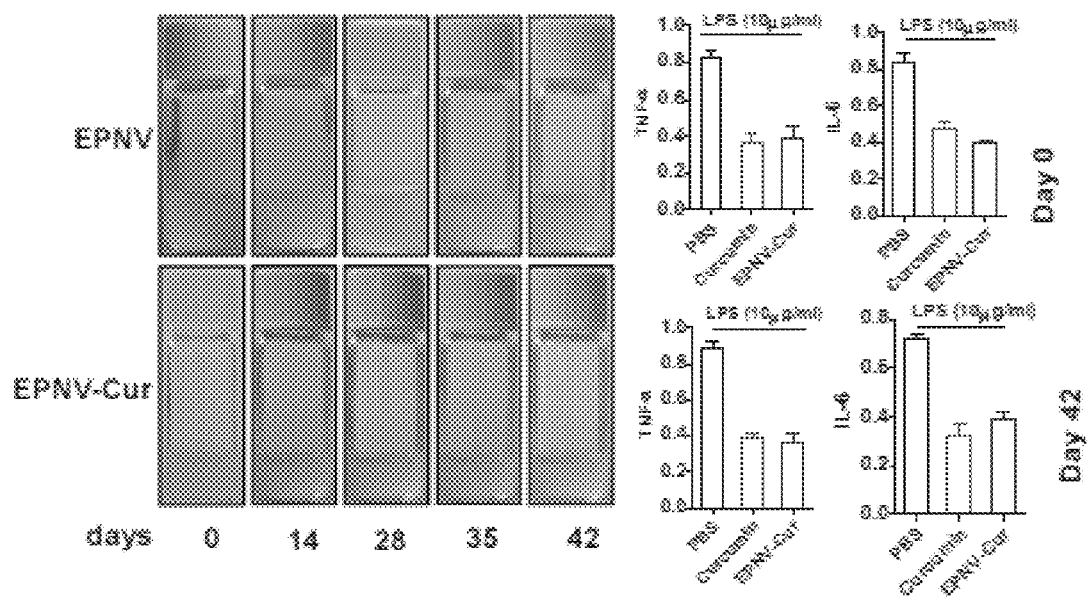
FIGS. 17A-17G are images and graphs showing the in vitro and in vivo stability and biodistribution of EPNVs, including: an image and graphs showing the stability of PKH26-labeled EPNVs and curcumin-loaded EPNVs in PBS as indicated by color changes of PKH26 labeled EPNVs (FIG. 17A, left) and anti-inflammatory effects of curcumin loaded EPNVs on inhibition of LPS induced inflammatory cytokines (FIG. 17A, right); images and a graph showing the biodistribution of DiR dye-labeled EPNVs in mice either administered subcutaneously (s.c.), intraperitoneally (i.p.), intravenously (i.v.), and intramuscularly (i.m.) (FIG. 17B); an image and a graph showing the tissue biodistribution over time of DiR dye-labeled EPNVs administrated i.v. to mice (FIG. 17C); graphs showing in vivo cell targeting as determined by FACS analysis of total splenocytes and liver cells of mice injected i.v. with PKH26 labeled EPNV (FIG. 17D); images and a graph showing in vivo stability of DiR dye-labeled EPNVs as determined by scanning various organs of mice injected i.v. with DiR dye labeled EPNVs (FIG. 17E); and images and a graph showing the in vivo stability of circulating EPNVs as determined by scanning peripheral blood of mice injected i.v. with DiR dye-labeled EPNVs (FIG. 17F); and images of pregnant mice injected i.v. with DiR dye-labeled EPNVs either 1 (lx, left) or 5 times (5×, right), where the DiR signals are indicated by an arrow in the fetus and placenta (circled dotted line) (FIG. 17G)
Figure 21:
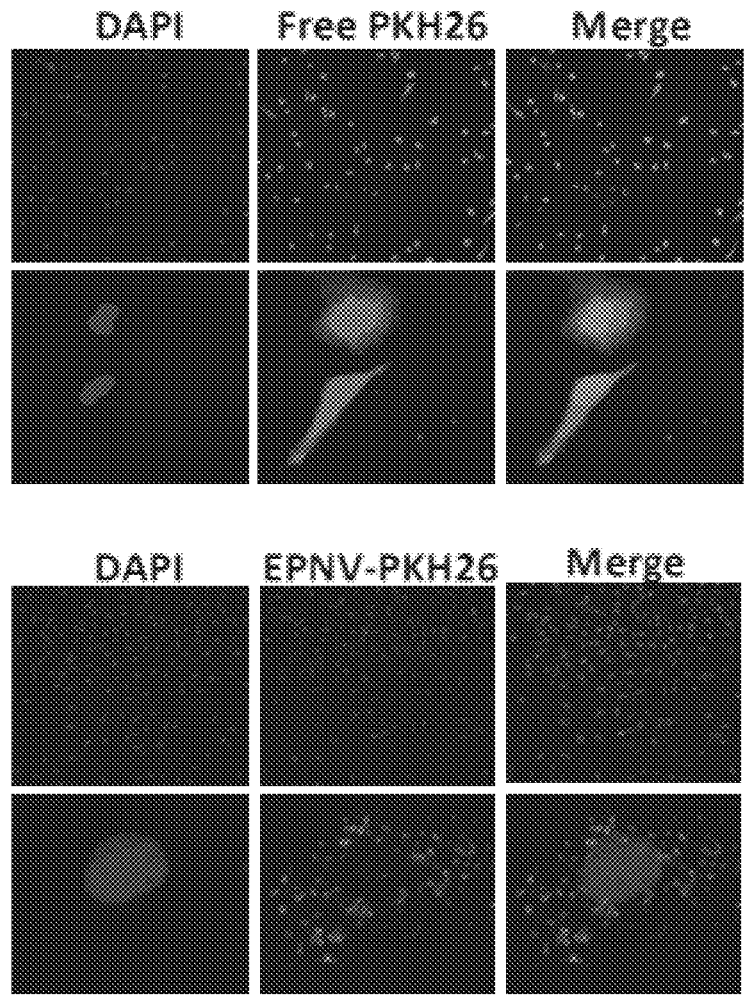
FIG. 21 includes images showing the characterization of signals for PKH26 labeled EPNVs or free PKH26 dye taken up by A549 cells, where the A549 cells were incubated with free PKH26 dye (top) or PKH26 labeled EPNVs (bottom), and the pattern of PKH26+ dots was imaged using confocal microscope.
Figure 22:
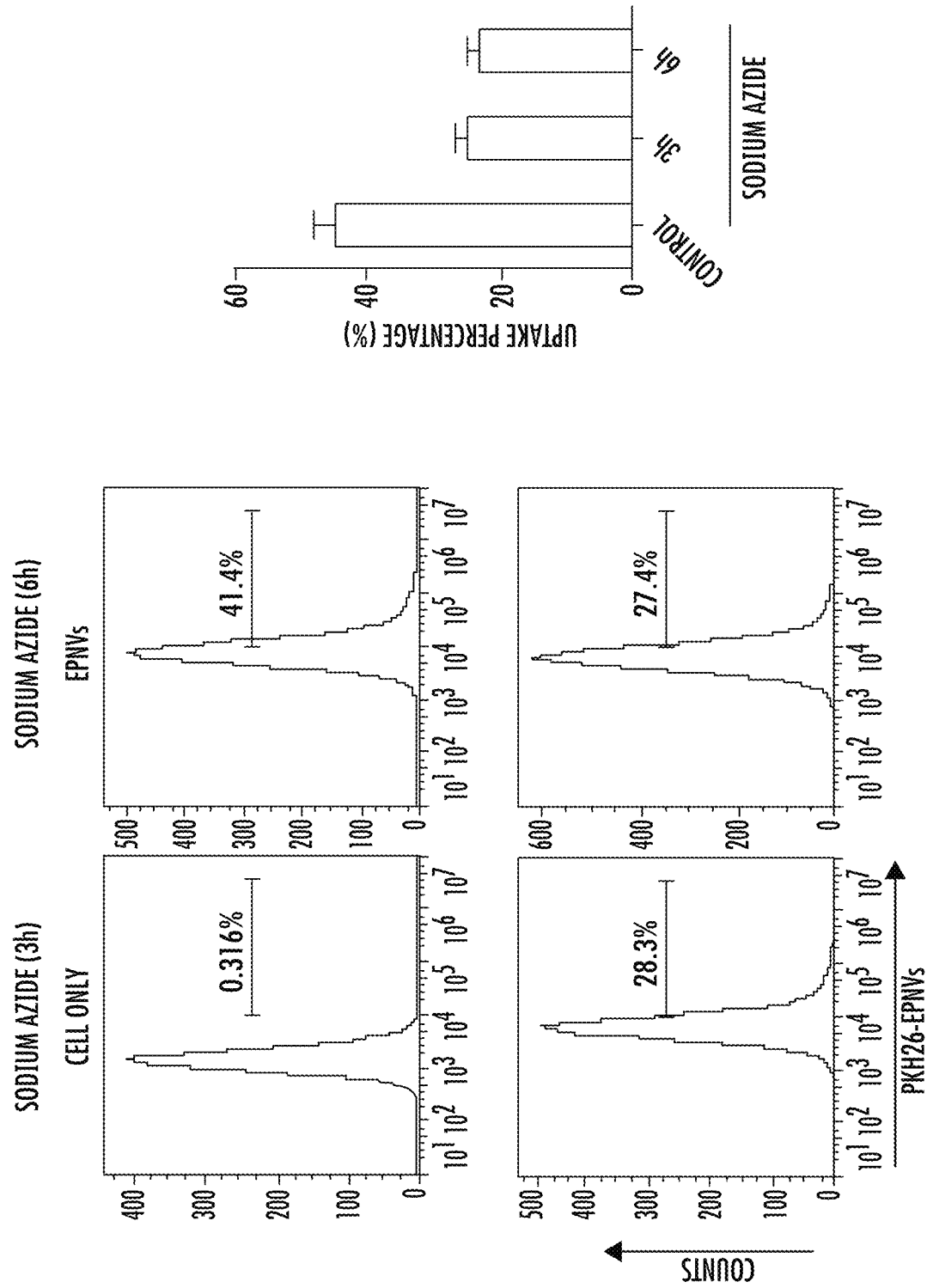
FIG. 22 includes graphs showing the effects of metabolic inhibitor-sodium azide and pH values on EPNVs uptake, where A549 cells were cultured with PKH26 labeled EPNVs for 3 or 6 hours in presence of 50 mM sodium azide, then the percentage of taking up was qualitatively analyzed using FACS.
Figure 23:
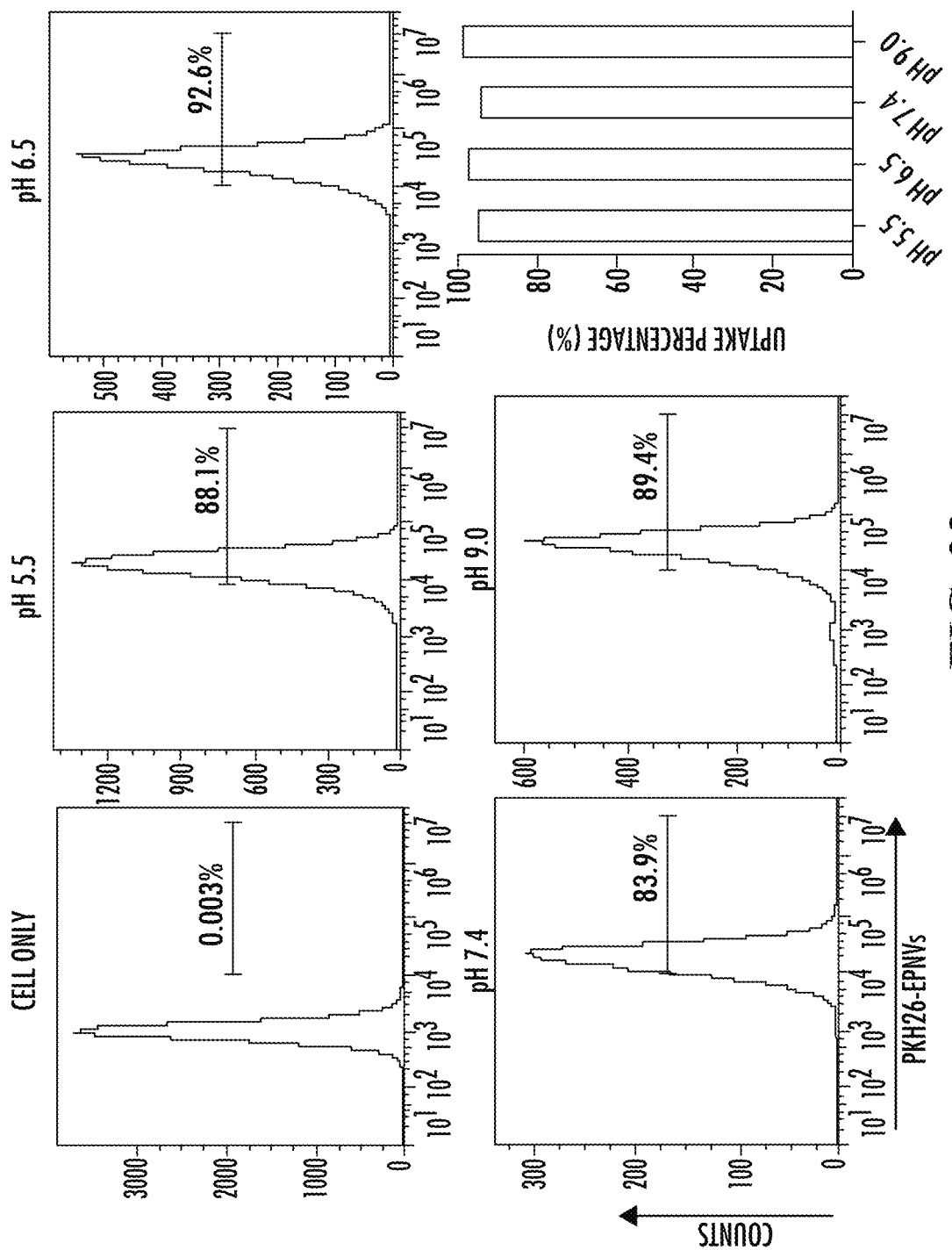
FIG. 23 includes further graphs showing the effects of pH values on EPNVs uptake, where A549 cells were cultured with PKH26 labeled EPNVs in DMEM media with different pH values (5.5, 6.5, 7.4 and 9.0) for 6 hours, and uptake efficiency was evaluated by FACS analysis.
Figure 24A:
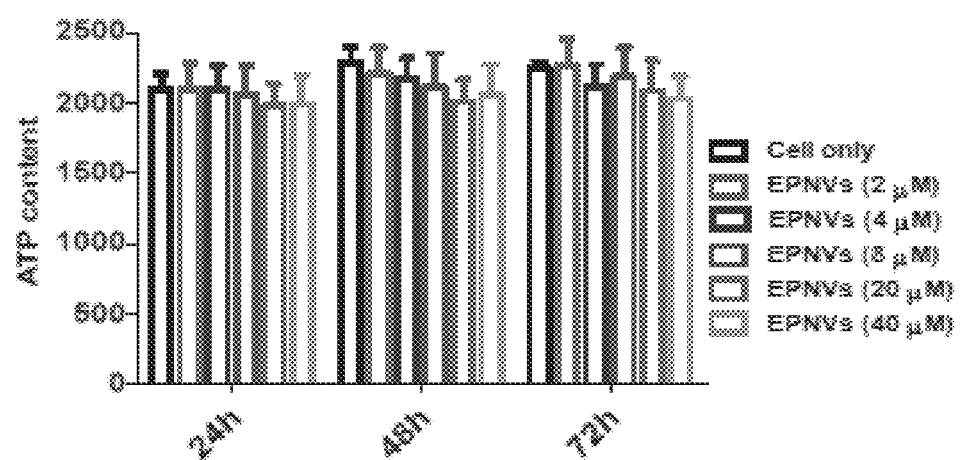
FIGS. 24A-24B includes graphs showing the effect of EPNVs on cell proliferation and apoptosis, including: a graph showing the analysis of the proliferation of EPNV-treated A549 cells using an ATPlite assay 24, 48 or 72 h after exposure to different doses of the EPNV (FIG. 24A); and graphs showing the extent of apoptosis in EPNV-treated A549 cells as analyzed by FACS analysis of Annexin V+/PI+ cells (FIG. 24B)
Figure 24B:
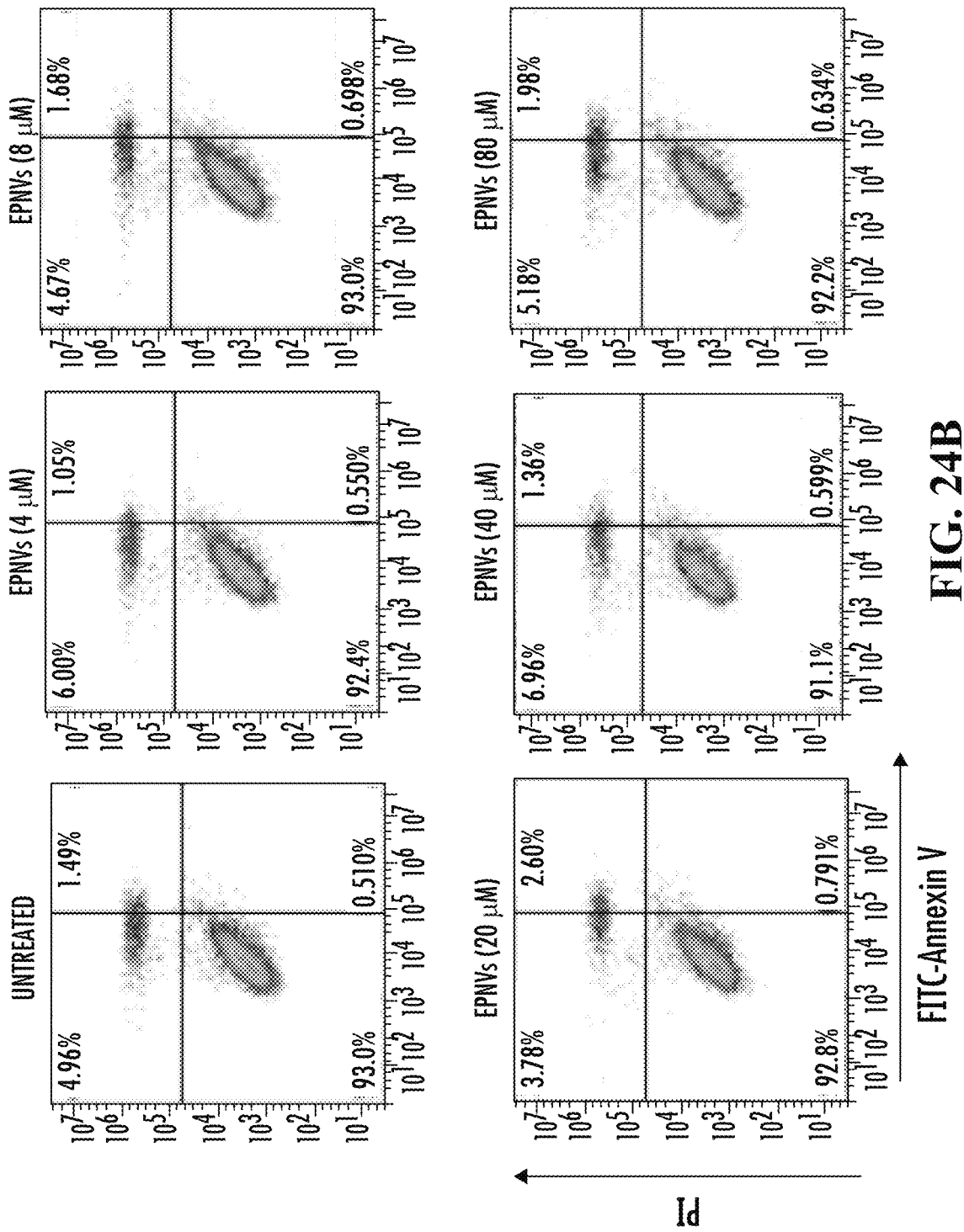

To evaluate the potential use of EPNVs as a vector to deliver therapeutic agents, the tropism and toxicity was evaluated. The efficient uptake of EPNVs by different cell types was first evaluated. The following cells were used: glioma cell line GL26 (murine brain macrophages), lung cancer cell line A549 (human lung epithelial cell), SW620 (human colon cancer cell line), CT26 (murine colon cancer cell line), 4T1 (murine breast cancer cell line), and primary mouse T cells and B cells (splenic lymphocytes) isolated from BALB/c mice. Each of the cell types was co-cultured with PKH26 labeled EPNVs (PKH26-EPNVs) and the presence of EPNVs in cells was examined using confocal microscopy (FIG. 16A) or by FACS (FIG. 16B), and determined by quantitative analysis of PKH26-EPNVs$^+$ cells. The results indicated that the majority of GL26, A549, SW620, CT26, and 4T1 cells took up the EPNVs. More than 20% of the B cells and 14% of the T cells took up the EPNVs within 12 hours after the co-culture, which was remarkable since B and T cells are considered the most difficult to transfect using any commercially-available transfection agents. When comparing the results with cells incubated with free PKH26 dye, distinct patterns of PKH26$^+$ staining were observed in cells incubated with PKH26 labeled EPNVs which was not the case in cells incubated with free dye (FIG. 21). This indicated that the PKH26$^+$ signals were derived from the EPNVs$^+$ cells, not with free PKH26 dye contamination. Using A549 as an example, it was further demonstrated that the efficiency of uptake of EPNVs was a temperature-dependent process. Uptake rates were very slow at 4° C. and increased as the temperature was raised (FIG. 16C). The results from imaging (FIG. 16C, top panel) or from FACS analysis (FIG. 16C, bottom panel) of A549 co-cultured with PKH26 labeled EPNVs indicated that more than 87% of A549 cells took up the EPNVs at 37° C., but not at 20° C. or at 4° C. Uptake of EPNVs at 37° C. in the presence of the metabolic inhibitor sodium azide (50 mM) was significantly reduced after 3 and 6 hour incubations (FIG. 22), suggesting that metabolic energy is required for this process. Under physiological temperature (37° C.) conditions, an initial rapid uptake of DiR dye labeled EPNVs (20 nmol) was observed within the first 2 h (the first time point) and followed by a linear uptake that reached a peak between 20 to 24 h (FIG. 16D). The uptake of DiR dye labeled EPNV by A549 cells was also found to be EPNV concentration dependent. Treatment with the highest concentration (40 nmol/ml) of EPNVs resulted in no reduction of EPNV uptake (FIG. 16E), indicating that epithelial A549 cells have a high capacity for taking up EPNV. To further examine the mechanism of EPNV internalization, A549 cells were treated with endocytosis inhibitors. Uptake of PKH26-EPNV (FIG. 16F) was markedly inhibited by the macrolide antibiotic bafilomycin A1, which prevents maturation of autophagic vacuoles. In addition, uptake of PKH26-EPNVs was greatly diminished by treatment of A549 cells with cytochalasin D, an inhibitor of microfilament formation required for phagocytosis, nocodazole, an inhibitor of the polymerization of microtubules, and the clathrin-mediated endocytosis inhibitor chlorpromazine. Amiloride, an inhibitor of macropinocytosis, and the caveolae-mediated endocytosis inhibitor indomethacin did not affect uptake of PKH26-EPNV. Increasing the pH from 6.5 to 9.0 had no apparent effect on the uptake of EPNV (FIG. 23). Whether EPNVs were toxic to A549 cells was next determined. The results of the ATPlite assay, which quantitatively measures cell proliferation, and the PI/Annexin V assay, which quantifies cell death, revealed that EPNV treatment at concentrations up to 40 nmol/ml has no effect on A549 cell proliferation (FIG. 24A) or death rates (FIG. 24B) when compared with PBS treated cells. Collectively, these findings indicated that under physiological temperature conditions, EPNVs were taken up by both cell lines tested, as well as primary lymphocytes. Moreover, EPNVs were stable at 4° C. for more than 1 month and did not lose their ability to carry curcumin and aid in maintaining the biological activity of curcumin as determined by its persistent anti-inflammatory activity (FIG. 17A). Based on these results, it was believed that EPNVs had the capacity to deliver therapeutic products in vitro.

Example 13—Tissue Tropism of EPNVs

Figure 17B:
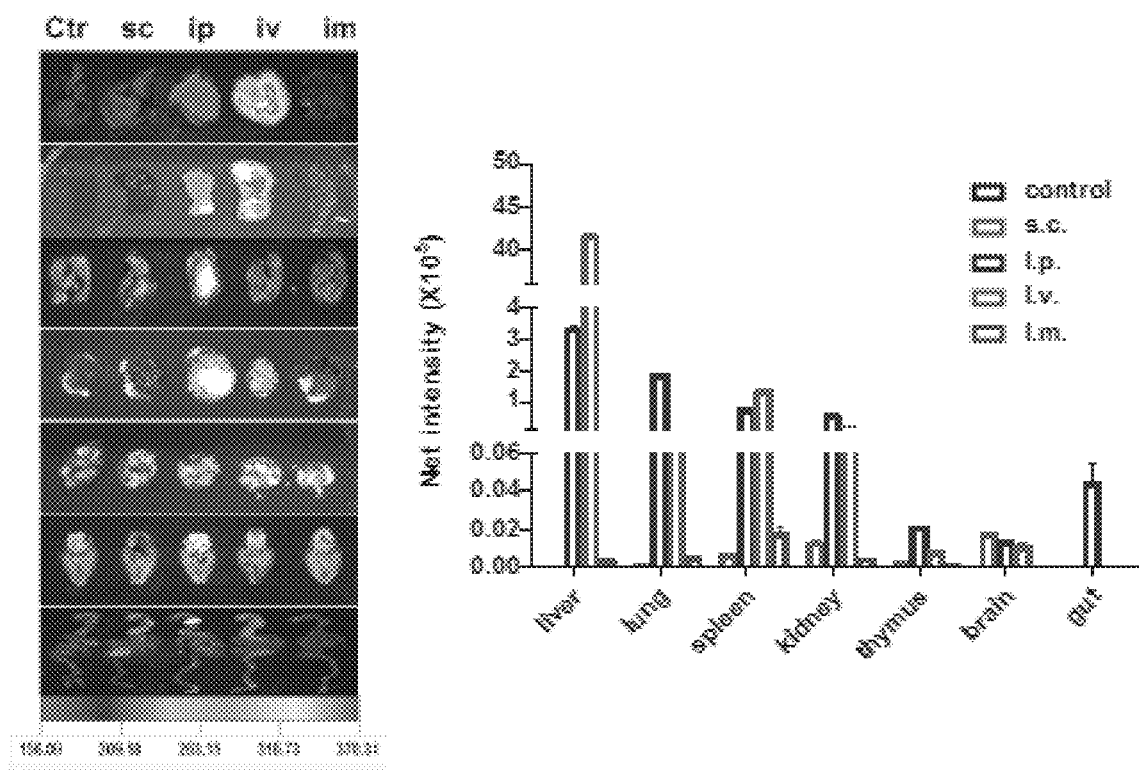
Figure 17C:
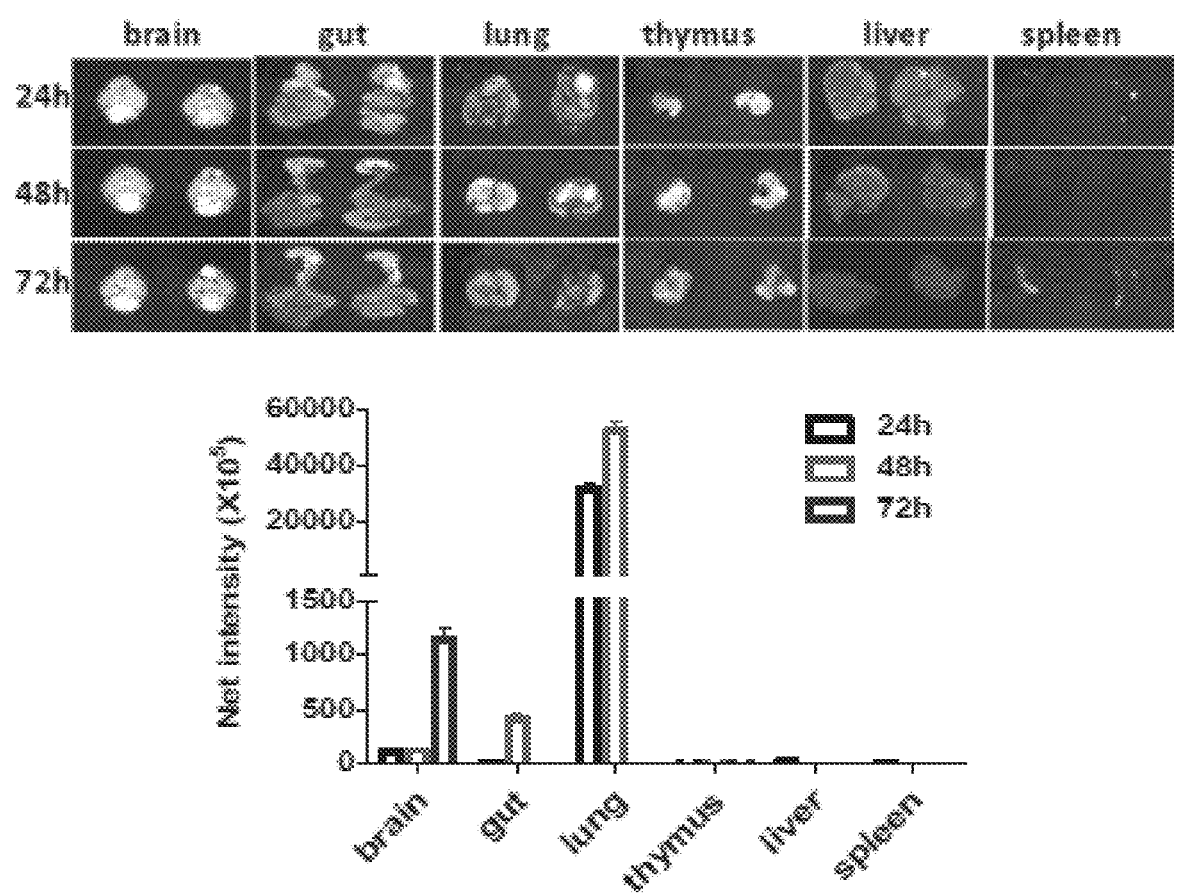
Figures 1, 17D:
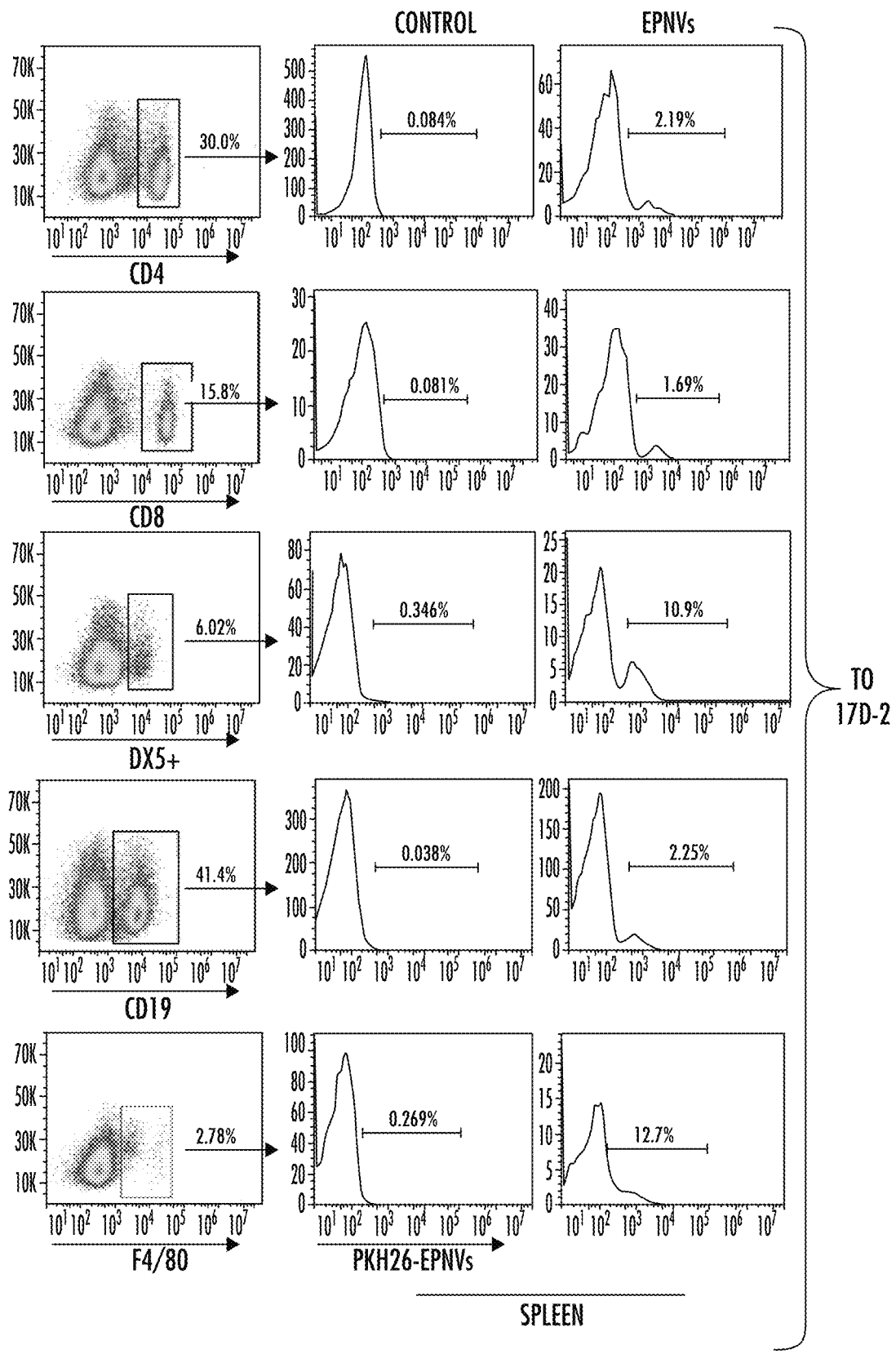
Figures 2, 17D:
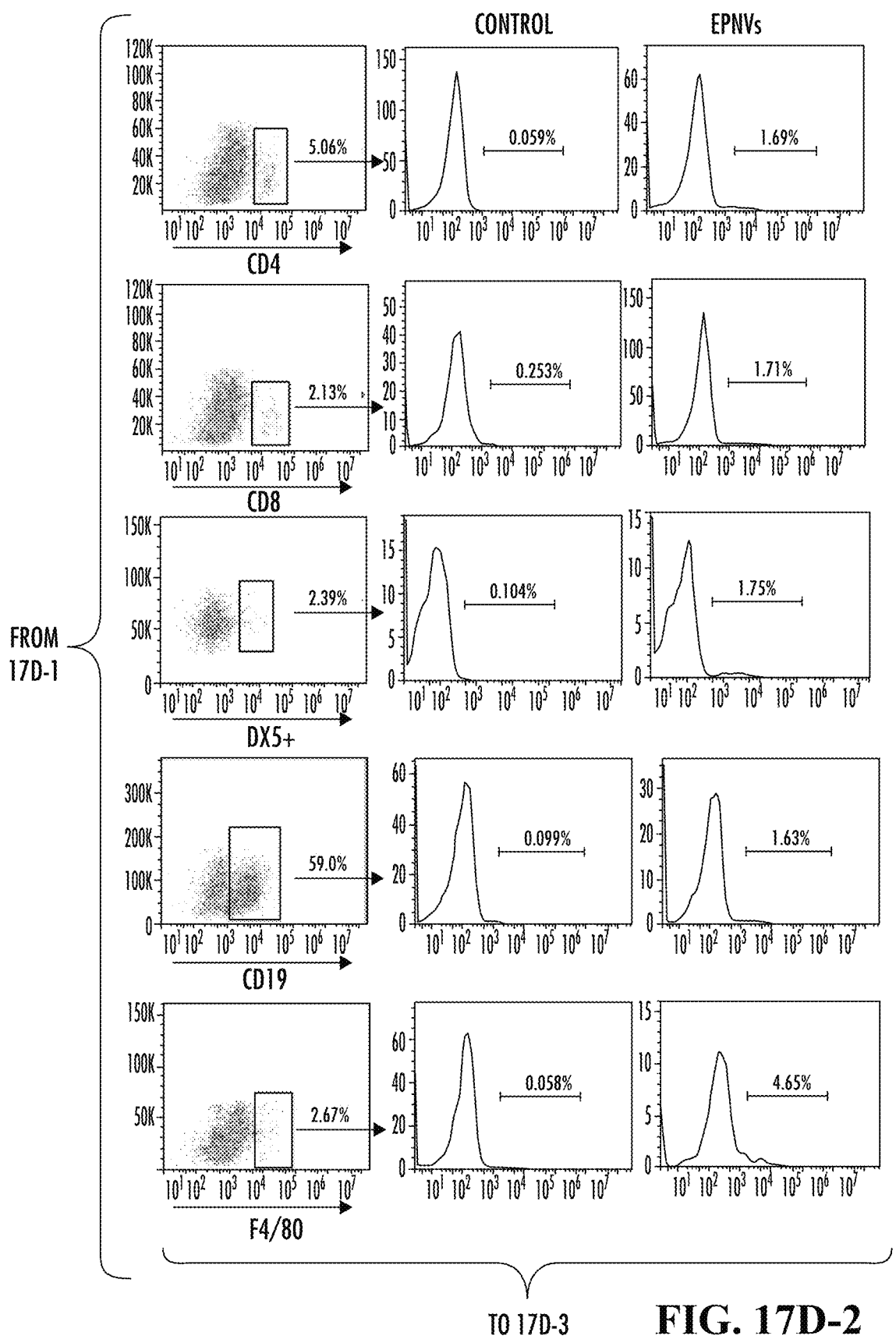
Figures 3, 17D:
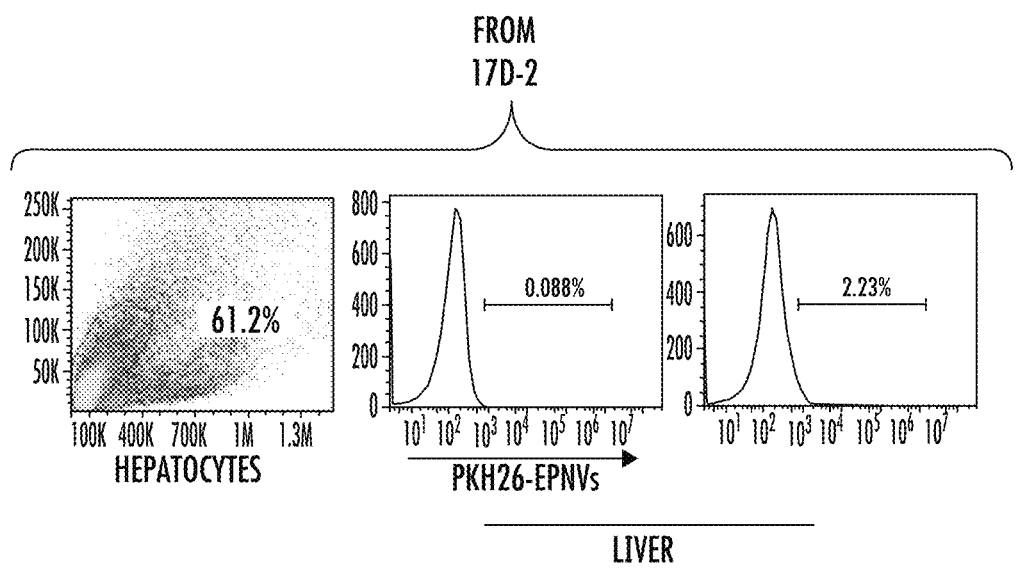
Figure 17E:
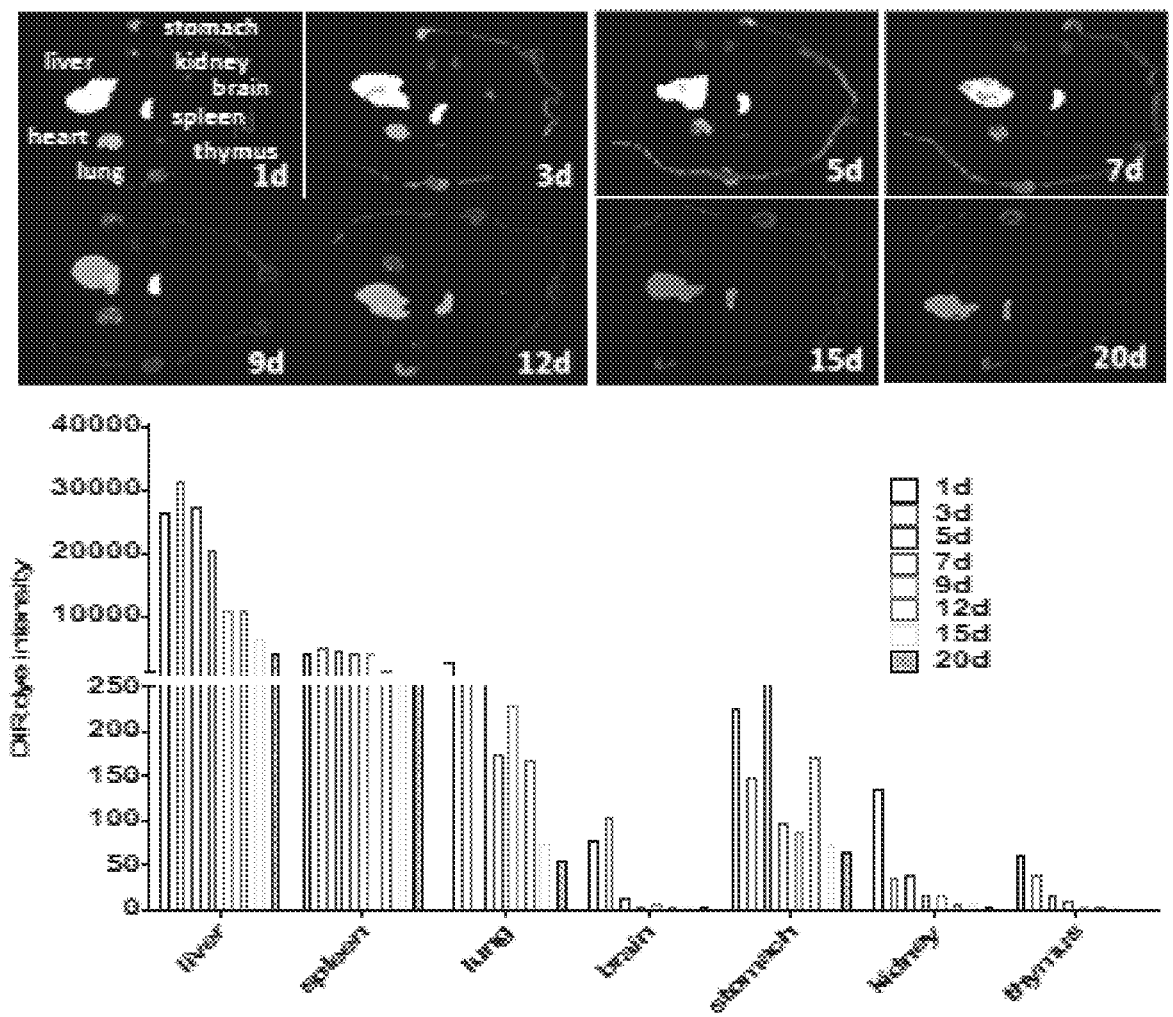
Figure 17F:
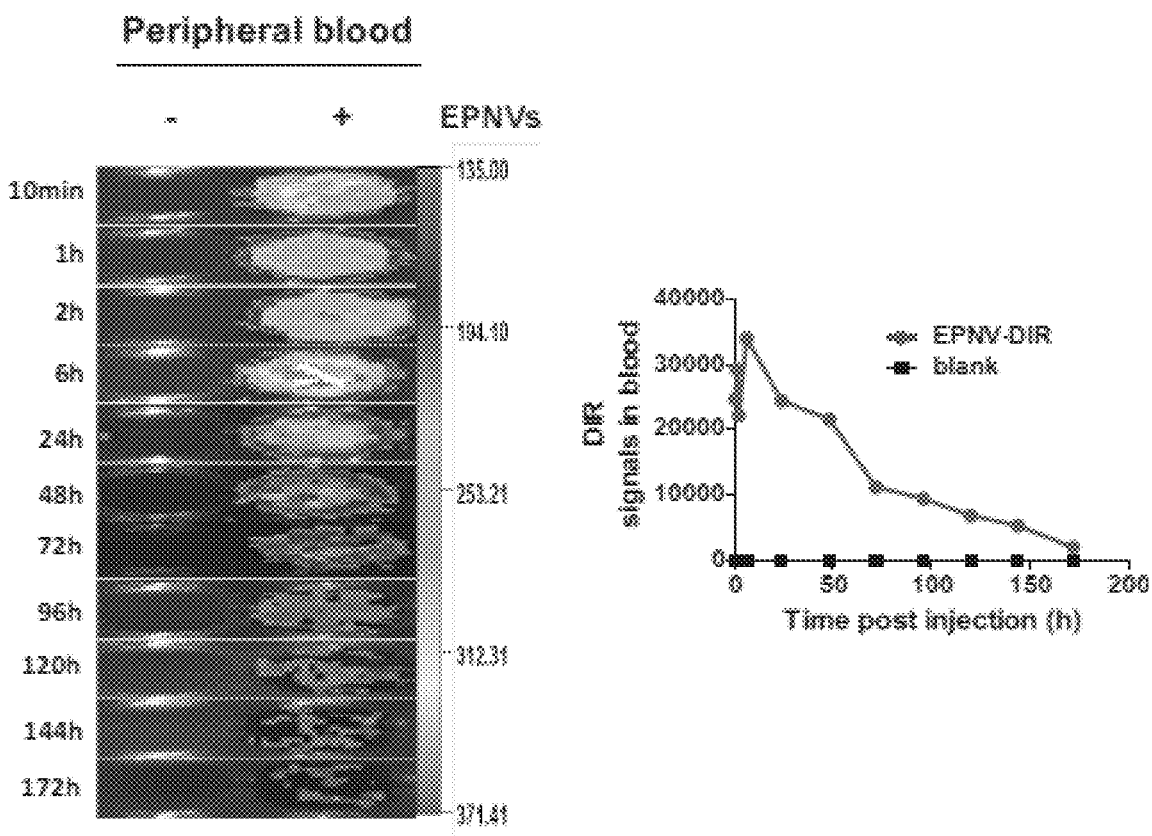
Figure 17G:
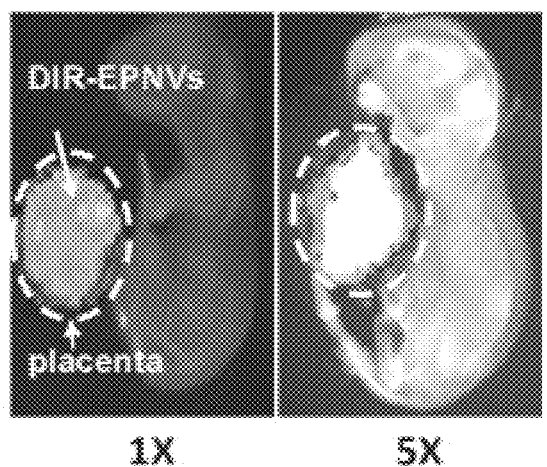

To determine the tissue tropism of EPNVs, in vivo biodistribution of DiR-labeled EPNV was evaluated in mice using a Kodak Image Station 4000 MM Pro system or the Odyssey imaging system. For these studies, the effect of different routes of injection on the distribution of DiR-labeled EPNV was first evaluated. 72 h after a tail-vein or intraperitoneal injection, DiR fluorescent signals were predominantly detected in liver, lung, kidney, and splenic tissues (FIG. 17B); whereas, intramuscularly injections of the DiR-labeled EPNVs were predominantly localized in muscle. After intranasal administration (FIG. 17C) of DiR-labeled EPNV the majority of the nano-vector was located in the lung and brain. The presence and intensity of the imaging signal further indicated that DiR-labeled EPNVs remain stable in the brain; whereas, no signal was detected in lung tissue 72 h after intranasal administration. FACS analysis was done on cells from mice receiving an intravenous injection of DiR-labeled EPNVs. FACS analysis indicated that EPNVs injected intravenously were taken up by splenic DX5$^+$ NK cells (10.9%) and F4/80$^+$ cells (12.7%), and liver F4/80$^+$ cells (4.65%), DX5$^+$ NK (1.75%), and CD19 B cells (1.63%) (FIG. 17D) 72 h after injection Upon analysis of the stability of intravenously injected DiR-labeled EPNVs, it was found that the fluorescent signals remained strong without a significant decrease in liver, spleen, and lung, while the signals were decreased significantly in the kidney at day 1 and in the brain at day 5 (FIG. 17E). In vivo imaging to continuously track the stability of injected DiR-labeled EPNVs further revealed that fluorescent signals remained strong in the liver and spleen at day 20 (FIG. 17E). Surprisingly, circulating DiR-labeled EPNVs were still detectable 7 days after a tail-vein injection (FIG. 17F). More importantly, unlike artificial nanoparticles that cross the placenta barrier in pregnant mice and cause pregnancy complications, in vivo imaging analysis showed that mice tail-vein injected with DiR labeled EPNVs had no EPNVs passing through the placenta (FIG. 17G), indicating that EPNV treatment can be safe for the fetus. Collectively, these data indicate that the stability of EPNVs is dependent on the microenvironment of tissues the EPNVs home to, and that the extended duration of circulating EPNVs can provide an opportunity for EPNVs to be available for a longer time in circulation and provide more time for the vector to eventually make it to its target.

Example 14—Assessment of In Vivo Cytotoxic Effects of the EPNVs

Figure 25A:
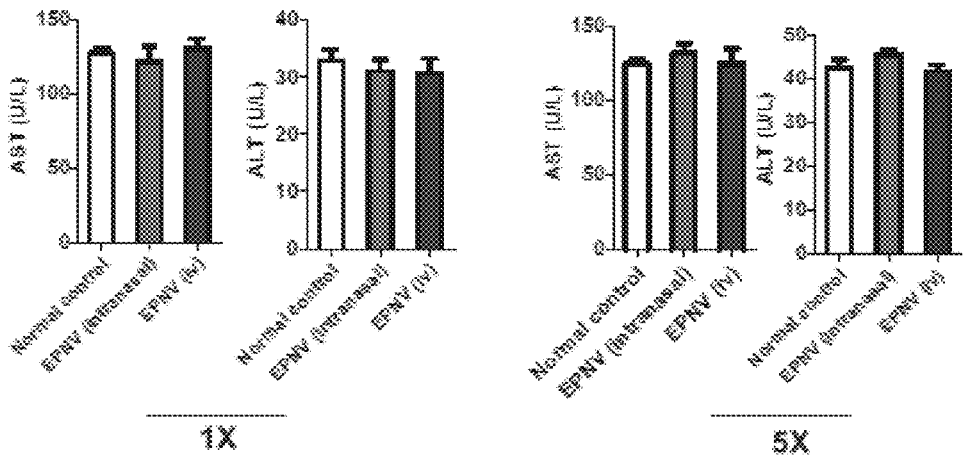
FIGS. 25A-25C include graphs and images showing the in vivo cytotoxicity analyses of EPNVs, including: a graph showing the sera levels AST and ALT liver enzymes in female C57BL/6j mice (n=5) injected i.v. with 100 nmol EPNV 1 (lx) or 5 times (5×) (FIG. 25A); graphs showing the levels of inflammatory cytokines in the mice (FIG. 25B); and haematoxilin and eosin stained sections of livers, spleens, kidneys, and lungs from EPNV-treated mice (FIG. 25C)
Figure 25B:
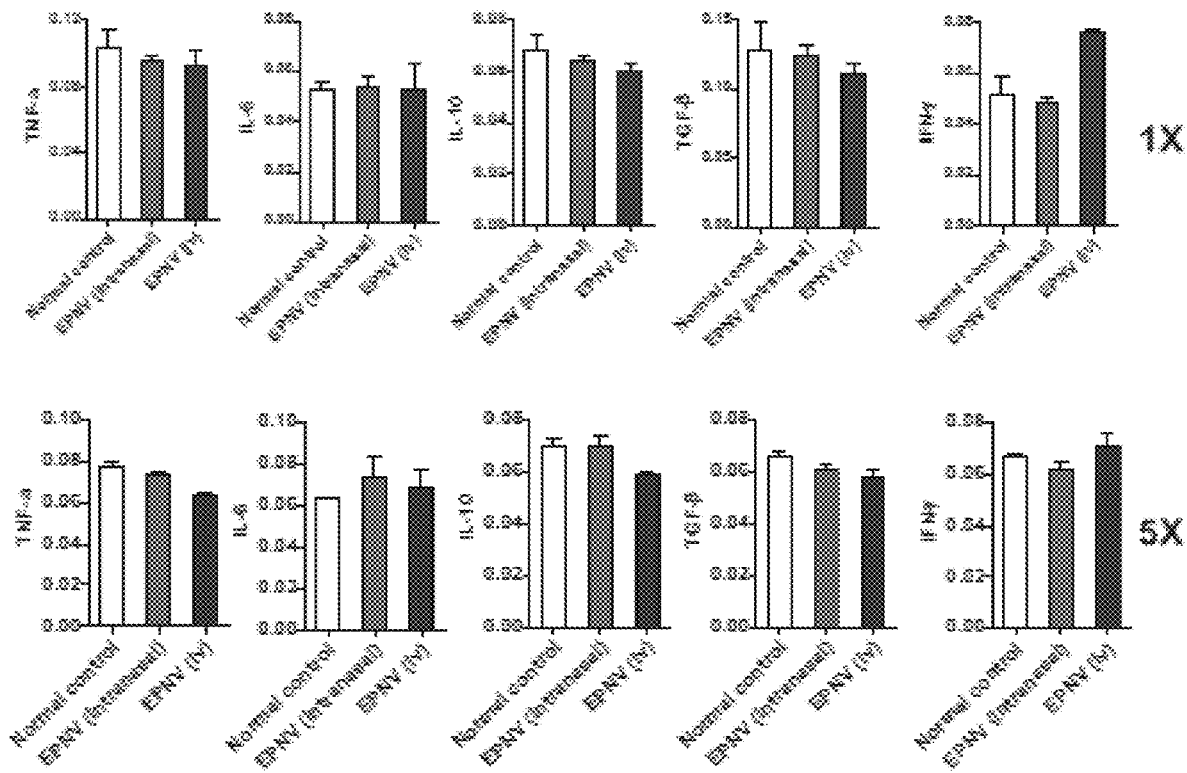
Figure 25C:
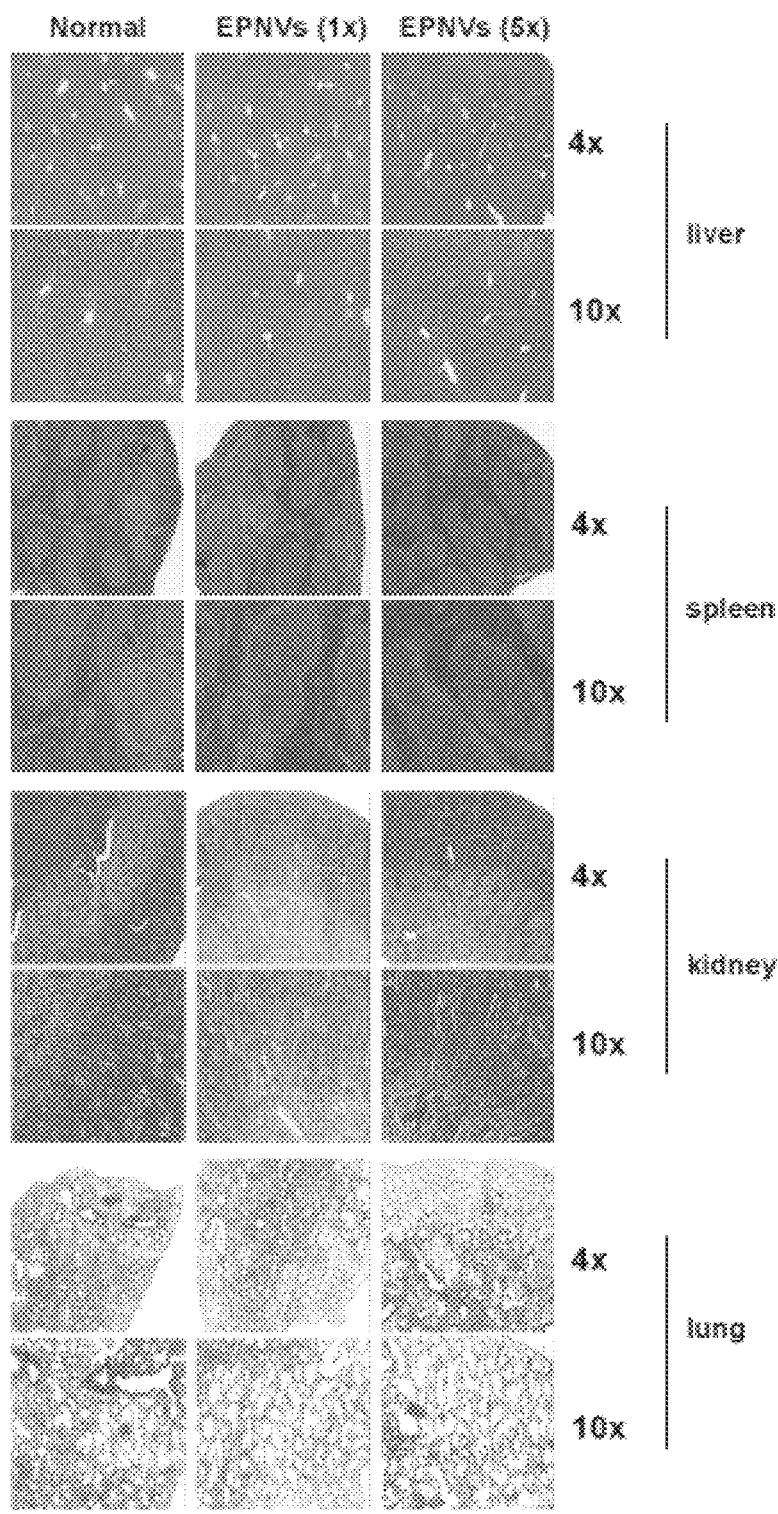

To further explore the potential in vivo cytotoxic effects of the EPNVs, proinflamamtory cytokines and indicators of liver injury were quantitatively determined. Serum levels of alanine aminotransferase (ALT) and aspartate aminotransferase (AST) of mice pretreated with EPNVs were measured for liver injury. ALT, AST (FIG. 25A) and proinflammatory cytokines (FIG. 25B) were not induced due to EPNV treatment. Histological analysis of tissues from treated animals and control animals (FIG. 25C) revealed no pathological changes in the lung, kidney, liver or spleen. Hepatocytes in the liver samples appeared normal, and there were no signs of inflammatory response. No pulmonary fibrosis was detected in the lung samples. Necrosis was not found in any of the histological samples analyzed.

Example 15—EPNVs as Candidates for Use as a Therapeutic Delivery Vector

Figure 18A:
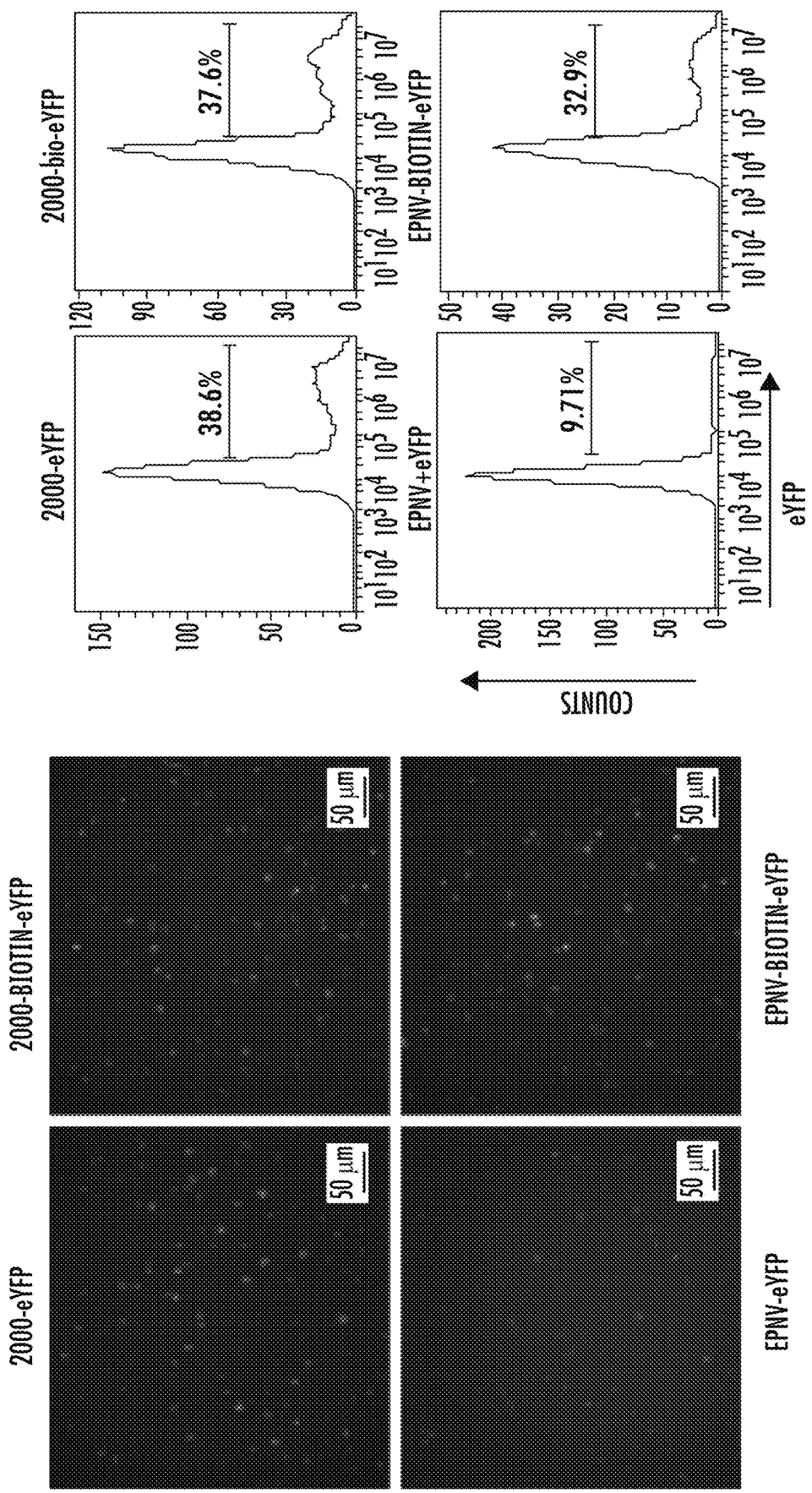
FIGS. 18A-18C are images and graphs showing EPNV delivery of biotinylated DNA expression vectors, antibodies and siRNA, including: images and graphs showing A549 cells transfected with biotinylated eYFP carried by EPNVs or LIPOFECTAMINE® 2000 (Invitrogen, Carlsbad, CA) where YFP positive cells were quantitatively analyzed by FACS (FIG. 18A); graphs showing the quantitative analysis of PKH26 positive cells, where PKH26-EPNVs loaded with biotin labeled anti-CD4 or anti-CD8 antibodies were incubated with splenocytes in vitro (FIG. 18B); and graphs showing the biological effect of luciferase specific siRNA carried by EPNVs or LIPOFECTAMINE® 2000 (Invitrogen, Carlsbad, CA) on inhibition of luciferase activity of transfected GL-26-luc and A549-luc cells (FIG. 18C)
Figure 18B:
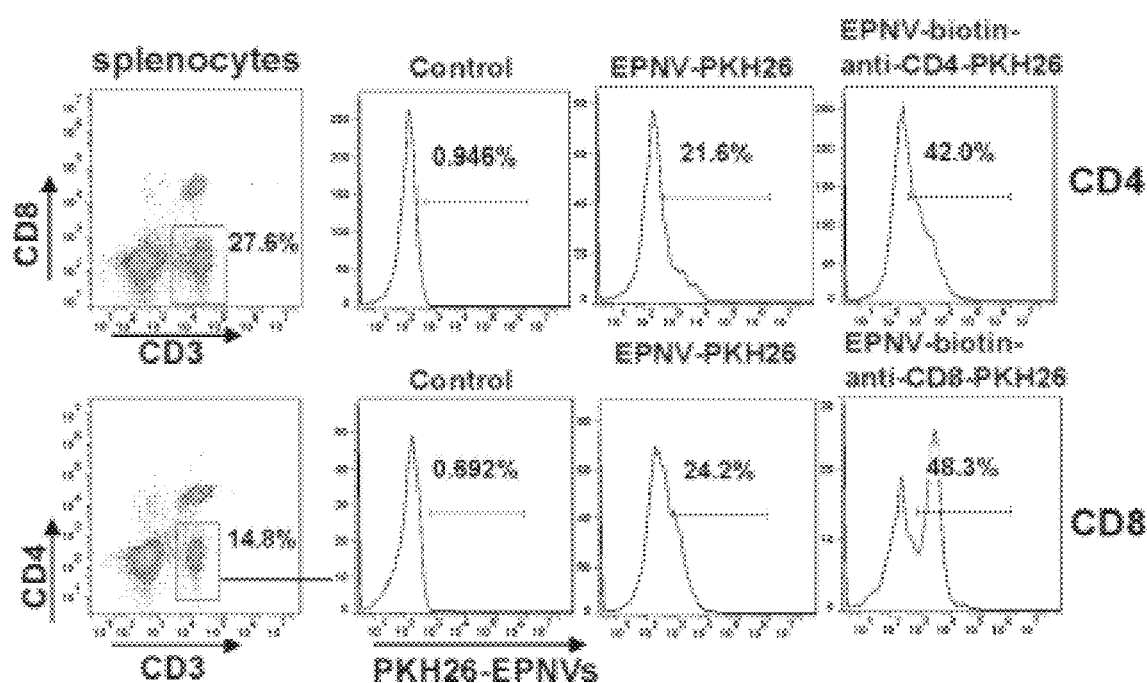
Figure 26:
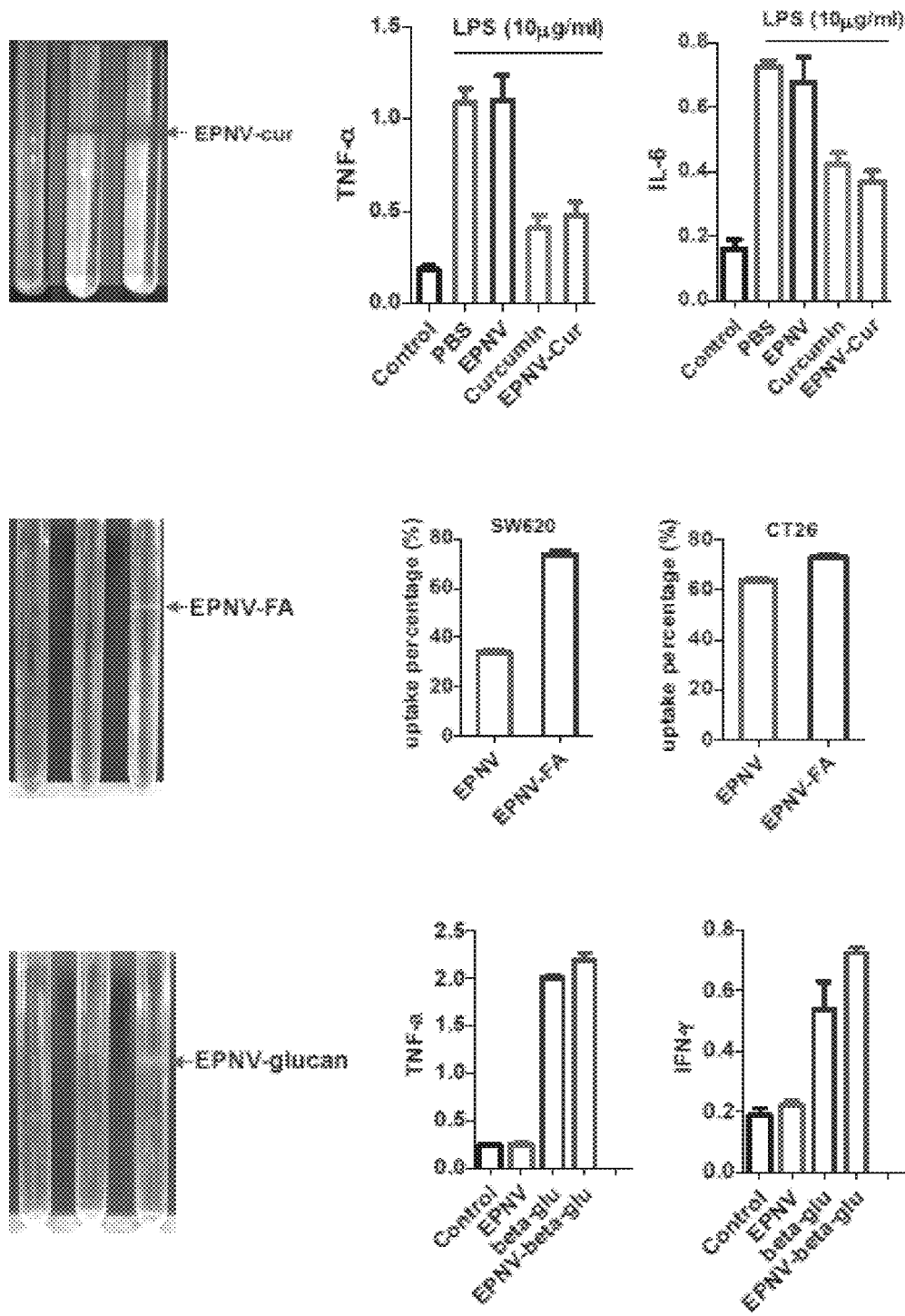
FIG. 26 includes images and graphs showing the ability of EPNVs to not affect the biological functions of agents carried by EPNVs, where the anti-inflammatory agent curcumin (top, left), folic acid (FA), a ligand of folate receptor (medium, left) and an immune stimulator, β-glucan (bottom, left) were loaded onto EPNVs and isolated on a sucrose gradient, and where curcumin mediated inhibition of induction of TNF-α and IL-6 produced by LPS (100 ng/ml) stimulated mouse splenocytes (top, right), FA mediated uptake of EPNVs by CT26 and SW620 cells (medium, right), and production of TNF-α and IFN-γ by β-glucan stimulated mouse splenocytes (bottom, right) was measured.
Figure 27:
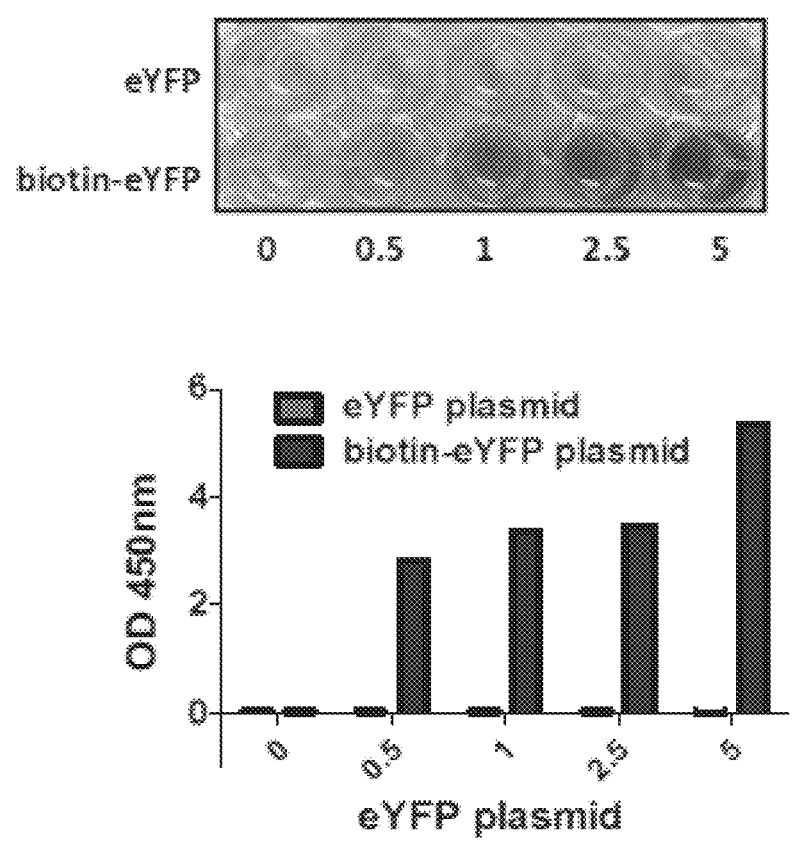
FIG. 27 includes an image and a graph showing the ability of EPNVs to carry a biotin labeled eYFP vector.

The molecular or drug therapy fields are limited by the lack of vehicles that permit high efficiency transfection of targeted cells without a resulting cytotoxicity or host immune response. The results presented in FIGS. 16A-F and FIGS. 25A-C demonstrated that EPNVs were taken up in a highly efficient manner by a number of different types of cells without causing cytotoxicity or an inflammatory cytokine induction. Next, it was determined whether EPNVs can deliver a broad range of the therapeutic agents such as chemotherapeutic drugs, siRNA, DNA expression vector, and proteins to targeted cells. Previous data suggested that nano sized particles released from mammalian cells favor binding to hydrophobic agents, such as curcumin and anti-stat3 J5124, resulting in increased stability, solubility and bioavailability of the drugs. Results presented in this study also show that EPNVs bind to hydrophobic agents including curcumin, folic acid and beta-glucan without altering the biological activities of the agents (FIG. 26). To further determine whether EPNVs can also carry an agent that can serve as a bridge to deliver therapeutic agents, biotin was chose as a candidate since biotin is a small (244.31 delta), hydrophobic molecule. Biotinylized eYFP DNA expression vector (FIG. 27) carried by EPNVs expressed the YFP protein in A549 cells as efficiently when transfected with LIPOFECTAMINE® 2000 (FIG. 18A). Furthermore, EPNVs carrying biotinylized proteins like anti-CD4 or anti-CD8 antibodies significantly enhance the transfection efficiency of $CD4^+$ or $CD8^+$ T cells (FIG. 18B). Collectively, these results indicated that EPNVs are capable of delivering both biotinylized DNA, as well as proteins to targeted cells.

Figure 18C:
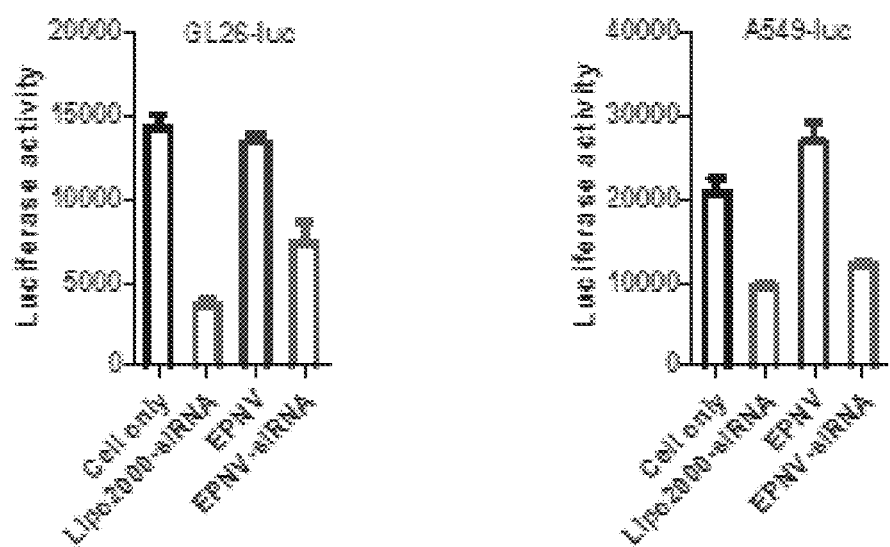

To determine whether EPNVs would encapsulate and deliver functional siRNAs, a well-characterized siRNA that is directed against a luciferase reporter gene stably expressed in GL26-Luc was used. Transfection was conducted with 15 pmol luciferase siRNA delivered by EPNVs or by a standard LIPOFECTAMINE® 2000 transfection agent. It was found that luciferase siRNA carried by EPNVs effectively inhibited the expression of the luciferase gene when compared with the LIPOFECTAMINE® 2000 untreated cells (FIG. 18C). In summary, the results showed that EPNVs are an effective delivery vector for all the agents tested.

Figure 19A:
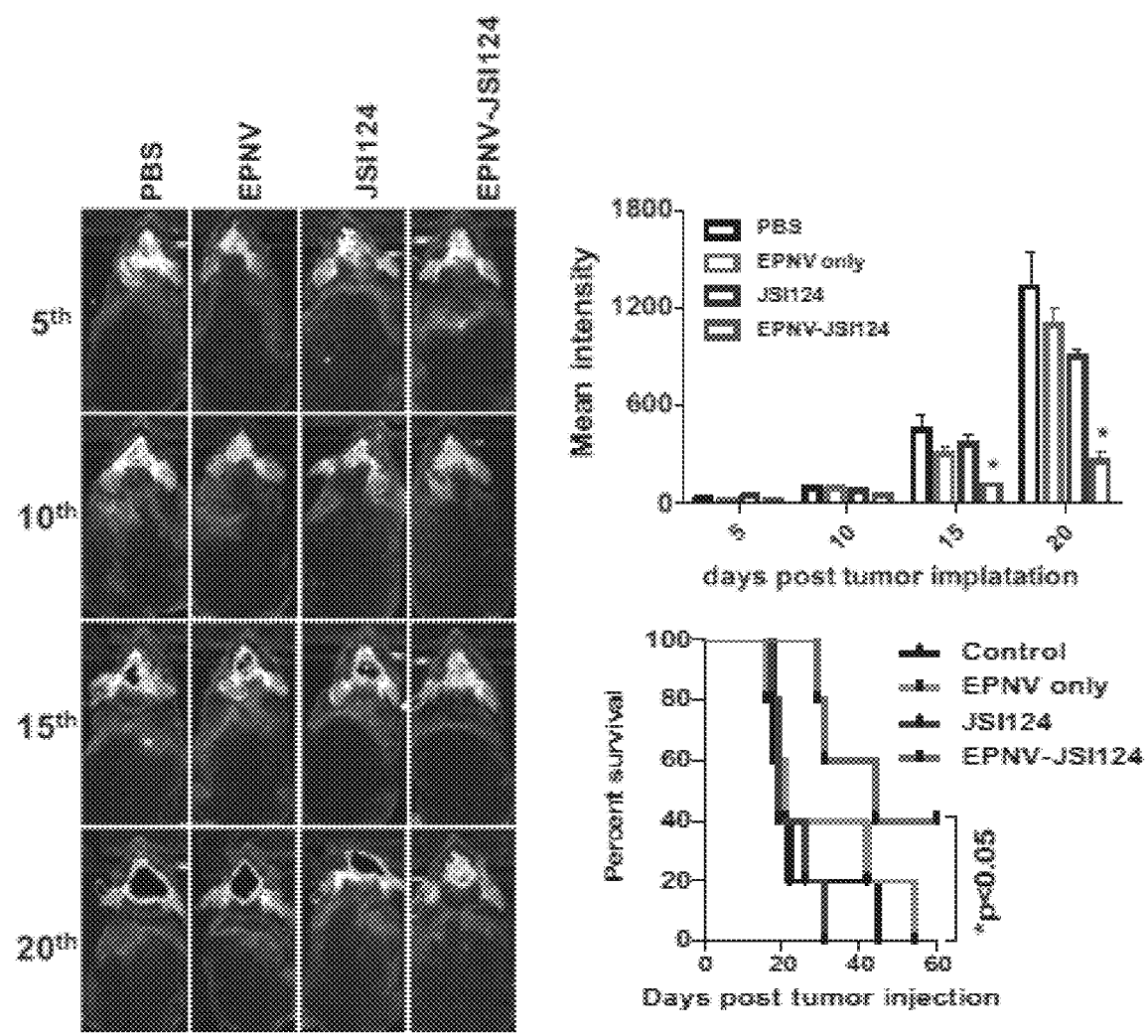
FIGS. 19A-19E include graphs and images showing the ability of EPNVs to carry anti-cancer therapeutic agents using a targeting moiety to tumor tissue, including: images and graphs showing the results of experiments where C57BL/6J mice were implanted with GL26-Luc cells, EPNVs were loaded with Stat3 inhibitor JSI-124 and then intranasally administered to mice, and where the mice were imaged on post-injection days as indicated, the growth potential of injected GL26-Luc cells was determined by dividing photon emissions of mice treated with PBS by the photon emissions of mice treated with EPNV, JSI124, or EPNV-JSI124, and where the percent of EPNV-JSI124-treated mice surviving was compared to control mice (FIG. 19A); images and graphs showing EPNV-mediated targeting co-delivery of PTX and folic acid to mouse CT26, human SW620 colon tumors and the mouse 4T1 breast tumor (FIG. 19B); and graphs showing the tumor volume in mice subsequent to the injection of tumor cells into BALB/c mice (CT26, and 4T1, $1\times10^6$/mouse) or NOD-SCID mice (SW620, $5\times10^6$/mouse) (FIG. 19C); images and graphs showing the tumors and DiR fluorescent signals of the tumor 30 days post-implantation (FIG. 19D); images and graphs showing EPNV-mediated in vivo delivery of siRNA to tumors, where CT26-Luc tumor cell-bearing mice were intravenously injected with luciferase siRNA (50 pmol/mouse in 200 nmol EPNVs), luciferase siRNA carried by EPNVs, or folic acid and luciferase siRNA co-delivered by EPNVs (FIG. 19E)
Figure 28:
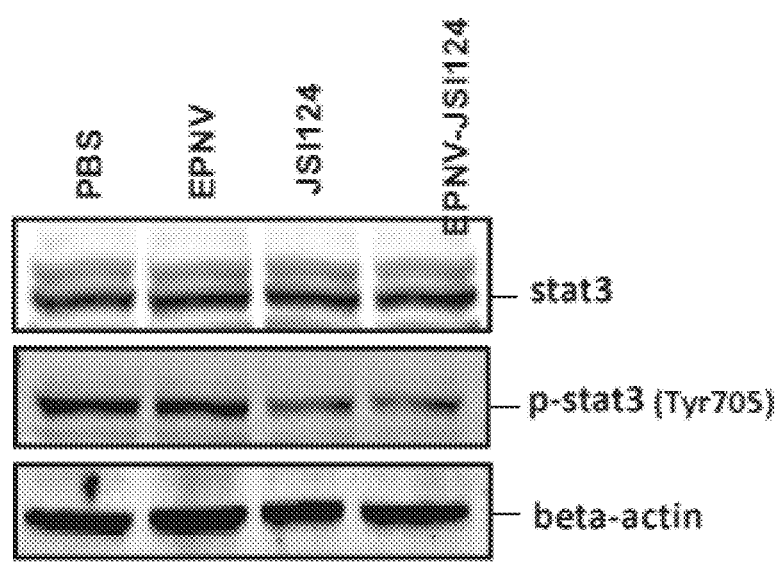
FIG. 28 is an image showing a western blot analysis of the expression of phosphorylated stat3, where A549 cells were treated with PBS, EPNV, JSI124 or EPNVs-JSI124 and the expression of p-Stat3 and Stat3 was analyzed by western blots.

Example 16—In Vivo Delivery of Therapeutic Agents with EPNVs and Co-Delivery of FA and Therapeutic Agents for Targeting to Tumor Tissues and Inhibition of Tumor Growth It is appreciated that EPNVs are capable of carrying the anti-Stat3 inhibitor, JS124, and that mice given an intranasal dose of nano-sized mammalian cell-derived exosomes carrying JS124 had significant inhibition of GL26 tumor growth. In that regard, it was hypothesized that EPNVs can also deliver JS124 to the brain via a non-invasive route and subsequently inhibit implanted GL26 tumor growth. In initial experiments, inhibition of Stat3 activity by EPNV-JS124 or JS124 was evaluated in 24 h cell cultures. Western blot assays revealed that JS124-loaded EPNV significantly inhibited the activation of Stat3 in comparison with GL26 tumors treated with EPNVs only, JSI-124 only, or PBS as controls (FIG. 28). Based on the western blot results from cell cultures, groups of GL26L tumor-bearing mouse (n=5) were administrated intranasally EPNV encapsulated Stat3 inhibitor JSI-124 (12.5 pmol/10 µl), EPNV only, JSI-124 only, or PBS. Bioluminescent imaging of the mice treated as described above was used to quantify Luc expression in relation to the GL26 tumor growth. FIG. 19A compares brain-associated photons obtained from the above groups on days 5, 10, 15 and 20. A representative image (left panel) or imaging data (right panel, top) showed the weakest luciferase activity relative to growth of tumors from the mice treated with EPNV encapsulated Stat3 inhibitor JSI-124 compared with other groups. These results were further confirmed by the survival rates of mice. Survival of the PBS-, EPNVs- or JSI124-control animals ranged from 20 to 30 days. In contrast, EPNV-JSI124 treatment significantly prolonged the survival of mice to an average of 42.5±2.3 days ($P<0.05$) (FIG. 19A, right panel, bottom).

Figure 19B:
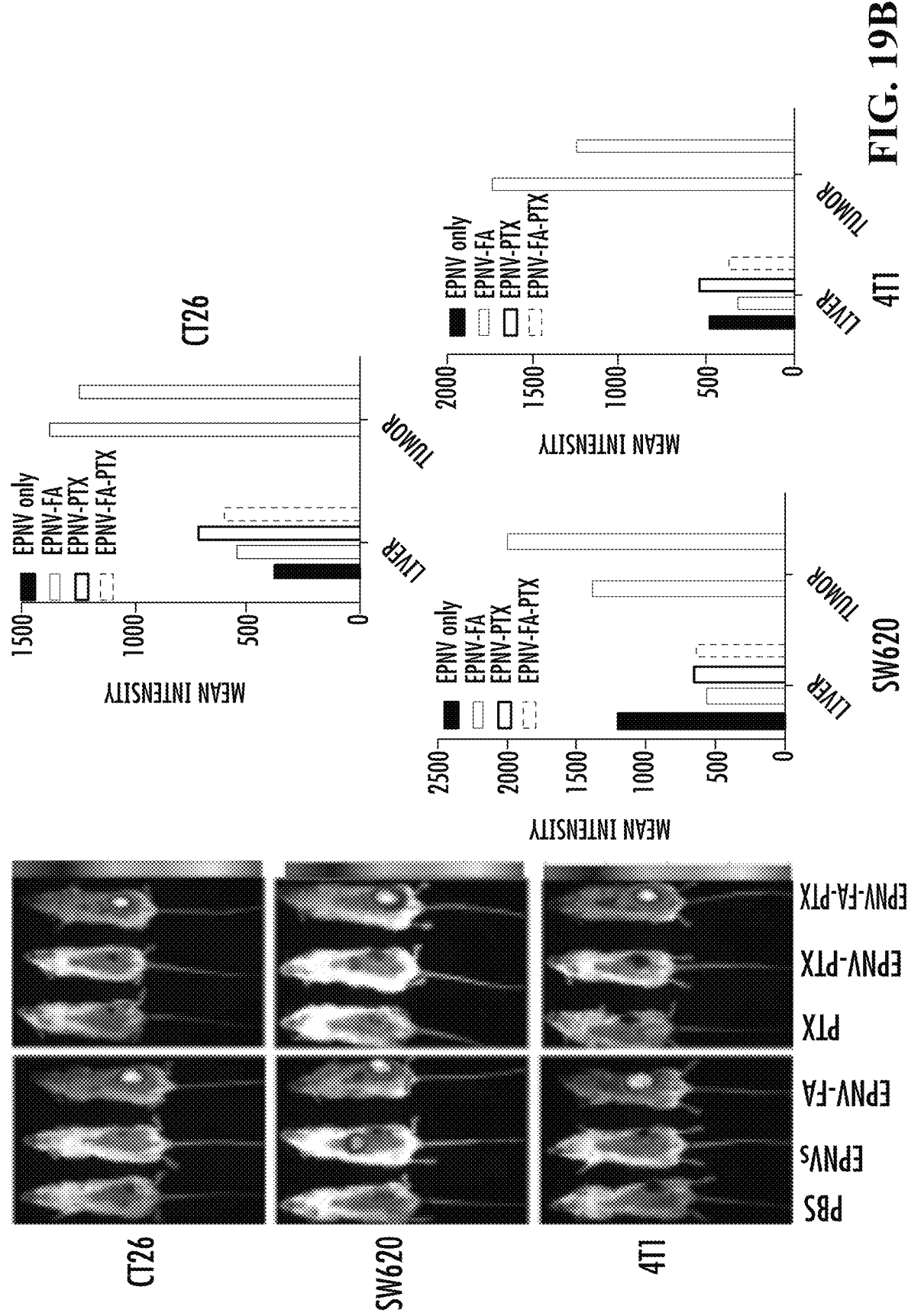
Figure 19C:
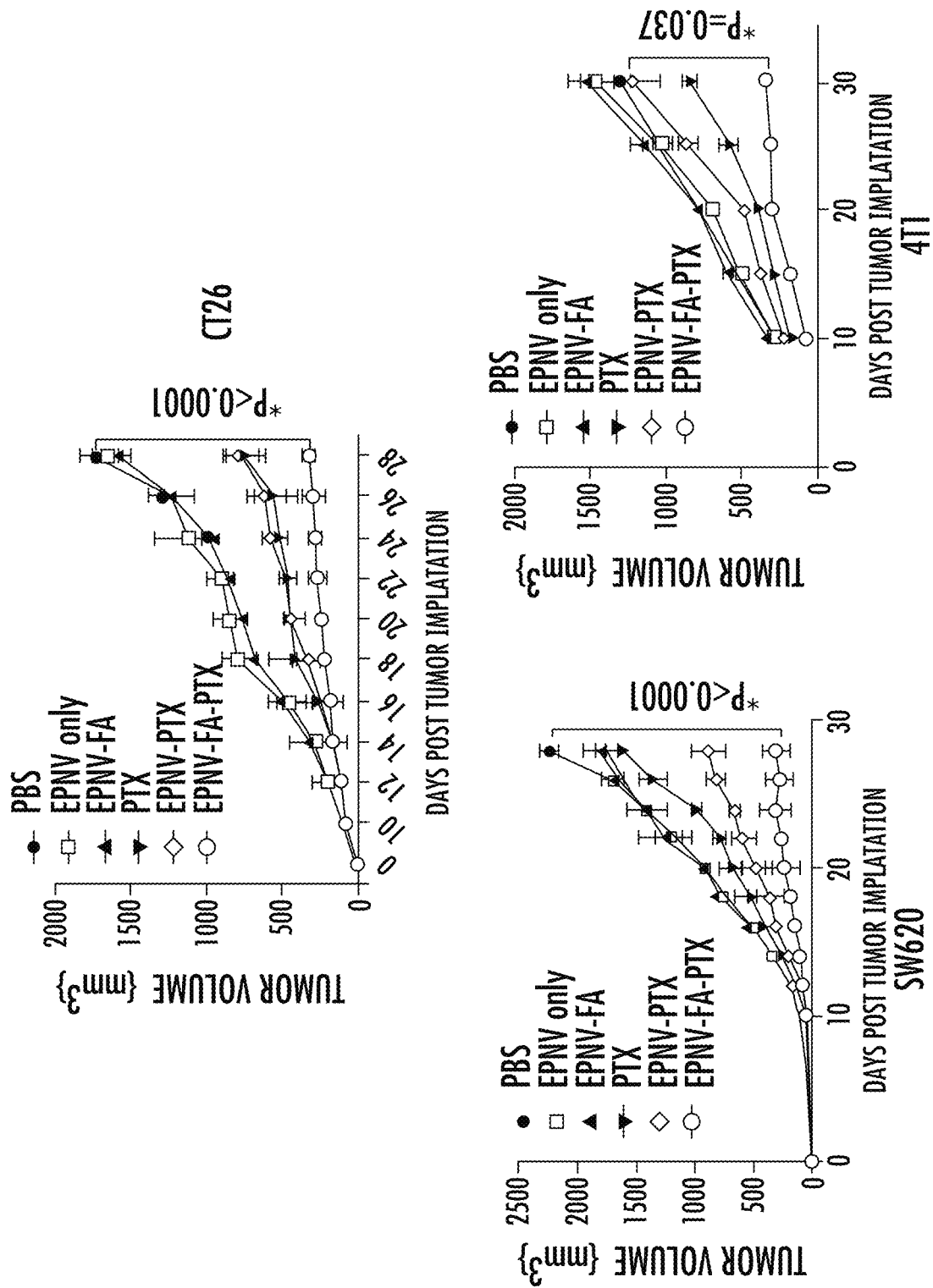
Figure 19D:
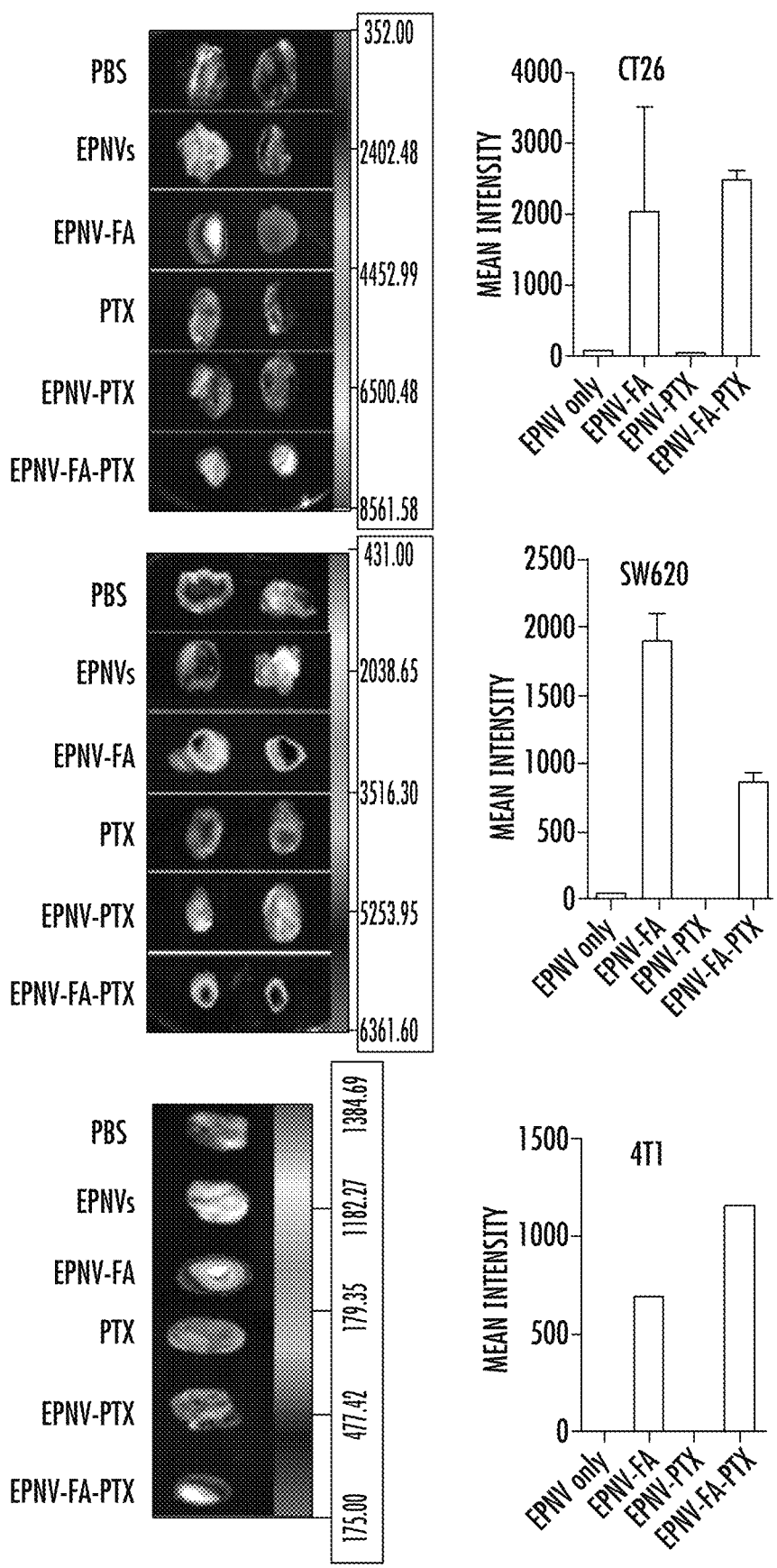
Figure 19E:
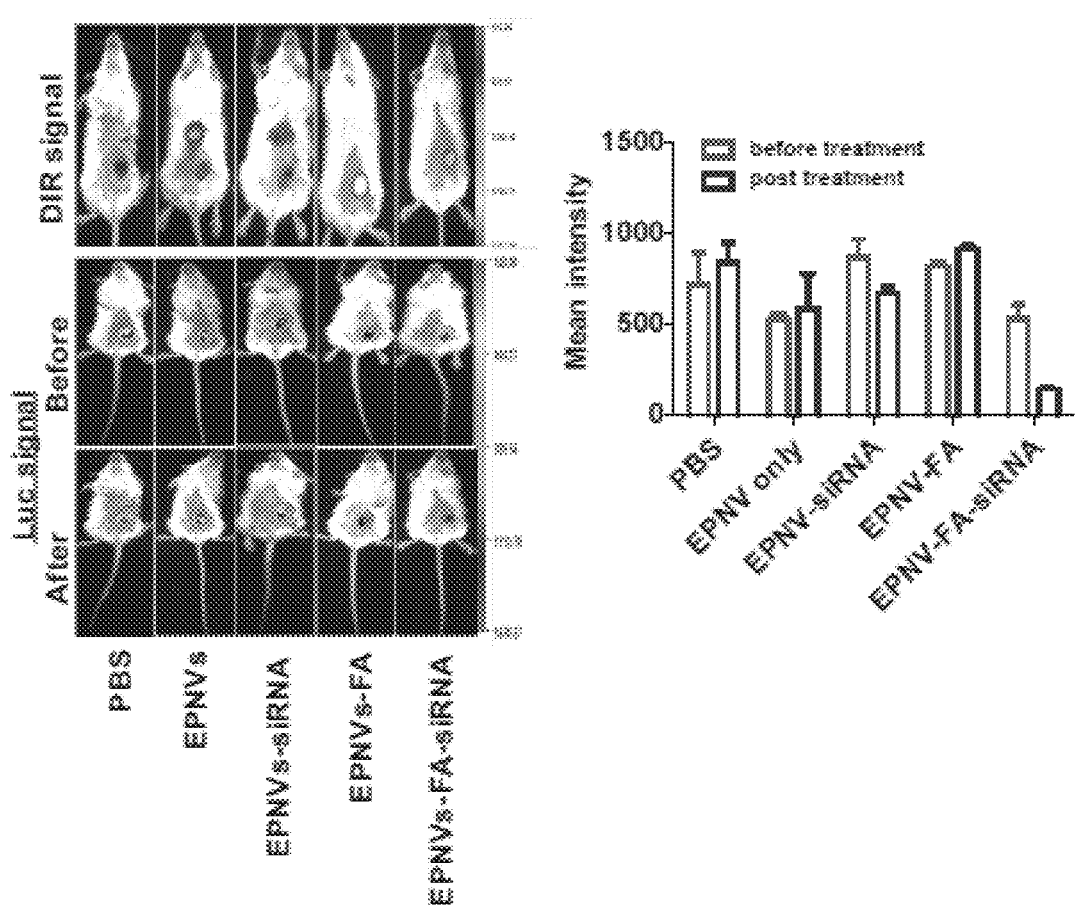
Figure 29:
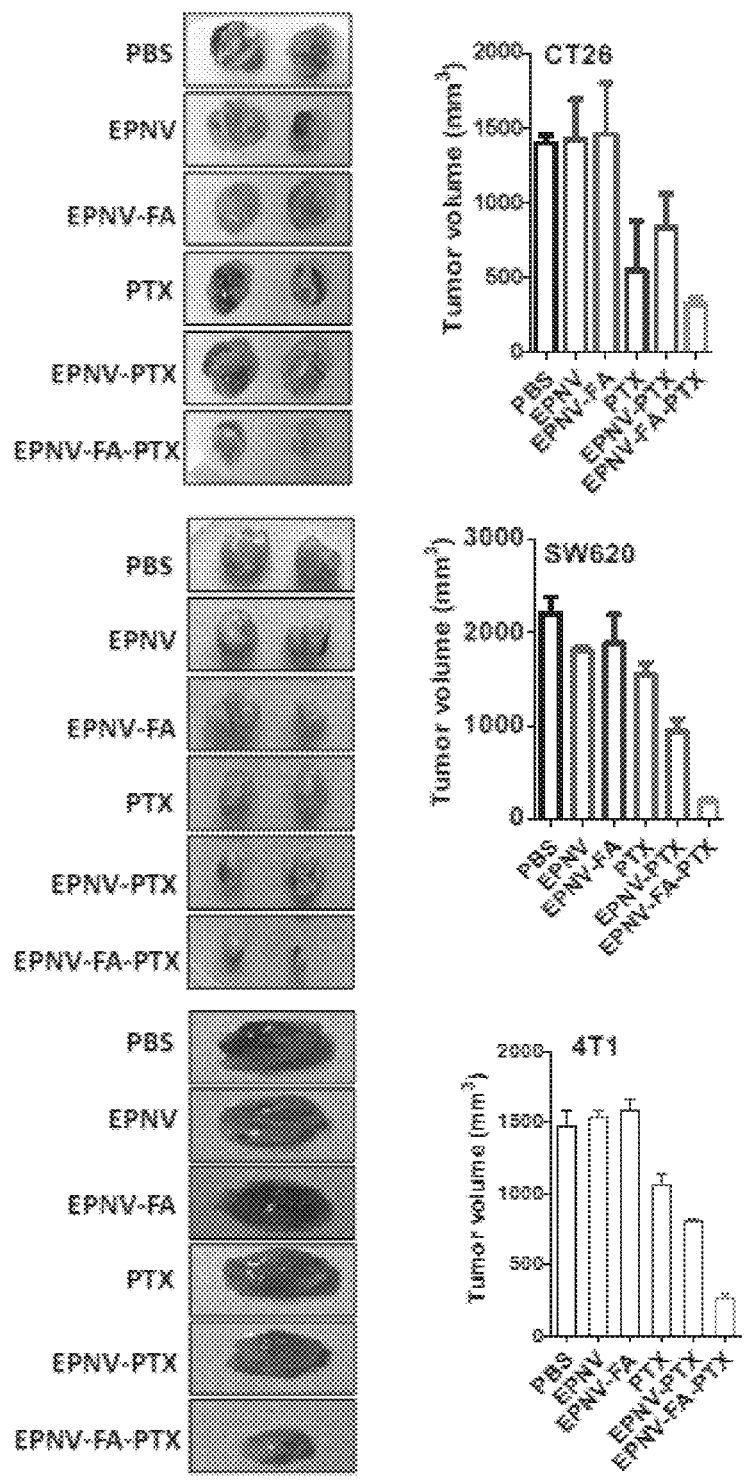
FIG. 29 includes images and graphs showing tumor sizes of three folic acid-mediated EPNV targeting tumor models, where on day 30 after injecting mice with tumor cells, the mice were sacrificed and CT26 tumors (top), SW620 tumors (medium) and 4T1 (bottom) were removed, photographed (left) and the size measured (right)
Figure 30A:
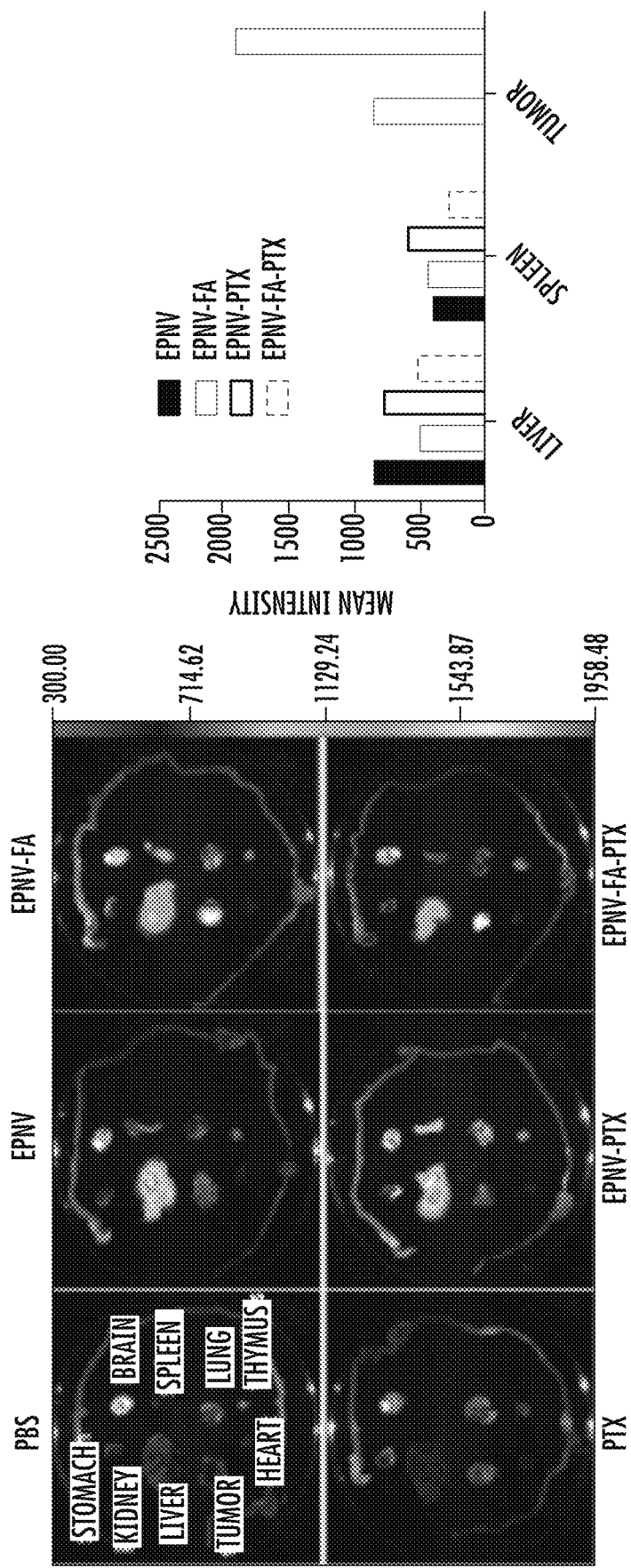
FIGS. 30A-30C include images showing the biodistribution of EPNV, EPNV-FA, EPNV-PTX and EPNV-FA-PTX, where on day 30 after injecting mice with tumor cells, mice were sacrificed, the organs (spleen, liver, kidney, brain, lung, heart, thymus and gut) removed and the distribution of DIR dye labeled EPNVs was images and the signals quantified.
Figure 30B:
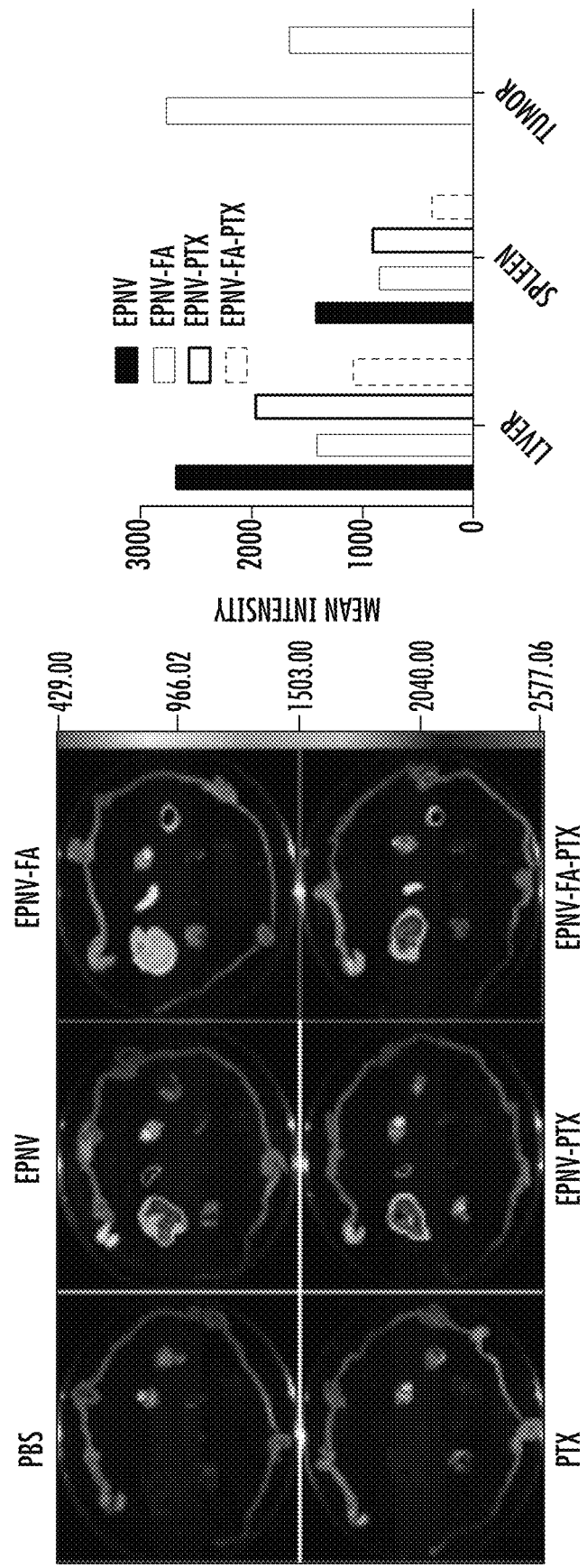
Figure 30C:
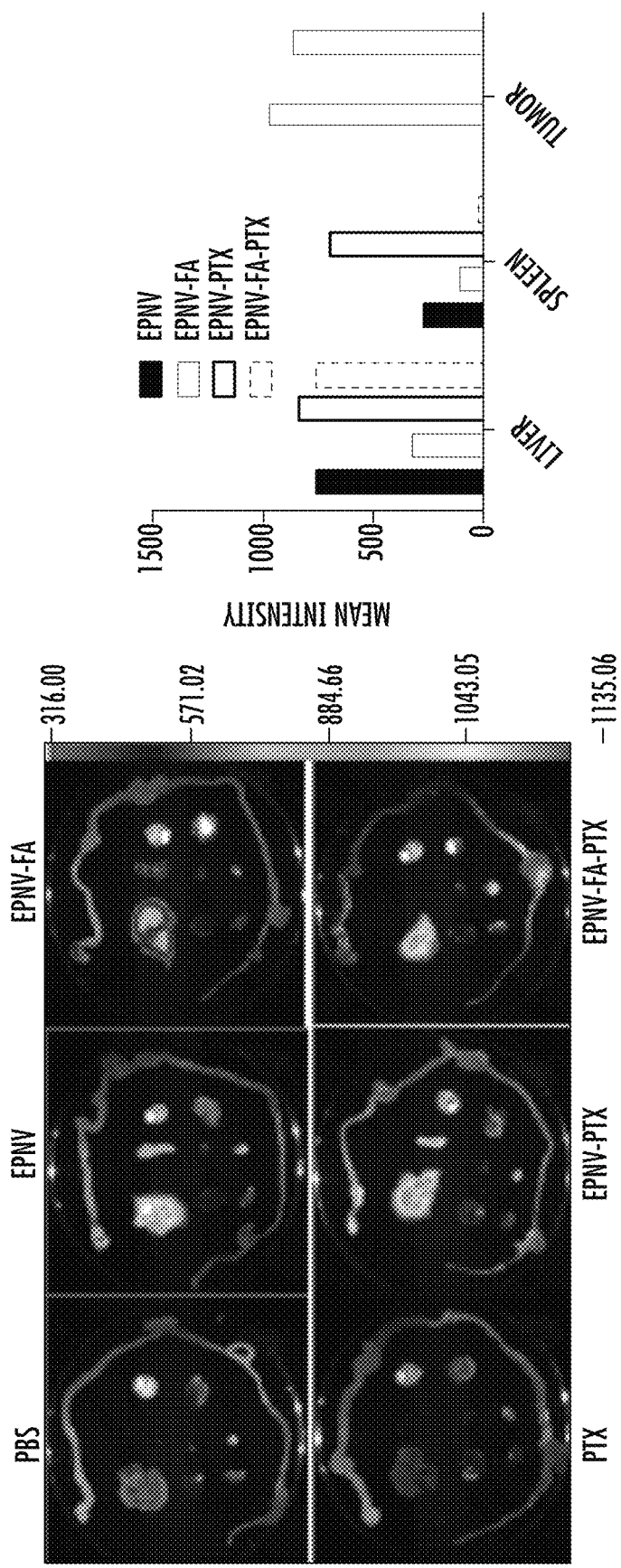

In cancer therapy accurate targeting of tumor tissue is required for successful therapy. Therefore, whether EPNVs can be modified to achieve tumor targeting was tested. High-affinity folate receptors (FRs) are expressed at elevated levels on many human tumors and in almost negligible amounts on non-tumor cells. As such, three tumor xenograft models (FIG. 19B) including the mouse CT26 colon cancer model, the human SW620 colon cancer SCID mouse model and the 4T1 breast tumor model were used to test whether EPNV binding folic acid (FA) would significantly enhance EPNVs targeting to tumor in a physiologic milieu. EPNVs were labeled with DiR dye for molecular imaging. 72 h after intravenous injection of DiR dye labeled EPNVs, no DiR-labeled EPNV signals were detected in tumor tissues with most signal being detected in the liver (FIG. 19B, the second columns from left). In contrast, intravenously injected DiR-labeled EPNV-FA exhibited a much higher distribution to tumor tissues (FIG. 19B, the third column from left). Co-delivery of FA with a chemotherapeutic drug (PTX) by EPNVs has at least equal efficiency as EPNV-FA in targeting to tumor tissue (FIG. 19B), suggesting that co-delivery of FA with chemotherapeutic agents has no effect on FA mediated targeting. Quantification of photons showed that DiR-labeled EPNV-FA distribution to tumor tissues was more than 1300-fold (CT26 model), 1600-fold (SW620), and 1400-fold (4T1 breast tumor model) greater than that of DiR-labeled EPNVs (FIG. 19B, right panels). Next, it was determined if co-delivery of FA with a therapeutic drug (PTX) by EPNVs would have better therapeutic effect than the drug alone. As expected, the EPNV-FA-PTX treatment caused a substantial decrease in tumor growth in all three tumor models. The tumor growth was significantly lower after treatment with EPNV-FA-PTX, an effect that was evident from day 20 (all three tumor models) (FIG. 19C). On day 30, the tumor volume in the PTX loaded EPNV-FA group was 261.7±28 2 mm$^3$, significantly smaller that than in other groups (FIG. 29). Consistent with the inhibition of tumor growth, FA carried by EPNVs significantly enhanced the signal of DiR labeled EPNV-FA or EPNV-FA-PTX in tumor tissues in all three tumor models (FIG. 19D), indicating that the effect is attributable to the FA. In vivo biodistribution results with EPNVs, EPNV-FA, PTX and EPNV-FA-PTX from sacrificed tumor bearing mice illustrated that free EPNVs and PTX mainly targeted liver and spleen, but FA or FA-PTX loaded EPNVs primarily targeted tumors (FIG. 20). It was further demonstrated that not only did EPNV-FA enhance the therapeutic effect of a chemotherapeutic drug by inhibiting implanted tumor growth, but it also dramatically enhanced the efficiency of delivery of siRNA to tumor. As shown in FIG. 19E, intravenous injection of EPNV-FA-siRNA-Luc led to more than a 5-fold reduction in luciferase activity in CT26 tumor cells compared with EPNV-siRNA-Luc under the same conditions.

Discussion of Examples 11-16

A number of strategies, including nanotechnology, and viral and non-viral delivery systems, have been used to experimentally determine the most suitable vector for treatment of diseases. Each of these approaches has advantages. However, potential toxicity, tissue specific targeting, hazardous effect on the environment, and large scale economical production are challenging issues confronting this technology. The present approach of using edible plant derived nanoparticles to make a nano-vector has the advantage of having no-detectable toxicity, the potential of being manipulated/modified for redirected targeting, the capacity to deliver varied, multiple agents and can be produced economically.

A preparation process is required for practical large-scale generation of nanoparticles that can be loaded with multiple drugs. The present use of differential centrifugation followed by sonication allowed for large scale production of an edible fruit derived nano vector. The present process is another major advantage over the multiple steps and sophisticated techniques required for in vitro synthesis of artificial or mammalian based nanoparticles. The present results show that the nano-vector produced as described can serve as the basis for developing more customized therapeutic delivery vehicles based on the disease. The incorporation of biotinylated therapeutic agents into a nano-vector considerably broadens the range of therapeutic agents and targeting moieties that could be delivered. A variety of substances including protein, peptides, nuclear acids, and chemotherapeutic agents can be biotinylated. The vector technology presented in this study as applied to cancer therapy can also be used for treatment of many other types of diseases by co-delivering therapeutic drugs with tissue specific targeting agents.

The foregoing studies also demonstrated that chemotherapeutic drugs as well as siRNAs can be encapsulated into the nano vector and that their biological effects in vivo are not then altered. This is an aspect for improving the delivery of siRNAs/miRNAs and chemotherapeutic drugs, especially, hydrophobic drugs. Stand-alone chemotherapy drugs suffer from numerous problems including rapid in vivo metabolism and/or excretion, an inability to access and penetrate cancer cells, and nonspecific uptake by healthy cells and tissue. Often a large percentage of a cytotoxic drug administered to a patient does not reach the tumor but is distributed throughout the body, causing the numerous toxic effects associated with chemotherapy reducing its therapeutic usefulness. In contrast, our nano-vector is derived from edible plant tissue and is composed of biocompatible and biodegradable materials, encapsulates a wide range of drugs and drug classes, has the ability to attach in a targeting fashion to specific cell types or groups, protects the therapeutic agent from degradation and delivers the therapeutic agent directly to the site of disease.

The size of a nanoparticle is a factor that can prevent renal clearance (typically less than 20 nm), prevent uptake by the liver and spleen (particles greater than 150 nm), and enhance accumulation in the tumor (particles between 50-150 nm). One advantage of the nano-vector described herein is that the size can be further manipulated by changing the frequency at which the nano-vector passes through a high pressure homogenizer. This allows the vector size to be tailored for specific therapeutic treatments. An additional advantage of the presently-described nano-vector is its retention in the circulation for extended periods. The foregoing data showed that the nano-vector was detected on day 7 after intravenous injection. The longer the nano vector is in circulation, the more opportunity for the ERP effect and subsequent penetration into tumor tissues. The EPR effect in combination with active targeting by the nano vector would enhance the therapeutic effect.

In summary, the foregoing studies show that specially designed nano-vectors derived from edible grapefruit nanoparticle lipids could shift the current paradigm of drug delivered by artificially synthesized nanoparticles to using nano vectors derived from edible plants. It is conceivable that nano-vectors derived from edible plants could be among the safest therapeutic vectors because they do not cause cytotoxic reactions. In addition, mice treated via intranasal delivery with the nano-vector carrying a therapeutic drug have a significantly delayed tumor growth in the brain, and treated intravenously, it was found that the nano vector does not cross the placenta to the fetus. Collectively, the data generated in this study indicated that the presently-described edible plant derived nano-vector would be safe for clinical use. The foregoing studies demonstrate the successful inhibition of tumor growth in four independent murine cancer models using the nano vector, and indicated that it can be used as a delivery vehicle for treatment of various types of cancer. Furthermore, the foregoing studies showed that a large quantity of nanoparticles can be isolated from a number of edible plants and that a large quantity of non-toxic nano-vector can be generated from different edible plant sources at affordable prices.

Throughout this document, various references are mentioned. All such references are incorporated herein by reference, including the references set forth in the following list:

REFERENCES

1. Sun et al. (2010) Mol Ther 18:1606-1614.
2. Thery et al. (2009) Nat Rev Immunol 9:581-593.

3. Yu et al. (2007) J Immunol 178:6867-6875.
4. Sun et al. (2010) Mol Ther 18:1606-1614.
5. Regente et al. (2009) 583:3363-3366.
6. An et al. (2007) Plant Signal Behav 2:4-7.
7. An et al. (2006) Cell Microbiol 8:1009-1019.
8. Liu et al. (2006) J Immunol 176:1375-1385.
9. Roger et al. (2009) J Control Release 140:174-181.
10. Yin et al. (2009) Biomaterials 30:5691-5700.
11. Linkov et al. (2009) Eur Cytokine Netw 20:21-26.
12. Sarmento et al. (2007) Biomacromolecules 8:3054-3060.
13. Damge et al. (2007) J Control Release 117:163-170.
14. Li et al. (2007) Int J Pharm 329:182-191.
15. Langguth et al. (2005) Drug Dev Ind Pharm 31:319-329.
16. Arbos et al. (2004) J Control Release 96:55-65.
17. Florence et al. (1995) J Drug Target 3:65-70.
18. Liu et al. (2006) J Immunol 176:1375-1385.
19. Liu et al. (2003) J Clin Invest 112:1332-1341.
20. Zhang et al. (2001) Arthritis Rheum 44:1555-1567.
21. Zhang et al. (2000) Arthritis Rheum 43:1094-1105.
22. Li et al. (2009) Mol Pharmacol 76:81-90.
23. Zhang et al. (2008) J Cell Biochem 103:1219-1230.
24. Fullbeck et al. (2005) BMC Cancer 5:97.
25. Uhle et al. (2003) EMBO J 22:1302-1312.
26. Bech-Otschir et al. (2001) EMBO J 20:1630-1639.
27. Zhang et al. (2002) J Immunol 168:4164-4172.
28. Yen et al. (2010) J Agric Food Chem 58:7376-7382.
29. Dandekar et al. (2010) Food Chem Toxicol 48:2073-2089.
30. Onoue et al. (2009) J Pharm Sci 99:1871-1881.
31. Anand et al. (2009) Biochem Pharmacol 79:330-338.
32. Shaikh et al. (2009) Eur J Pharm Sci 37:223-230.
33. Mitchison & Fourie (2010) Tuberculosis (Edinb) 90:177-181.
34. Pokharkar et al. (2009) J Biomed Nanotechnol 5:233-239.
35. Nohynek et al. (2009) Toxicol Appl Pharmacol 243:239-259.
36. Bennewitz et al. (2009) Neurotherapeutics 6:323-336.
37. Ghosh et al. (2009) Life Sci 84:75-80.
38. Kim et al. (2008) Inhal Toxicol 20:575-583.
39. Borm et al. (2006) Part Fibre Toxicol 3:11.
40. Duncan & Izzo (2005) Adv Drug Deliv Rev 57:2215-2237.
41. Li et al. (2005) J Nanosci Nanotechnol 5:1199-1203.
42. Hutter et al. (2010) ACS Nano 4:2595-2606.
43. Grizzle et al. (2002) Int J Cancer 101:270-279.
44. Xiang et al. (2011) Oncogene 30:3440-3453.
45. Brown et al. (2011) Infection and Immunity 79:1863-1872.
46. Cao et al. (2011) Differentiation 81:1-10.
47. Hughes et al. (2011) Inflamm Bowel Dis 17:213-220.
48. Lee et al. (2010) Gastroenterology 139:869-881, 881 e861-869.
49. Kuhnert et al. (2004) Proc Natl Acad Sci USA 101:266-271.
50. Ding et al. (2011) Stem Cells Dev 21:121-132.
51. Guo et al. (2011) Eur J Immunol 41:1098-1107.
52. Chen et al. (2110) Head Neck 33:1115-1125.
53. Lukacs et al. (2010) Cell Stem Cell 7:682-693.
54. Subkhankulova et al. (2010) Mol Cell Neurosci 45:151-162.
55. Xiang et al. (2009) Int J Cancer 124:2621-2633.
56. Zhang et al. (2000) J Clin Invest 105:813-821.
57. Zhuang et al. (2011) Mol Ther 19:1769-1779.
58. Sheth et al. (2012) Curr Drug Deliv 9:269-284.
59. Sharma et al. (2012) Expert Opin Drug Metab Toxicol 8:47-69.
60. Chidambaram et al. (2011) J Pharm Pharm Sci 14:67-77.
61. Yoo et al. (2010) Curr Pharm Des 16:2298-2307.
62. Thery et al. (2009) Immunology 9:581-593.
63. Zoller (2009) Nat Rev Cancer 9:40-55.
64. Alvarez-Erviti et al. (2011) Nat Biotechnol 29:341-345.
65. Kolhatkar et al. (2011) Curr Drug Discov Technol 8:197-206.
66. Nukolova et al. (2011) Biomaterials 32:5417-5426.
67. Chen et al. (2011) Drug Dev Ind Pharm 37:1339-1346.
68. Liu et al. (2001) J Org Chem 66:5655-5663.
69. Reddy & Low (1998) Crit Rev Ther Drug Carrier Syst 15:587-627.
70. Xiang et al. (2010) Am J Pathol 177:1606-1610.
71. Yamashita et al. (2011) Nat Nanotechnol 6:321-328.
72. Sood et al. (2011) Nat Nanotechnol 6:824-833.
73. Haugland & You (1995) Methods Mol Biol 45:223-233.
74. Elbashir et al. (2001) Nature 411:494-498.
75. Leamon & Jackman (2008) Vitam Horm 79:203-233.
76. Wang & Low (1998) J Control Release 53:39-48.
77. Kwon et al. (2012) J Control Release 164:108-114.
78. Hirsjarvi et al. (2011) Curr Drug Discov Technol 8:188-196.
79. Spilman et al. (2009) J Gen Virol 90:527-535.
80. Liu et al. (2010) Am J Pathol 176:2490-2499.
81. Xiao et al. (2010) Plant Cell 22:1463-1482.
82. Wang et al. (2008) J Immunol 181:5242-5248.
83. Deng et al. (2009) Diabetes 58:2498-2505.
84. Deng et al. (2009) Hepatology 50:1412-1420.
85. PCT International Patent Application Serial No. PCT/US2011/023747, entitled "Exosomal Compositions for the Treatment of Disease."

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A composition, comprising a therapeutic agent encapsulated by a microvesicle, wherein the microvesicle is isolated from a juice of an edible plant, and further wherein the microvesicle is 50-1000 nm in size and is free from unwanted molecules.

2. The composition of claim 1, wherein the edible plant is a fruit.

3. The composition of claim 2, wherein the fruit is selected from a grape, a grapefruit, and a tomato.

4. The composition of claim 1, wherein the therapeutic agent is selected from a phytochemical agent, a stat3 inhibitor, and a chemotherapeutic agent.

5. The composition of claim 4, wherein the therapeutic agent is a phytochemical agent, and wherein the phytochemical agent is selected from curcumin, resveratrol, baicalein, equol, fisetin, and quercetin.

6. The composition of claim 4, wherein the therapeutic agent is a stat3 inhibitor, and wherein the stat3 inhibitor is JSI-124.

7. The composition of claim 4, wherein the therapeutic agent is a chemotherapeutic agent, and wherein the chemotherapeutic agent is selected from the group consisting of retinoic acid, 5-fluorouracil, vincristine, actinomycin D, adriamycin, cisplatin, docetaxel, doxorubicin, and taxol.

8. The composition of claim 1, wherein the therapeutic agent comprises a nucleic acid molecule selected from an siRNA, a microRNA, and a mammalian expression vector.

9. A pharmaceutical composition, comprising a composition according to claim 1 and a pharmaceutically-acceptable vehicle, carrier, or excipient.

\* \* \* \* \*